(12) United States Patent
Bode et al.

(10) Patent No.: US 12,297,475 B2
(45) Date of Patent: May 13, 2025

(54) SYSTEM FOR THE ASSEMBLY AND MODIFICATION OF NON-RIBOSOMAL PEPTIDE SYNTHASES

(71) Applicant: Johann Wolfgang Goethe-Universität Frankfurt am Main, Frankfurt am Main (DE)

(72) Inventors: Helge B. Bode, Oberursel (DE); Kenan Bozhüyük, Frankfurt am Main (DE); Annabell Linck, Frankfurt am Main (DE)

(73) Assignee: Johann Wolfgang Goethe-Universität Frankfurt am Main (DE)

( * ) Notice: Subject to any disclaimer, the term of this patent is extended or adjusted under 35 U.S.C. 154(b) by 283 days.

(21) Appl. No.: 16/962,017

(22) PCT Filed: Jan. 15, 2019

(86) PCT No.: PCT/EP2019/050853
§ 371 (c)(1),
(2) Date: Jul. 14, 2020

(87) PCT Pub. No.: WO2019/138117
PCT Pub. Date: Jul. 18, 2019

(65) Prior Publication Data
US 2020/0347428 A1    Nov. 5, 2020

(30) Foreign Application Priority Data

Jan. 15, 2018  (EP) .................................... 18151588

(51) Int. Cl.
C12P 21/02 (2006.01)
C12N 9/00 (2006.01)

(52) U.S. Cl.
CPC ............... *C12P 21/02* (2013.01); *C12N 9/93* (2013.01)

(58) Field of Classification Search
None
See application file for complete search history.

(56) References Cited

U.S. PATENT DOCUMENTS 11,473,078 B2 * 10/2022 Niesert .................... C40B 40/06
2010/0285563 A1   11/2010 Marahiel et al.

FOREIGN PATENT DOCUMENTS

| EP | 3511445 | 7/2019 |
|---|---|---|
| WO | WO 2000/052152 | 9/2000 |
| WO | WO 2001/030985 | 5/2001 |
| WO | WO 2007/014076 | 2/2007 |
| WO | WO 2017/020983 | 2/2017 |
| WO | WO-2017020983 A1 * | 2/2017 ............. A61P 31/04 |
| WO | WO 2019/138117 | 7/2019 |

OTHER PUBLICATIONS

Stuart W. Haynes "Unraveling Terminal C-Domain-Mediated Condensation in Fungal Biosynthesis of Imidazoindolone Metabolites" Biochemistry 2011, 50, 5668-5679. (Year: 2011).*
Henning D. Mootz Construction of hybrid peptide synthetases by module and domain fusions. PNAS May 23, 2000 97 (11) 5848-5853. (Year: 2000).*
Bozhuyuk et al., "De novo design and engineering of non-ribosomal peptide synthetases," Nature Chemistry (2018) 10:275-281.
Bozhuyuk et al., "Modification and de novo design of non-ribosomal peptide synthetases using specific assembly points within condensation domains," Nature Chemistry (2019) 11:653-661.
International Search Report and Written Opinion for PCT/EP2019/050853, dated Apr. 8, 2019.
Menon et al., "Biosynthesis: Reprogramming assembly lines," Nat Chem (2018) 10(3):245-247.
Sussmuth et al., "Nonribosomal Peptide Synthesis-Principles and Prospects," Angew Chem Int Ed Engl (2017) 56(14):3770-3821.
International preliminary report on patentability for PCT/EP2019/050853, dated Jul. 21, 2020, 7 pages.
Altschul et al., "Basic local alignment search tool," J Mol Biol. (1990) 215(3): 403-10.
Belshaw et al., "Aminoacyl-CoAs as probes of condensation domain selectivity in nonribosomal peptide synthesis," Science. (1999) 284(5413): 486-9.
Bloudoff et al., "Crystal structures of the first condensation domain of CDA synthetase suggest conformational changes during the synthetic cycle of nonribosomal peptide synthetases," J Mol Biol. (2013) 425(17): 3137-50.
Bode et al., "Determination of the absolute configuration of peptide natural products by using stable isotope labeling and mass spectrometry," Chemistry. (2012) 18(8): 2342-8.
Bode et al., "Structure Elucidation and Activity of Kolossin A, the D-/L-Pentadecapeptide Product of a Giant Nonribosomal Peptide Synthetase," Angew Chem int Ed Engl. (2015) 54(35): 10352-5.
Bozhueyuek et al., "Synthetic Zippers as an Enabling Tool for Engineering of Non-Ribosomal Peptide Synthetases," Angew Chem Int Ed Engl. (2021) 60(32):17531-17538.

(Continued)

*Primary Examiner* — Richard G Hutson
(74) *Attorney, Agent, or Firm* — MORRISON & FOERSTER LLP

(57) ABSTRACT

The present invention pertains to a system for the assembly and modification of non-ribosomal peptide synthases (NRPS). The system uses novel well defined building blocks (units) comprising condensation subdomains. This strategy allows for the efficient combination of assembly units referred to as eXchange Units (XU2.0) independent on their natural occurring specificity for the subsequent NRPS adenylation domain. The system of the invention allows for the easy assembly of NRPS having any amino acid sequence of choice, without any restrictions due to natural occurring NRPS units. The system also allows the exchange of natural NRPS building blocks with the inventive XU2.0 leading to the production of modified peptides. The invention provides the system, their individual exchange units, nucleic acids encoding these units, as well as methods and uses thereof.

Figure 1:
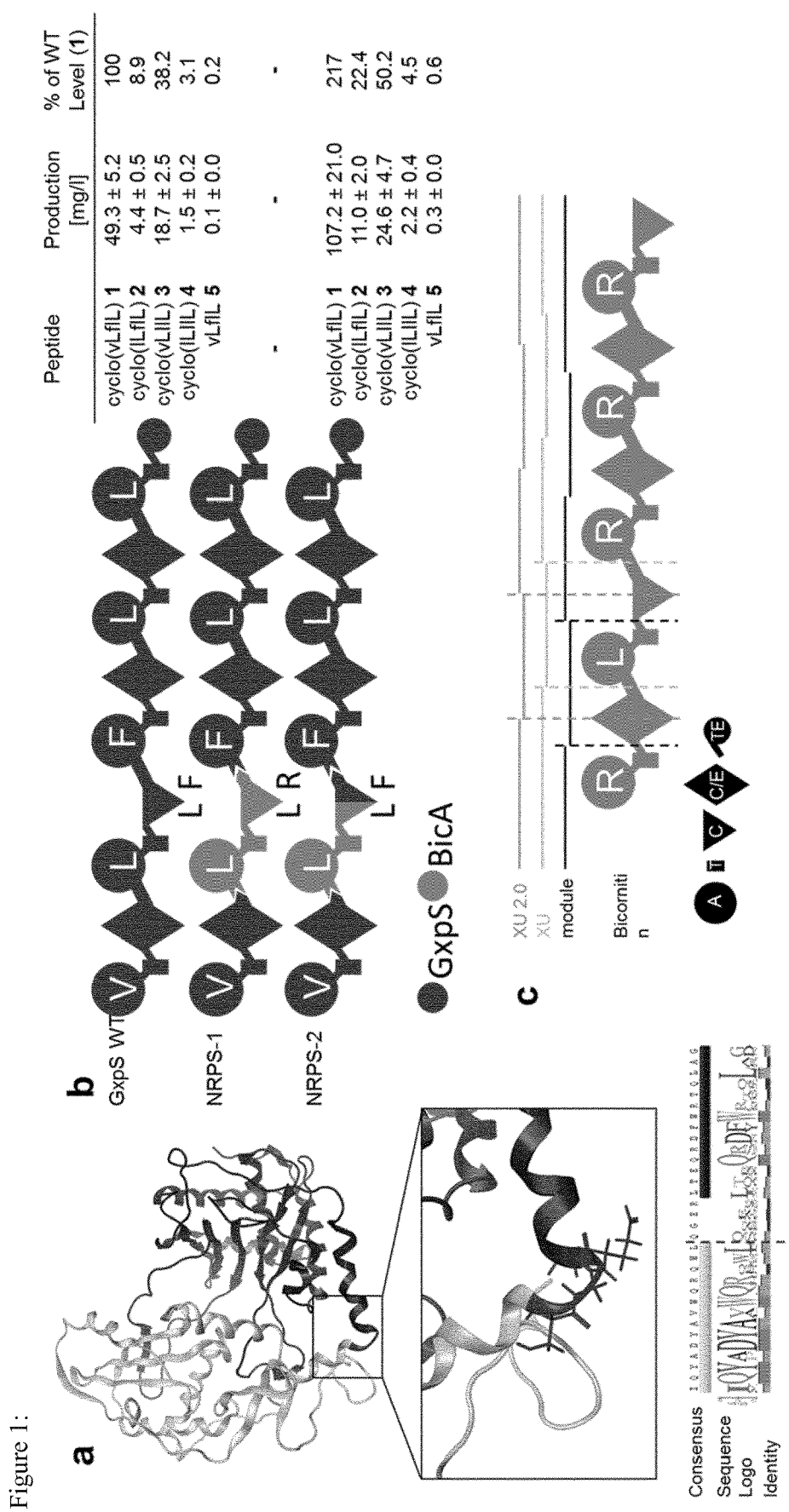

16 Claims, 8 Drawing Sheets
Specification includes a Sequence Listing.

(56) References Cited

OTHER PUBLICATIONS

Bozhüyük et al., "Natural Products from Photorhabdus and Other Entomopathogenic Bacteria," Curr Top Microbiol Immunol. (2017) 402:55-79.
Bruner et al., "Structural basis for the cyclization of the lipopeptide antibiotic surfactin by the thioesterase domain SrfTE," Structure. (2002) 10(3): 301-10.
Cai et al., "Entomopathogenic bacteria use multiple mechanisms for bioactive peptide library design," Nat Chem. (2017) 9(4):379-386.
Calcott et al., "Genetic manipulation of non-ribosomal peptide synthetases to generate novel bioactive peptide products," Biotechnol Lett. (2014) 36(12): 2407-16.
Cane et al., "Harnessing the biosynthetic code: combinations, permutations, and mutations," Science. (1998) 282(5386): 63-8.
Clugston et al., "Chirality of peptide bond-forming condensation domains in nonribosomal peptide synthetases: the C5 domain of tyrocidine synthetase is a (D)C(L) catalyst," Biochemistry. (2003) 42(41): 12095-104.
Conti et al., "Structural basis for the activation of phenylalanine in the non-ribosomal biosynthesis of gramicidin S," EMBO J. (1997) 16(14): 4174-83.
Cosmina et al., "Sequence and analysis of the genetic locus responsible for surfactin synthesis in Bacillus subtilis," Mol Microbiol. (1993) 8(5): 821-31.
De Crecy-Lagard et al., "Multienzymatic non ribosomal peptide biosynthesis: identification of the functional domains catalysing peptide elongation and epimerisation," C R Acad Sci III. (1995) 318(9):927-36.
Du et al., "PKS and NRPS release mechanisms," Nat Prod Rep. (2010) 27(2):255-78.
Emmel et al., "Cyclosporin A specifically inhibits function of nuclear proteins involved in T cell activation," Science. (1989) 246(4937):1617-20.
Fuchs et al., "Formation of 1,3-cyclohexanediones and resorcinols catalyzed by a widely occurring ketosynthase," Angew Chem Int Ed Engl. (2013) 52(15):4108-12.
Fuchs et al., "Structure elucidation and biosynthesis of lysine-rich cyclic peptides in Xenorhabdus nematophila," Org Biomol Chem. (2011) 9(9):3130-2.
Fuchs et al., "Fabclavines: bioactive peptide-polyketide-polyamino hybrids from Xenorhabdus," Chembiochem. (2014) 15(4):512-516.
Fuchs et al., "Neutral loss fragmentation pattern based screening for arginine-rich natural products in Xenorhabdus and Photorhabdus," Anal Chem. (2012) 84(16):6948-55.
Gao et al., "Cyclization of fungal nonribosomal peptides by a terminal condensation-like domain," Nat Chem Biol. (2012) 8(10):823-30.
Gaudelli et al., "Epimerization and substrate gating by a TE domain in β-lactam antibiotic biosynthesis," Nat Chem Biol. (2014) 10(4):251-8.
Gietz et al., "Frozen competent yeast cells that can be transformed with high efficiency using the LiAc/SS carrier DNA/PEG method," Nat Protoc. (2007) 2(1): 1-4.
Harvey et al., "The re-emergence of natural products for drug discovery in the genomics era," Nat Rev Drug Discov. (2015) 14(2):111-29.
Horsman et al., "Polyketide synthase and non-ribosomal peptide synthetase thioesterase selectivity: logic gate or a victim of fate?," Nat Prod Rep. (2016) 33(2):183-202. doi: 10.1039/c4np00148f.
Ishizuka et al., "Activity and toxicity of bleomycin," J Antibiot (Tokyo). (1967) 20(1):15-24.
Keating et al., "The structure of VibH represents nonribosomal peptide synthetase condensation, cyclization and epimerization domains," Nat Struct Biol. (2002) 9(7):522-526.
Kegler et al., "Rapid determination of the amino acid configuration of xenotetrapeptide," Chembiochem. (2014) 15(6):826-828.
Khurana et al., "Genome scale prediction of substrate specificity for acyl adenylate superfamily of enzymes based on active site residue profiles," BMC Bioinformatics. 2010; 11: 57.
Klaus et al., "Engineering of Chimeric Polyketide Synthases Using SYNZIP Docking Domains," ACS Chem Biol. (2019) 14(3):426-433.
Kohli et al., "Generality of peptide cyclization catalyzed by isolated thioesterase domains of nonribosomal peptide synthetases," Biochemistry. (2001) 40(24):7099-108.
Kolb et al., "The growing impact of click chemistry on drug discovery," Drug Discov Today. (2003) 8(24): 1128-37.
Konz et al., "The bacitracin biosynthesis operon of Bacillus licheniformis ATCC 10716: molecular characterization of three multi-modular peptide synthetases," Chem Bio. (1998). 4, 927-937.
Kopp et al., "Macrocyclization strategies in polyketide and nonribosomal peptide biosynthesis," Nat Prod Rep. (2007) 24(4): 735-49.
Korman et al., "Structure and function of an iterative polyketide synthase thioesterase domain catalyzing Claisen cyclization in aflatoxin biosynthesis," Proc Natl Acad Sci USA. (2010) 107(14): 6246-51.
Kries et al., "Reprogramming nonribosomal peptide synthetases for "clickable" amino acids," Angew Chem Int Ed Engl. (2014) 53(38):10105-8.
Kries et al., "A subdomain swap strategy for reengineering nonribosomal peptides," Chem Biol. (2015) 22(5): 640-8.
Kronenwerth et al., "Characterisation of Taxlllaids A—G; Natural Products from Xenorhabdus indica," Chemistry—A European Journal (2014) 20; 17478-87.
Lefevre et al., "Drugs from hidden bugs: their discovery via untapped resources," Res Microbiol. (2008) 159(3):153-61.
Li et al., "Identification and Characterization of the Sulfazecin Monobactam Biosynthetic Gene Cluster,"Cell Chem Biol. (2017) 24(1): 24-34.
Ling et al., "A new antibiotic kills pathogens without detectable resistance," Nature. (2015) 517, 445-459.
Loeffler et al., "Antifungal Effects of Bacilysin and Fengymycin from Bacillus subtilis F-29-3 A Comparison with Activities of Other Bacillus Antibiotics," J hytopathol. (1986) 115(3); 204-213.
Marahiel et al., "Protein templates for the biosynthesis of peptide antibiotics," Chem Biol. (1997) 4(8): 561-567.
Marahiel, "A structural model for multimodular NRPS assembly lines," Nat Prod Rep. (2016) 33(2):136-40.
Medema et al., "antiSMASH: rapid identification, annotation and analysis of secondary metabolite biosynthesis gene clusters in bacterial and fungal genome sequences," Nucleic Acids Res. Jul. 2011;39(Web Server issue):W339-46.
Meyer et al., "Biochemical Dissection of the Natural Diversification of Microcystin Provides Lessons for Synthetic Biology of NRPS," Cell Chem Biol. (2016) 23(4): 462-71.
Mitchell et al., "Structure of PA1221, a nonribosomal peptide synthetase containing adenylation and peptidyl carrier protein domains," Biochemistry. (2012) 51(15): 3252-63. (2012).
Muller et al., "Protein fusions to coiled-coil domains," Methods Enzymol. (2000) 328:261-82.
Nishihara et al., "Overexpression of trigger factor prevents aggregation of recombinant proteins in *Escherichia coli*," Appl Environ Microbiol. (2000) 66(3): 884-889.
Nollmann et al., "Insect-specific production of new GameXPeptides in photorhabdus luminescens TTO1, widespread natural products in entomopathogenic bacteria," Chembiochem. (2015) 16(2): 205-208.
Phelan et al., "Adenylation enzyme characterization using gamma-(18)O(4)-ATP pyrophosphate exchange," Chem Biol. (2009) 16(5): 473-8.
Rausch et al., "Phylogenetic analysis of condensation domains in NRPS sheds light on their functional evolution," BMC Evol Biol. (2007) 7:78.
Rausch et al., "Specificity prediction of adenylation domains in nonribosomal peptide synthetases (NRPS) using transductive support vector machines (TSVMs)," Nucleic Acids Res. (2005) 33(18):5799-808.
Reimer et al., "Rhabdopeptides as insect-specific virulence factors from entomopathogenic bacteria," Chembiochem. (2013) 14(15):1991-7.

(56) References Cited

OTHER PUBLICATIONS

Rottig et al., "NRPSpredictor2—a web server for predicting NRPS adenylation domain specificity," Nucleic Acids Res. (2011);39(2):W362-7.

Samel et al. Structural and Functional Insights into a Peptide Bond-Forming Bidomain from a Nonribosomal Peptide Synthetase, Structure. (2007) 15(7):781-92.

Schimming et al., "Yeast homologous recombination cloning leading to the novel peptides ambactin and xenolindicin," Chembiochem. (2014) 15(9):1290-4.

Sieber et al., "Molecular mechanisms underlying nonribosomal peptide synthesis: approaches to new antibiotics," Chem Rev. (2005) 105(2): 715-38.

Sletten et al., "Bioorthogonal chemistry: fishing for selectivity in a sea of functionality," Angew Chem Int Ed Engl. (2009) 48(38):6974-98.

Smith et al., "The type I fatty acid and polyketide synthases: a tale of two megasynthases," Nat Prod Rep. (2007) 24(5): 1041-72.

Stachelhaus et al., "Peptide bond formation in nonribosomal peptide biosynthesis. Catalytic role of the condensation domain," J Biol Chem. (1998) 273(35): 22773-81.

Stachelhaus et al., "The specificity-conferring code of adenylation domains in nonribosomal peptide synthetases," Chem Biol. (1999) 6(8):493-505.

Stachelhaus et al., "Rational design of peptide antibiotics by targeted replacement of bacterial and fungal domains," Science. (1995) 269(5220):69-72.

Stachelhaus et al., "Modular structure of genes encoding multifunctional peptide synthetases required for non-ribosomal peptide synthesis," FEMS Microbiol Lett. (1995) 125(1):3-14.

Streiker et al., "Nonribosomal peptide synthetases: structures and dynamics," Curr Opin Struct Biol. (2010) 20(2): 234-40.

Sundlove et al., "Structure determination of the functional domain interaction of a chimeric nonribosomal peptide synthetase from a challenging crystal with noncrystallographic translational symmetry," Acta Crystallogr D Biol Crystallogr. (2013) 69(Pt 8):1482-92. (2013).

Tan et al., "Structure of the adenylation-peptidyl carrier protein didomain of the Microcystis aeruginosa microcystin synthetase McyG," Acta Crystallogr D Biol Crystallogr. (2015) 71(Pt 4):873-81.

Tanovic et al., "Crystal structure of the termination module of a nonribosomal peptide synthetase," Science. (2008) 321(5889):659-63.

Trauger et al., "Peptide cyclization catalysed by the thioesterase domain of tyrocidine synthetase," Nature. (2000) 407(6801):215-8.

Tseng et al., "Characterization of the surfactin synthetase C-terminal thioesterase domain as a cyclic depsipeptide synthase," Biochemistry. (2002) 41(45):13350-9.

Winn et al., "Recent advances in engineering nonribosomal peptide assembly lines," Nat Prod Rep. (2016) 33(2): 317-47.

* cited by examiner

| Peptide | Production [mg/l] | % of WT Level (9) |
|---|---|---|
| cyclo(vLvV) 9 | 134.07 ± 26.94 | 100 |
| cyclo(vLvV) 9 | 7.51 ± 1.24 | 5.6 |
| vLfV 10 | 5.58 ± 0.36 | 4.2 |
| vLfL 11 | 6.52 ± 0.50 | 4.9 |
| vLIV 12 | 0.23 ± 0.01 | 0.2 |
| vLIL 13 | 0.17 ± 0.02 | 0.1 |
| cyclo (vLfV)14 | 106.63 ± 15.59 | 79.1 |
| cyclo (vLIV)15 | 80.12 ± 6.34 | 59.7 |
| vL-[p-N$_3$-f]-L 16 | 228.7 ± 27.17 | 170 |
| vL-[p-N$_3$-f]-V 17 | 283.51 ± 29.45 | 211 |
| cyclo(vL-[p-N$_3$-f]-V) 18 | 30.44 ± 2.25 | 22.4 |
| cyclo(vLvV) 9 | 4.18 ± 1.35 | 3.1 |
| vLfV 10 | 1.88 ± 0.23 | 1.4 |
| vLfL 11 | 1.79 ± 0.15 | 1.3 |
| vLIV 12 | 0.06 ± 0.01 | 0.04 |
| vLIL 13 | 0.04 ± 0.01 | 0.03 |
| cyclo (vLfV)14 | 72.64 ± 0.59 | 54.2 |
| cyclo (vLIV)15 | 48.35 ± 2.51 | 36.1 |
| vL-[¥-y]-V 19 | 4.74 ± 0.55 | 3.5 |
| vL-[¥-y]-L 20 | 7.00 ± 0.33 | 5.2 |
| cyclo(vL-[¥-y]-V) 21 | 4.93 ± 0.33 | 3.7 |
| cyclo(vLvV) 9 | 3.74 ± 1.14 | 2.8 |
| vLfV 10 | 1.81 ± 0.17 | 1.4 |
| vLfL 11 | 2.03 ± 0.31 | 1.5 |
| vLIV 12 | 0.08 ± 0.01 | 0.06 |
| vLIL 13 | 0.04 ± 0.01 | 0.03 |
| cyclo (vLfV)14 | 61.55 ± 6.72 | 45.9 |
| cyclo (vLIV)15 | 45.30 ± 3.75 | 33.8 |

SYSTEM FOR THE ASSEMBLY AND MODIFICATION OF NON-RIBOSOMAL PEPTIDE SYNTHASES

CROSS REFERENCE TO RELATED APPLICATIONS

This application is a national stage application under 35 U.S.C. § 371 of International Application No. PCT/EP2019/050853, filed internationally on Jan. 15, 2019, which claims the benefit of priority to European Application No. 18151588.3, filed Jan. 15, 2018.

SUBMISSION OF SEQUENCE LISTING ON ASCII TEXT FILE

The present application is being filed along with a Sequence Listing in electronic format. The Sequence Listing is provided as a file entitled 595282002600SeqList.txt, created Jul. 13, 2020 which is 35,438 bytes in size. The information in the electronic format of the Sequence Listing is incorporated by reference in its entirety.

FIELD OF THE INVENTION

The present invention pertains to a system for the assembly and modification of non-ribosomal peptide synthases (NRPS). The system uses novel well defined building blocks (units) comprising condensation subdomains. This strategy allows for the efficient combination of assembly units referred to as eXchange Units ($XU_{2.0}$) independent on their natural occurring specificity for the subsequent NRPS adenylation domain. The system of the invention allows for the easy assembly of NRPS having any amino acid sequence of choice, without any restrictions due to natural occurring NRPS units. The system also allows the exchange of natural NRPS building blocks with the inventive $XU_{2.0}$ leading to the production of modified peptides. The invention provides the system, their individual exchange units, nucleic acids encoding these units, as well as methods and uses thereof.

DESCRIPTION

Non-ribosomal peptide synthetases (NRPSs) and polyketide synthases (PKSs) are multifunctional enzyme complexes harboring a modular architecture (Marahiel 1997). Numerous natural products synthesized by these enzyme classes are of pharmaceutical and/or biotechnological interest because of its medicinally relevant properties including antimicrobial (e.g. teixobactin), antitumor (e.g. bleomycin), antifungal (fengycin) and immunosuppressant (cyclosporin) activity (Ling et al. 2015, Ishizuka et al. 1967, Loeffler et al. 1986, Emmel et al. 1989). Although the peptidic compounds produced by NRPSs exhibit a broad range of bioactivity and a great structural variety (e.g. non-proteinogenic amino acids, N-methylation, epimerization, heterocycles), a common mode of synthesis is shared, the so called "multiple-carrier thiotemplate mechanism".

The structure of NRPSs is obligate modular. A module is defined as the catalytic unit that incorporates one specific building block (e.g. amino acid) into the growing peptide chain (Marahiel 1997). NRPS modules can be subdivided into domains and each domain is responsible for a certain reaction step within peptide assembly. For example, a canonical elongation module is composed of three domains, denoted as core domains:

- adenylation (A) domain which selectively determines and activates substrates (usually amino-acids) as an amino acyl adenylate.
- A peptidyl carrier protein (PCP), also called thiolation domain (T) binds the cofactor 4-phosphopantethein, to which the activated amino acid (AA) is covalently bound by thioester formation.
- A condensation (C) domain catalyzes peptide bond formation between the downstream and upstream located aminoacyl or peptidyl residues.

The first (N-terminal) module (start module) of a NRPS module often possesses no C domain and the last (C-terminal) module (termination module) usually contains a thioesterase (TE) domain (Marahiel et al. 1997). The TE domain usually is responsible for the release of linear (transfer to a water molecule), cyclic or branched cyclic peptides (amide or ester linkage).

The following domains may be included within a NRPS: C (condensation), Cy (heterocyclization), A (adenylation), T (thiolation) or PCP (peptidyl carrier protein), TE (thioesterase), E (epimerization), condensation/epimerization (C/E), MT (methyltransferase), Ox (oxidase), and Re (reductase) domains. NRPSs generally have the following structure: A-T-(C-A-T)n-C-A-T-TE where A-T is the initiation module, C-A-T are the elongation modules, and C-A-T-TE is the termination module. Within the individual modules, the following variations may, for example, occur: C is replaced by Cy or C/E, and E, MT, Ox, or Re are inserted; TE is replaced by C or Re. A complete assembly line may have an initiation module, a termination module, and somewhere between zero and n−2 elongation modules, where n is the number of monomers in the polymeric product. Exceptions to this rule may exist; e.g., the enterobactin synthetase, in which the TE domain acts as an oligomerase, so although it only has two modules, it hooks three of these dimeric products together to form a hexameric peptide product.

NRPSs are generally modular, and the series of catalytic steps moves from the amino to carboxy terminus of each polypeptide that makes up the NRPS. For example, the NRPS that produces tyrocidine is made of three genes producing three polypeptides. TycA contains the initiation module; TycB contains three elongation modules, and TycC contains six additional elongation modules plus a termination module.

The following domains may be included within a PKS: KS (ketosynthase), AT (acyltransferase), T (thiolation), KR (ketoreductase), DH (dehydratase), ER (enoylreductase), TE (thioesterase). PKSs generally have the following structure: AT-T-(KS-AT-T)n-TE. AT-T is the initiation module, KS-AT-T are the elongation modules, and TE is the termination module. The structure of a PKS is very similar to NRPS structure. There are many examples (e.g., yersiniabactin, epothilone, Neomycin) of hybrid PKS-NRPS systems in which both types of assembly line are pieced together to form a coherent unit. Within each PKS module, one either finds a KR, a KR and DH, a KR and DH and ER, or no additional domains. These extra domains within a module determine the chemical functionality at the beta carbon (e.g., carbonyl, hydroxyl, olefin, or saturated carbon).

The power of NRPs and PKs as potential drugs lies in their diverse and complicated chemical structures. Generally, it is the intricacy of these natural products that makes them (or variants thereof) difficult to access synthetically. Several examples exist where laborious synthetic routes have been developed, rarely successfully, for NRPs or PKs. Additionally, various moieties on such molecules are inaccessible to modification by organic synthesis, or can only be produced at low yields using such techniques. This difficultly in synthesis and modification of the NRP and PK natural products underscores the need for alternative strategies to enhance synthesis and create variants of these molecules.

Despite the apparent modular structure of the NRPSs, it has, prior to the inventor's previous invention (EP15002340) and the present invention, in practice been difficult to swap domains so that the resulting NRPS is active. Substitution of one or more domain or modules for another generally results in low yields (e.g., >10-fold reductions) and in the production of undesirable biosynthetic side products. These changes may be a result of disruptions of protein-protein interactions and due to the substrate specificities of C and TE domains, respectively. Thus, there is a need for new methods to produce novel NRPs and PKs and a need for methods that increase the yields of such NRPs and PKs.

For further general information on NRPSs and PKSs see Cane et al. (1998), Marahiel (1997), Sieber and Marahiel (2005), Smith and Tsai (2007) and Süssmuth and Mainz (2017).

After activation and covalent binding of the first AA by the A-T didomain initiation module, peptide elongation proceeds by subsequent condensation with building blocks covalently tethered to T domains of the downstream (C terminal) elongation modules (C-A-T)n (Sieber and Marahiel 2005 or Süssmuth and Mainz 2017). All elongation reactions (peptide and amide bond formation) are mediated by ca 450 AA long C domains, located in between the upstream T and downstream A domain and are strictly unidirectional leading to a downstream-directed synthesis of the NRPS product (Samel et al. 2007). C domains catalyze the nucleophilic attack of the downstream T domain bound acceptor AA with its free α-amino group on the activated thioester of the upstream T domain bound donor AA or peptide.

Biochemical characterizations of C domains revealed insights into their catalytic role and substrate specificities. Via deletion experiments Stachelhaus and colleagues (1998) brought to light that C domains are indispensable for peptide bond formation. Furthermore, sequence alignments of several C domains revealed a highly conserved HHXXXDG sequence motif (the so called "His motif") that is also present in acyltransferases (e.g. chloramphenicol acetyltransferase), NRPS E, and Cy domains (De Crecy-Lagard et al., 1995). Mutations of the second His residue in the conserved motif abolished activity in condensation assays (Sieber and Marahiel 2005).

Structures which include NRPS C domains have been determined by X-ray crystallography: a stand-alone C domain (Keating et al., 2002), a C-T didomain (Samel et al., 2007) and a C-A-T-TE termination module (Tanovic et al., 2008). C domains have a pseudo-dimer configuration, with both N- and C-terminal subdomains having cores with folds in the CoA dependent acyltransferase superfamily (Bloudoff et al. 2013). The active site is at the bottom of a "canyon" formed by the two subdomains, and is covered by a "latch" that crosses over from C to N subdomain. The catalytic center, including the HHXXXDG (where X denotes any residue) motif, has two binding sites: one for the electrophilic donor substrate (the acyl group of the growing chain) and one for the nucleophilic acceptor substrate (the activated amino acid) (Rausch et al., 2007).

Although, little is known about the reaction C domains catalyze, biochemical characterization of different C domains from the tyrocidine synthetases (Belshaw et al. 1999; Clugston et al. 2003; Samel et al. 2007) revealed insights into their substrate specificities. All C domain characterizations were performed in vitro and used the same method to investigate the substrate acceptance of internal C domains. The upstream and/or downstream T domains were chemo-enzymatically primed (transfer of synthetic peptidyl-Ppan arms) with acceptor substrates by the use of the permissive PPTase Sfp (Belshaw et al. 1999; Samel et al. 2007). In summary, with this method it was shown that the acceptor site of the C domain exhibits a strong stereo and significant side chain selectivity (Rausch et al. 2007). The selectivity towards a specific side chain seems to be less pronounced at the donor site which exhibits strong stereoselectivity. C domains succeeding E domains show specificity towards the configuration of the C terminal residue bound at the donor site because the preceding E domain doesn't specifically catalyze the epimerization from L to D, yet provides a mixture of configurations. C domains immediately downstream of E domains were shown to be D-specific for the upstream donor and L-specific for the downstream acceptor, thus catalyzing the condensation reaction between a D- and an L-residue (Clugston et al., 2003).

C domains can be subdivided into functional and phylogenetic subtypes (Rausch et al. 2007). There are "standard" C domains within elongation modules like $^{L}C_{L}$ domains, which catalyze peptide bond formation between two L-AA, and $^{D}C_{L}$ domains connecting a L-amino acid to a growing peptide ending with a D-amino acid (Rausch et al., 2007). Starter C domains acylating the first amino acid with a carboxylic acid (often a β-hydroxyl fatty acid) and heterocyclization (CY) domains which catalyze both peptide bond formation and subsequent cyclization of cysteine, serine or threonine residues (Rausch et al. 2007). The homologous Epimerization (E) domain flips the chirality of the last amino acid in the growing peptide and Dual C/E domains catalyze both condensation and epimerization.

The most common way of multienzyme reactivation is via TE domains, which belong to the α/β-hydrolase superfamily (lipases, proteases and esterases) (Du and Lu 2009). These enzymes are ca. 280 amino acid long and are fused to most C-terminal T domain of the termination module (Sieber and Marahiel 2005; Kohli et al. 2001). In the last step of peptide assembly an active site serine of the TE domain carries out a nucleophilic attack on the T domain-peptidyl thioester to form a peptide-O-TE intermediate (Kohli et al. 2001). Deacylation of the intermediate involves either hydrolysis (attack of an exogenous nucleophile) to release a linear peptide or, in the case of cyclic products, reaction of an intramolecular nucleophile (N-, O-, or C-nucleophile). Hydrolytic release is observed for peptides such as vancomycin, whose peptide backbone is constrained by further post-synthetic oxidative cross-linking reactions. Cyclizing TE domains provide a source of diversity and complexity as a variety of groups can be the nucleophile in the cyclization reaction: the N-terminal amino group (head-to-tail cyclization; e.g. tyrocidine A and gramicidin S), a side chain nucleophile (branched cyclic molecule; e.g. bacitracin A and daptomycin), and the β-hydroxyl group of a β-hydroxy fatty acid (e.g. surfactin) (Kohli et al., 2001).

Bruner et al. (2002) solved the first TE crystal structure of the surfactin biosynthesis cluster (SrfTE). In general NRPS TE domains are monomers and consist of an α/β-hydrolase fold with a catalytic triad ((Ser/Cys)-(His)-(Asp/Glu/Ser)) for substrate binding and catalysis via a covalently bound peptide-thioesterase intermediate. Furthermore, TE domains were found to exist in two distinct conformations, the open and the closed state. Differences between both states are restricted to a region of 40 amino acid residues covering most of the active site of the enzyme, which was named the lid region.

Unlike many other catalytic domains involved in the biosynthesis of non-ribosomal peptides, TE domains are highly diverse and consequently no model exists for predicting TE loading or release selectivity (Horsman et al. 2015). Phylogenetic analysis of TE sequences show that they do not duster based on type of offloading chemistry they catalyze.

TE domains operate via a two-step mechanism, loading followed by release (Horsman et al. 2015). The active site Ser side chain alcohol is activated by the conserved His-Asp dyad, increasing its nucleophilicity. The T domain bound substrate approaches the activated Ser, mediated by the 4'Ppant cofactor. It has been hypothesized that the lid region opens to accommodate the presentation of thioester substrates. The deprotonated and conserved active site Ser attacks the substrate thioester and the resulting charged tetrahedral intermediate is stabilized in the oxyanion hole by hydrogen bonding from two backbone amide groups. This intermediate is resolved by loss of the 4'Ppant thiolate, generating the acyl-TE intermediate. The second step (offloading) involves release of the acyl group. This step begins with the approach of an intramolecular or intermolecular nucleophile. Townsend and colleagues (2010, 2014) suggested that the active-site histidinium ion is deprotonated by the departing thiolate and thus capable of activating the incoming nucleophile (Korman et al. 2010, Gaudelli and Townsend 2014). The nucleophile adds into the carbonyl of the acyl-TE intermediate and the tetrahedral intermediate is once again stabilized by the oxyanion hole. Finally the seryl alkoide is released with concerted protonation and the product leaves the active site.

Major insights into TE substrate specificity were gained by Trauger (2000) and Tseng (2002). By the use of synthetic SNAC-peptides (N-acetylcysteamin) they were able to show that TE domains are selective for the stereochemistry as well as the sidechain of the N-terminal AA residue. They also revealed that the AA next to the peptidyl-O-TE forming AA (C terminal AA) is important for peptide hydrolysis and cyclization, whereas all other AA within the produced peptide seem to be not crucial. Furthermore, Kohli et al. (2001) revealed that the excised TE domain from the tyrocidine NRPS accepts a broad spectrum of SNAC-peptides, varying in length and composition, as substrates for cyclization.

A noticeably distinct feature of most fungal NRPS is the replacement of the TE domain with a terminal C, Re, or T domain (Haynes et al. 2011). In addition to NAD(P)H-dependent Re domains, C domains can also be involved in peptide release (Kopp and Marahiel 2007). Whereas most bacterial NRPS use TE domains to perform the cyclization, fungal NRPS as well as some NRPS from bacteria including the genera *Photorhabdus* and *Xenorhabdus* use this complementary strategy (Gao et al. 2012; Reimer et al. 2013).

In macrocyclic fungal NRPSs such as cyclosporine A, aureobasidin A, apicidin and ferrichrome A, each corresponding NRPS catalyzes peptide release via terminal condensation (Cterm) domains (Gao et al. 2012). In the NRPS paradigm, C domains are canonically categorized to catalyze the formation of a peptide bond between the growing peptidyl-S-$T_n$ from module n and the activated aminoacyl-S-$T_{n+1}$ using an active site histidine as the general base. Therefore, it is surprising that the Cterm domain is able to perform the equivalent head-to-tail linkage of a TE domain. The reaction relies on a serine residue of the highly conserved HHxxxDxxS motif in the active site for nucleophilic catalysis and the nucleophile is an intramolecular amino group, rather than the next AA (Kopp and Marahiel 2007). Gao et al. (2012) revealed that Cterm cyclization activity requires the presence of a T domain. Furthermore, via construction of recombinant T-Cterm didomains they were able to show that non-cognate T domains do not interact with the downstream Cterm domain. Therefore, protein-protein interactions between the Cterm and the upstream T domain seem to be specific and might rely on T domain sequence elements that are unique for recognition by C domains. However, although terminal C domains are cited as controlling the cyclization of NRPS-based intermediates, there is as yet no experimental evidence to illustrate their proposed catalytic activity (Haynes et al. 2011).

Besides Cterm domains that catalyze peptide release by cyclization, there are Cterm domains that catalyze the formation of an amide-bond between the linear T-domain bound peptide and an amine from the environment (Reimer et al. 2013; Fuchs et al. 2012, Gao et al. 2012, Cai et al. 2017). One example is the non-ribosomal rhabdopeptide biosynthesis cluster from *Xenorhabdus nematophila*. Here, the Cterm domain might be involved in the condensation of a biogenic amine (e.g., phenylethylamine derived from phenylalanine decarboxylation) with the peptide intermediate during the release process (Reimer et al. 2013; Fuchs et al., 2012).

Since 1995, when Marahiel et al. (WO200052152) were able to show that it is possible to recombine NRPS through exchanging adenylation-thiolation didomains, NRPS research came into focus (Marahiel et al. 1995). During the last two decades, there have been a lot of attempts to reprogram NRPS. Based on the crystal structure of the phenylalanine activating domain PheA (PDB-ID: 1AMU) Stachelhaus et al. were able to elucidate the specificity conferring AAs in the catalytic center (Conti et al. 1997, Stachelhaus et al. 1999). With this specificity conferring code, denoted as Stachelhaus-code it is possible to predict and to change substrate specificities of A domains in vitro, (Khurana et al. 2010, Rausch et al. 2005, Röttig et al. 2011, Kries et al. 2014). The most obvious disadvantage of this attempt is its inapplicability in vivo. One major reason for this drawback is that C and TE domains also have selectivities resulting in substrate incompatibilities (Belshaw et al. 1999; Trauger et al. 2000; Tseng et al. 2002).

A further attempt (WO200130985, Marahiel et al.) to vary known NRPS biosynthetic clusters is based on the exchange of single domains, didomains or whole modules and the knowledge of exactly defined borders (linkers) between individual domains. With this invention it was only possible to alter a few NRPSs successfully by introduction of additional modules or deleting them. However, it never was possible to produce totally artificial NRPSs from the artificial de novo combination of modules. This would result in new NRPS not present in nature that would also produce new peptides. The problem of such exchanges or combinations always was the uncertainty concerning the compatibility of modules and/or domains between each other. The shortcomings resulting from the lack of a solution to the problem mentioned above is illustrated by the fact that almost no artificial peptides have been designed by this approach.

Another attempt (WO2007014076, Walsh et al.) to vary known NRPS biosynthetic clusters is based on mutagenesis of so called "assembly lines" other word for synthases. Mutagenesis of genes of NRPS is not subject of the present invention although the present inventive methods can be combined with a mutagenesis that will alter the generated NRPS and cause altered peptide synthesis. This mutagenesis could be useful for increasing the diversification of NRPS libraries and the NRPS clone numbers in the library.

As A domains are the initial gatekeeping enzymes, the generation of modified peptide products requires substitution, or modification, of the A domain that specifies the target residue in the native peptide. There are three general strategies that researchers have employed to achieve this: (I) substitution of the A or paired A-T domain activating an alternative substrate; (II) targeted alteration of just the substrate binding pocket of the A domain; (III) substitutions that treat C-A or C-A-T domain units as inseparable pairs. These strategies are complemented by recombination studies which have sought to re-engineer NRPS by T, T-C-A, communication domain and A-T-C swapping. However, with exception of the latter and recently published strategy (Bozhüyük et al. 2017), denoted as the concept of eXchange Units (XU), scientists have failed to introduce clearly defined, reproducible and validated guidelines for engineering modified NRPS (WO 2017/020983).

The XU-concept provides three simple rules for the design, cloning and production of NRPs of a desired AA composition, structure and length: (I) A-T-C or A-T-C/E are used as XUs, (II) XUs are fused in the C-A linker at the conserved WNATE sequence, and (III) the specificity of the downstream C domain must be respected. Applying XUs, naturally occurring NRPS assembly lines were reconstructed; new peptide derivatives and completely new artificial NP like peptides were produced. The disadvantage of the XU-concept is that the natural downstream C domain specificity must be obeyed clearly limiting its applicability and the C-domain specificities have to be met—at the donor as well as at the acceptor site. This disadvantage can be accepted if a large number of XUs with different downstream C domains are available. Due to these limitations also at least two XUs have to be exchanged to produce a new peptide derivative that differs in one AA position from the primary sequence of the wild type (WT) peptide. However, a more flexible system would be very desirable.

To be suited for broad application the drawbacks of the XU concept must be reduced. Therefore, the object of the present invention was to establish a more convenient method evading C-domain specificities. Such a method would drastically reduce the amount of NRPS building blocks necessary to produce or alter particular peptides and would enable the creation of artificial natural product libraries with hundreds or thousands of entities for bioactivity screenings.

The above problem is solved in a first aspect by a system for the production of a non-ribosomal peptide synthases (NRPS), wherein the system comprises at least one, preferably two, NRPS eXchange Units ($XU_{2.0}$) each specific for a different or identical amino acid X for assembling an NRPS, and wherein the $XU_{2.0}$ comprises at least one partial condensation (C)- or partial condensation/epimerization (C/E)- domain selected from the group consisting of a condensation-domain acceptor site subdomain ($C_{Asub}$) specific for a given amino acid X, a condensation/epimerization-domain acceptor site subdomain ($C/E_{Asub}$) specific for a given amino acid X, a condensation-domain donor site subdomain ($C_{Dsub}$) specific for a given amino acid X and a condensation/epimerization-domain donor site subdomain ($C/E_{Dsub}$) specific for a given amino acid X.

In context of the present invention the designation "X" refers to an amino acid specificity of any NRPS module or exchange unit of the invention, for example a partial or complete C or C/E domain, or adenylation A domain. A specificity of such a domain or module may include specificity for one or more amino acid-species. For example, some domains (such as an A domain) have specificity for not only one single amino acid species, but for two, three, four or five or more different amino acid species. For example A domains have specificities for multiple amino acids that are also accepted by the downstream C or C/E domains resulting in the production of several different peptides. Therefore, the present invention also includes such domains which harbor specificity for multiple amino acid species.

The system of the invention preferably comprises an $XU_{2.0}$ wherein the $XU_{2.0}$ comprises at least one C or C/E domain which consists of only a partial sequence of said C or C/E domain, preferably which consists of only the donor or acceptor site of said C or C/E domain. In this respect an $XU_{2.0}$ of the invention may comprise one partial C or C/E domain and optionally in addition one complete C or C/E domain, the latter comprising both C or C/E donor and acceptor sites. Hence, a $XU_{2.0}$ of the invention is preferably characterized by the presence of at least one partial C or C/E domain. In some instances a system according to the invention may be preferred, wherein said at least one $XU_{2.0}$ does not comprise a fully assembled C or C/E domain. However, a system of the invention may preferably comprise more than one $XU_{2.0}$, and therefore may comprise both $XU_{2.0}$ wherein only partial C or C/E domains are present, and $XU_{2.0}$ wherein one complete C or C/E domain is comprised, and in addition, optionally, may comprise additional NRPS exchange units which do not comprise a partial C or C/E domain. Hence, a system of the invention at least comprises one $XU_{2.0}$, in some embodiments in combination with (i) other one or more $XU_{2.0}$, and/or (ii) other prior art exchange units, and/or (iii) other natural occurring NRPS sequences. In addition thereto, the system of the invention may also include exchange units for or derived from PKS.

For the present invention, the following definitions shall be used:

The term "partial domain" or "partial C or C/E domain" or similar expression shall refer to nucleic acid sequence encoding for, or a protein sequence of, an NRPS C or C/E domain which is incomplete (not full length). The term therefore describes a C or C/E domain sequence which does not comprise both donor and acceptor sites of an NRPS C or C/E domain.

By "assembly" is meant a set of domains. A plurality of assembly comprises an NRPS. One or more polypeptides may comprise a module. Combinations of modules can catalyze a series of reactions to form larger molecules. In one example, a module may comprise a C (condensation) domain, an A (adenylation) domain, and a peptidyl carrier protein domain.

For more structural information on A domains, C domains, didomains, domain-domain interfaces and complete modules see Conti et al. (1997), Sundlov et al. (2013), Samel et al. (2007), Tanovic et al. (2008), Strieker and Marahiel (2010), Mitchell et al. (2012) and Tan et al. (2015).

By "initiation module" is meant a N-terminal module which is capable of providing a first monomer to another module (e.g., an elongation or termination module). In some instances the other module is not the second but any of the C-terminally following modules (as is the case for the Nocardicin NRPS): In the case of an NRPS, an initiation module comprises, for example, an A (adenylation) domain and a PCP (peptidyl carrier protein) or T (thiolation) domain. The initiation module may also contain a starter C domain and/or an E (epimerization) domain. In the case of a PKS, a possible initiation module comprises an AT (acetyltransferase) domain and an acyl carrier protein (ACP) domain. Initiation modules are preferably at the amino terminus of a polypeptide of the first module of an assembly line, and each assembly line preferably contains one initiation module.

By "elongation module" is meant a module which adds a monomer to another monomer or to a polymer. An elongation module may comprise a C (condensation), Cy (heterocyclization), E, C/E, MT (methyltransferase), A-MT (combined adenylation and methylation domain), Ox (oxidase), or Re (reductase) domain; an A domain; or a T domain. An elongation domain may further comprise additional E, Re, DH (dehydration), MT, NMet (N-methylation), AMT (Aminotransferase), or Cy domains. Additionally, an elongation module might be of PKS origin comprising the respective domains (ketosynthase (KS), acyltransferase (AT), ketoreductase (KR), dehydratase (DH), enoylreductase (ER), thiolation (T)) connecting an amino acid building block with a carboxylic acid building block.

By "termination module" is meant a module that releases the molecule (e.g., an NRP, PK, or combination thereof) from the assembly line. The molecule may be released by, for example, hydrolysis or cyclization. Termination modules may comprise a TE (thioesterase), $C_{term}$, or Re domain. The termination module is preferably at the carboxy terminus of a polypeptide of an NRPS or PKS. The termination module may further comprise additional enzymatic activities (e.g., oligomerase activity).

By "domain" is meant a polypeptide sequence, or a fragment of a larger polypeptide sequence, with one or more specific enzymatic activities (i.e. C/E domains have a C and a E function in one domain) or another conserved function (i.e. as tethering function for an ACP or T domain). Thus, a single polypeptide may comprise multiple domains. Multiple domains may form modules. Examples of domains include C (condensation), Cy (heterocyclization), A (adenylation), T (thiolation), TE (thioesterase), E (epimerization), C/E (condensation/epimerization), MT (methyltransferase), Ox (oxidase), Re (reductase), KS (ketosynthase), AT (acyltransferase), KR (ketoreductase), DH (dehydratase), and ER (enoylreductase).

By "non-ribsomally synthesized peptide," "non-ribosomal peptide," or "NRP" is meant any polypeptide not produced by a ribosome. NRPs may be linear, cyclized or branched and contain proteinogenic, natural or non-natural amino acids, or any combination thereof. NRPs include peptides produced in an assembly line like manner (=modular character of the enzyme system allowing a stepwise addition of building blocks to form a final product).

By "polyketide" is meant a compound comprising multiple ketyl units.

By "non-ribosomal peptide synthetase" or "non-ribosomal peptide synthase" or "NRPS" is meant a polypeptide or series of interacting polypetides that produce a nonribosomal peptide, thus that is able to catalyze peptide bond formation without the presence of ribosomal components.

By "polyketide synthase" (PKS) is meant a polypeptide or series of polypeptides that produce a polyketide. By "alter an amount" is meant to change the amount, by either increasing or decreasing. An increase or decrease may be by 3%, 5%, 8%, 10%, 15%, 20%, 30%, 40%, 50%, 60%, 70%, 80%, 90%, 100%, or more.

By "non-ribosomal peptide synthetase/polyketide synthase hybrid" or "hybrid of non-ribosomal peptide synthetase and polyketide synthase" or "NRPS/PKS hybrid" or "hybrid of NRPS and PKS" or "hybrid of PKS and NRPS" is meant a enzyme systems comprising any domains or modules from non-ribosomal peptide synthetases and polyketide synthases resulting in the respective hybrid natural products.

By "altering a structure" any change in a chemical (e.g., covalent or noncovalent) bond as compared to a reference structure is meant.

By "mutation" an alteration in the nucleic acid sequence such that the amino acid sequence encoded by the nucleic acid sequence has at least one amino acid alteration from a naturally occurring sequence is meant. The mutation may, without limitation, be an insertion, deletion, frameshift mutation, or a missense mutation. This term also describes a protein encoded by the mutant nucleic acid sequence.

By "variant" a polypeptide or polynucleotide with at least 10%, 20%, 30%, 40%, 50%, 60%, 70%, 80%, 90%, 95%, or 99% sequence identity to a reference sequence is meant. Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications by applying substitution/scoring matrices (e.g. PAM, Blosum, GONET, JTT). Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between e-3 and e-150 indicating a closely related sequence (Altschul et al., 1990).

In some embodiments, the system according to the invention is preferred, wherein at least one $XU_{2.0}$ comprises a C- or C/E acceptor domain and a C- or C/E donor domain separated by one or more NRPS domains other than C or C/E domains. In this embodiment, each single unit consists of one C- or C/E acceptor domain and one C- or C/E donor domain separated by a non-C or non-C/E domain, preferably separated by an adenylation A domain. In other embodiments, the system is preferred wherein each unit within the system comprises (i) only one C- or C/E acceptor domain or only one C- or C/E donor domain; or (ii) comprises only C- or C/E acceptor domain and only one C- or C/E donor domain, wherein the two domains are spatially separated by one or more other NRPS domains.

Preferably an $XU_{2.0}$ of the invention comprises at least the following structure: $Z^X Y^X$ or $Y^X Z^X$; wherein Z is a partial C or C/E domain, preferably $C(\text{or C/E})_{Asub}$ or $C(\text{or C/E})_{Dsub}^X$, and wherein Y is any one or multiple identical or different (or both) NRPS/PKS domain(s) or module(s) having a similar or identical specificity X, wherein X stands for an amino acid specificity of the domain or module to one or more amino acid species. In addition the $XU_{2.0}$ may comprise additional modules or domains at either N or C terminal end.

In other preferred alternative or additional embodiments of the invention, at least one $XU_{2.0}$ has a structure according to any one of the following formulas:

$C_{Asub}^X\text{-}A^X\text{-}T\text{-}C_{Dsub}^X$,     a.

$C/E_{Asub}^X\text{-}A^X\text{-}T\text{-}C/E_{Dsub}^X$,     b.

$C_{Asub}^X\text{-}A^X\text{-}T\text{-}C/E_{Dsub}^X$,     c.

or $C/E_{Asub}^X\text{-}A^X\text{-}T\text{-}C_{Dsub}^X$,     d.

Additional units comprised in the system of the invention may be selected from one or more of the following formulas:

| | |
|---|---|
| $C^X\text{-}A^X\text{-}T\text{-}C_{Dsub}{}^X$ | e. |
| $C/E^X\text{-}A^X\text{-}T\text{-}C_{Dsub}{}^X$ | f. |
| $C^X\text{-}A^X\text{-}T\text{-}C/E_{Dsub}{}^X$ | g. |
| $C/E^X\text{-}A^X\text{-}T\text{-}C/E_{Dsub}{}^X$ | h. |
| $C_{Asub}{}^X\text{-}A^X\text{-}T\text{-}C^X$ | i. |
| $C/E_{Asub}{}^X\text{-}A^X\text{-}T\text{-}C/E^X$ | j. |
| $C_{Asub}{}^X\text{-}A^X\text{-}T\text{-}C/E^X$ | k. |
| $C/E_{Asub}{}^X\text{-}A^X\text{-}T\text{-}C^X$ | l. |
| $C_{start}\text{-}A^X\text{-}T\text{-}C_{Dsub}{}^X$, | m. |
| $A^X\text{-}T\text{-}C_{Dsub}{}^X$, | n. |
| $C_{start}\text{-}A^X\text{-}T\text{-}C/E_{Dsub}{}^X$ | o. |
| $A^X\text{-}T\text{-}C/E_{Dsub}{}^X$, | p. |
| $C_{Asub}{}^X\text{-}A^X\text{-}T\text{-}TE$ | q. |
| $C/E_{Asub}{}^X\text{-}A^X\text{-}T\text{-}TE$ | r. |
| $C_{Asub}{}^X\text{-}A^X\text{-}T\text{-}C_{term}$ | s. |
| $C/E_{Asub}{}^X\text{-}A^X\text{-}T\text{-}C_{term}$ | t. |
| $C_{Asub}{}^X\text{-}Y^X\text{-}C_{Dsub}{}^X$ | u. |
| $C/E_{Asub}{}^X\text{-}Y^X\text{-}C/E_{Dsub}{}^X$ | v. |
| $C_{Asub}{}^X\text{-}Y^X\text{-}C/E_{Dsub}{}^X$ | w. |
| $C/E_{Asub}{}^X\text{-}Y^X\text{-}C_{Dsub}{}^X$ | x. |
| $C^X\text{-}Y^X\text{-}C_{Dsub}{}^X$ | y. |
| $C/E^X\text{-}Y^X\text{-}C_{Dsub}{}^X$ | z. |
| $C^X\text{-}Y^X\text{-}C/E_{Dsub}{}^X$ | aa. |
| $C/E^X\text{-}Y^X\text{-}C/E_{Dsub}{}^X$ | bb. |
| $C_{Asub}{}^X\text{-}Y^X\text{-}C^X$ | cc. |
| $C/E_{Asub}{}^X\text{-}Y^X\text{-}C/E^X$ | dd. |
| $C_{Asub}{}^X\text{-}Y^X\text{-}C/E^X$ | ee. |
| $C/E_{Asub}{}^X\text{-}Y^X\text{-}C^X$ | ff. |
| $C_{start}\text{-}Y^X\text{-}C_{Dsub}{}^X$, | gg. |
| $C_{start}\text{-}Y^X\text{-}C/E_{Dsub}{}^X$ | hh. |
| $Y^X\text{-}C_{Dsub}{}^X$ | ii. |
| $Y^X\text{-}C/E_{Dsub}{}^X$ | jj. |
| $C_{Asub}{}^X\text{-}Y^X\text{-}TE$ | kk. |
| $C/E_{Asub}{}^X\text{-}Y^X\text{-}TE$ | ll. |
| $C_{Asub}{}^X\text{-}Y^X\text{-}C_{term}$ | mm. |
| $C/E_{Asub}{}^X\text{-}Y^X\text{-}C_{term}$ | nn. | wherein $C_{Asub}{}^X$ or $C/E_{Asub}{}^X$ are $C_{Asub}$ or $C/E_{Asub}$ have the amino acid specificity X, and X is a specificity to one or more amino acid species for example to amino acids X1-Xn, $Y^X$ represents one or a sequential series of any NRPS or PKS domains or modules (e.g. A, T, E, C, MT, A-MT, Cy) having the amino acid specificity X, $A^X$ are adenylation domains having the amino acid specificity X, C or C/E are C or C/E having the amino acid specificity X, $C_{Dsub}{}^X$ or $C/E_{Dsub}{}^X$ are $D_{Dsub}$ or a $C/E_{Dsub}$ have the amino acid specificity X, and TE are thioesterase domains and $C_{term}$ are terminal Condensation domains, both relevant for NRPS regeneration.

In some embodiments of the invention an $XU_{2.0}$ of a system of the invention may include domains with promiscuous amino acid specificity.

In some embodiments of the invention an $XU_{2.0}$ of a system of the invention may include domains with different amino acid specificity. Hence, the amino acid specificity of the partial C or C/E subdomains may differ from another and/or from the A domain of the same unit. However, it is generally preferred that an $XU_{2.0}$ of the invention comprises domains and modules with identical or at least overlapping amino acid specificities X. Of course this does not exclude, to the contrary this is intended according to the invention, that the system includes multiple $XU_{2.0}$ having different amino acid specificities X in order assemble a non ribosomal peptide with different amino acid residues.

The domain abbreviations are defined above. For the contest of the present invention the index $_{Dsub}$ shall refer to a C or C/E donor subdomain, and $_{Asub}$ shall refer to a C or C/E acceptor subdomain. The X shall denote the amino acid specificity of the respective domain.

In this context it is noted than X may be selected from any natural or non-natural occurring amino acid. Also within the system, each unit in the system may have a different given amino acid X, or a given amino acid X which is identical with one or more other exchange units in the system.

In other embodiments each single $XU_{2.0}$ preferably does not comprise a functionally assembled condensation (C)- or condensation/epimerization (C/E)-domain. Using the system of the invention, only the assembly of two individual $XU_{2.0}$ will result in a functional C or C/E domain.

In other embodiments the system preferably includes at least two $XU_{2.0}$, when connected to each other, form a functional assembled C or C/E domain composed of one partial C or C/E domain of the first $XU_{2.0}$ and one partial C or C/E domain of the second $XU_{2.0}$. Preferably the partial domains of the first and the second $XU_{2.0}$ are different in kind, in other words, are preferably either a donor or an acceptor domain.

Yet another preferred embodiment of the invention provides a system, comprising at least two $XU_{2.0}$ of which each has specificity for a different amino acid X, preferably wherein each X is selected from any natural or non-natural amino acid.

In accordance with the present invention the amino acid X is selected from a proteinogenic amino acid, a non-proteinogenic amino acid, a D- or L-amino acid, or a non-standard amino acid, or combinations thereof.

Furthermore, the invention provides in some embodiments a system further comprising a $XU_{2.0}$ termination and/or initiation unit, wherein the $XU_{2.0}$ initiation unit comprises only a C or C/E domain donor subdomain, a domain structure $C-A^X-T-C_{Dsub}{}^X$ or $C-A^X-T-C/E_{Dsub}{}^X$, specific for the incorporation of acyl units (fatty acids and their derivatives) as starting units, and wherein the termination module comprises any one of a terminal condensation domain ($C_{term}$), an internal condensation (C) domain, an internal condensation and epimerization (C/E)-didomain, a cyclization (Cy) domain, an epimerization (E) domain, a reduction (Re), an oxidation (Ox) or a thioesterase (TE) domain.

For example, in some embodiments the system preferably comprises an $XU_{2.0}$ initiation unit having any one of the following formulas:

$C_{Asub}-A^X-T-C_{Dsub}{}^X$, $C/E_{Asub}-A^X-T-C_{Dsub}{}^X$, $C_{Asub}-A^X-T-C/E_{Dsub}{}^X$, $C/E_{Asub}-A^X-T-C/E_{Dsub}{}^X$, or $C_{start}-A^X-T-C_{Dsub}{}^X$, $A^X-T-C_{Dsub}{}^X$, $C_{start}-A^X-T-C/E_{Dsub}{}^X$, or $A^X-T-C/E_{Dsub}{}^X$, where instead of a $C_{Asub}$ or a $C/E_{Asub}$ domain also a complete $C_{start}$ or C or no C domain of any kind may be present.

The system of the invention preferably has at least two, preferably three, four, or more, $XU_{2.0}$ when put into sequence provide the NRPS. The number of units is not in any way limited and will dependent on the intended complexity of the system or on the peptides to be produced. Systems may include at least 2, 5, 10, 20, 30, 40, 50, 100, 500, or more units. And the units may have identical or different amino acid specificities X.

Any two $XU_{2.0}$ of the present invention can be assembled at the loop region between the C- or C/E-domain donor and acceptor sites. The loop region is the region in a C or C/E domain which connects the two halves of the pseudo dimer structure of the C or C/E domain (Keating et al. 2002, Samel et al. 2007, Tanovic et al. 2008, Bloudoff et al. 2013). Preferably the loop region is between amino acid 261 and 271—according to the nomenclature of the crystal structure of the TycC5-6 T-C didomain (PDB-ID: 2JGP)—for a C or C/E domain.

In some additional embodiments the system of the invention may include at least one $XU_{2.0}$ having a modification domain, such as an E, MT or Ox or other modification domain.

The system of the invention in some embodiments may be a system, wherein each $XU_{2.0}$ is encoded by a sequence of nucleic acids. The system is therefore a system of nucleic acid constructs. In other embodiments, the system is a system of a sequence of amino acids or proteins, such as NRPS.

Further preferred is a system comprising for each amino acid X each of the following $XU_{2.0}$ of the formula: $C_{Asub}{}^X-A^X-T-C_{Dsub}{}^X$, $C/E_{Asub}{}^X-A^X-T-C/E_{Dsub}{}^X$, $C_{Asub}{}^X-A^X-T-C/E_{Dsub}{}^X$, $C/E_{Asub}{}^X-A^X-T-C_{Dsub}{}^X$.

The system according to the invention may comprise said $XU_{2.0}$ for two or more amino acids X, preferably for a multitude of amino acids, preferably wherein the system comprises for each natural amino acid one of $C_{Asub}{}^X-A^X-T-C_{Dsub}{}^X$, $C/E_{Asub}{}^X-A^X-T-C/E_{Dsub}{}^X$, $C_{Asub}{}^X-A^X-T-C/E_{Dsub}{}^X$, and $C/E_{Asub}{}^X-A^X-T-C_{Dsub}{}^X$.

In another aspect of the invention a method for the production of peptides is provided comprising a step of expressing or assembling a NRPS assembled with a system according to the present invention.

In another aspect of the invention a library of nucleic acid molecules is provided, wherein the library comprises at least two or more nucleic acid constructs each encoding an $XU_{2.0}$, and each having the same or different amino acid specificities and wherein the $XU_{2.0}$ comprises at least one partial condensation (C)- or partial condensation/epimerization (C/E)-domain selected from the group consisting of a condensation-domain acceptor site subdomain ($C_{Asub}$) having an amino acid specificity X, a condensation/epimerization-domain acceptor site subdomain ($C/E_{Asub}$) having an amino acid specificity X, a condensation-domain donor site subdomain ($C_{Dsub}$) having an amino acid specificity X and a condensation/epimerization-domain donor site subdomain ($C/E_{Dsub}$) having an amino acid specificity X. Said $XU_{2.0}$ may in some embodiments not comprise a fully assembled C or C/E domain.

The library of the invention may comprise nucleic acid constructs encoding at least one $XU_{2.0}$ termination and/or initiation unit, wherein the $XU_{2.0}$ initiation unit comprises only a C or C/E domain donor subdomain, a domain structure $C-A^X-T-C_{Dsub}{}^X$ or $C-A^X-T-C/E_{Dsub}{}^X$, specific for the incorporation of acyl units (fatty acids and their derivatives) as starting units, and wherein the termination module comprises any one of a terminal condensation domain (Cterm), an internal condensation (C) domain, an internal condensation and epimerization (C/E)-didomain, a cyclization (Cy) domain, an epimerization (E) domain, a reduction (R), an oxidation (Ox) or a thioesterase (TE) domain The library of the invention may be preferred, wherein each $XU_{2.0}$ is encoded by a separate nucleic acid construct. Preferably the library comprises the $XU_{2.0}$ of the system described herein before.

A method for producing a NRPS, the method comprising a step of assembling at least two NRPS eXchange Units ($XU_{2.0}$) each specific for a different or identical amino acid X, and wherein the $XU_{2.0}$ comprises at least one partial condensation (C)- or partial condensation/epimerization (C/E)-domain selected from the group consisting of a condensation-domain acceptor site subdomain ($C_{Asub}$) specific for a given amino acid X, a condensation/epimerization-domain acceptor site subdomain ($C/E_{Asub}$) specific for a given amino acid X, a condensation-domain donor site subdomain ($C_{Dsub}$) specific for a given amino acid X and a condensation/epimerization-domain donor site subdomain ($C/E_{Dsub}$) specific for a given amino acid X; wherein said $XU_{2.0}$ does not comprise a fully assembled C or C/E domain. Preferably the NRPS is assembled out of the nucleic acid constructs of the library of the invention, and expression of said NRPS.

In addition there is provided a method for the production of non-ribosomal peptides having a specific sequence, the method comprising assembling a NRPS according to the method for producing a NRPS of the invention, wherein the NRPS is composed of a sequence of $XU_{2.0}$ having specificity according to the peptide to be produced.

A further aspect of the invention then provides a biological cell comprising a nucleic acid construct as described before in context of the library of the invention Therefore, the invention may also provide as one aspect a library of biological cells (strains), wherein each biological cell (strain) comprises a nucleic acid construct of the above described library.

The non-ribosomal peptide of the invention may be a linear or a cyclic peptide. When the peptide is cyclic, the NRPS preferably comprises a cyclization domain in the termination module (i.e. thioesterase (TE), reductase (Red), terminal condensation (Cterm) or C/E domain). Non-ribosomal peptides produced according to the descriptions of the invention are preferably non-naturally occurring non-ribosomal peptides.

Another aspect of the invention then pertains to a method for modifying a provided NRPS-encoding sequence, the method comprising the steps of providing a NRPS-encoding sequence, preferably a full length NRPS-encoding sequence such as a wild type or naturally occurring NRPS-encoding sequence, and introducing into said NRPS-encoding sequence a $XU_{2.0}$ as defined by the present invention, to preferably replace and/or complement the respective domains of the provided NRPS with the domains encoded by the $XU_{2.0}$. The replacement is preferably to modify the sequence or structure of the peptide product produced by the NRPS. $XU_{2.0}$ of the invention may be used to introduce additional one or more amino acids, to remove one or more amino acids, to replace one or more amino acids, and/or to change the peptide structure (cyclic or linear peptides). The introduction of the $XU_{2.0}$ of the invention in the method is preferably done by fusing $XU_{2.0}$ fragments encoding a donor or acceptor site of a partial C or C/E domain of the $XU_{2.0}$ to a corresponding end of a donor or acceptor site of the provided NRPS-encoding sequence, to thereby obtain a chimeric C or C/E domain of the introduced $XU_{2.0}$ and the provided NRPS.

The present invention will now be further described in the following examples with reference to the accompanying figures and sequences, nevertheless, without being limited thereto. For the purposes of the present invention, all references as cited herein are incorporated by reference in their entireties. In the Figures:

FIG. 1: Modulation of C-domain substrate specificity. (a) C-domain excised from the T-C bidomain TycC 5-6 from tyrocidine syntethase (TycC) of *Brevibacillus brevis* (PDB-ID: 2JGP) with N-terminal (yellow) and C-terminal (blue) subdomains depicted in ribbon representation (top). Boxed: enlarged representation of the $C_{Dsub}$-$C_{Asub}$ linker with contributing linker AAs in stick representation and fusion site marked in red. Bottom: sequence logo of $C_{Dsub}$-$C_{Asub}$ linker sequences from *Photorhabdus* and *Xenorhabdus*. (b) Schematic representation of WT GxpS, recombinant NRPS-1 and -2 as well as corresponding peptide yields as obtained from triplicate experiments. For peptide nomenclature the standard one letter AA code with lowercase for D-AA is used. (c) Schematic representation of BicA with modules and eXchange Units (XU and $XU_{2.0}$) highlighted. Specificities are assigned for all A-domains. For domain assignment the following symbols are used: A (large circles), T (rectangle), C (triangle), C/E (diamond), TE (C-terminal small circle).

Figure 2:
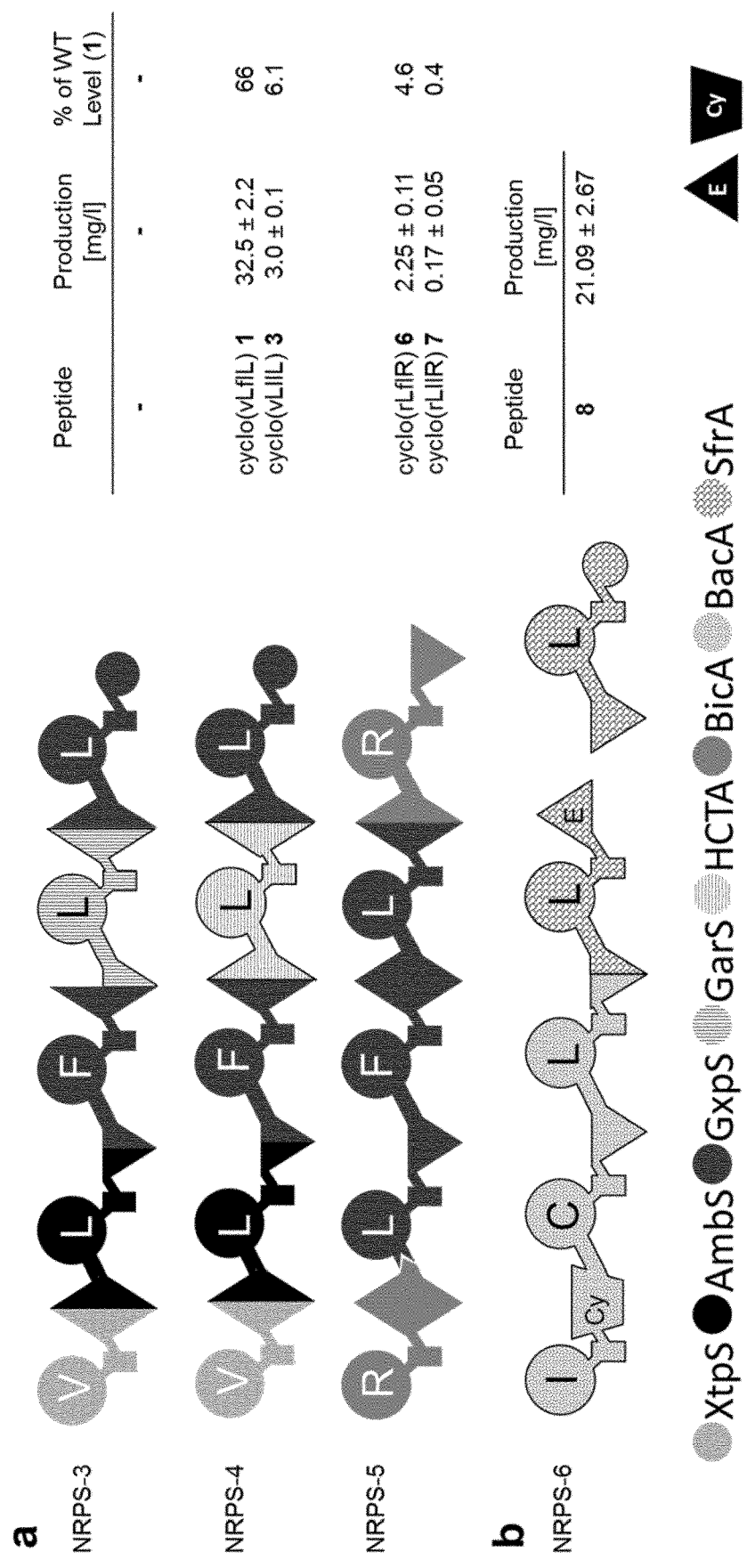

FIG. 2: De novo design of recombinant NRPS for peptide production. (a) Generated recombinant GxpS (NRPS-3-5) and corresponding amounts of GameXPeptide derivatives 1, 3, 6, and 7 as determined in triplicates. (b) Recombinant NRPS-6 synthesizing 8. Building blocks are of Gram-positive origin. Bottom: Color code of NRPS used as building blocks (for details see FIG. 8). For assignment of domain symbols see FIG. 1.

Figure 3:
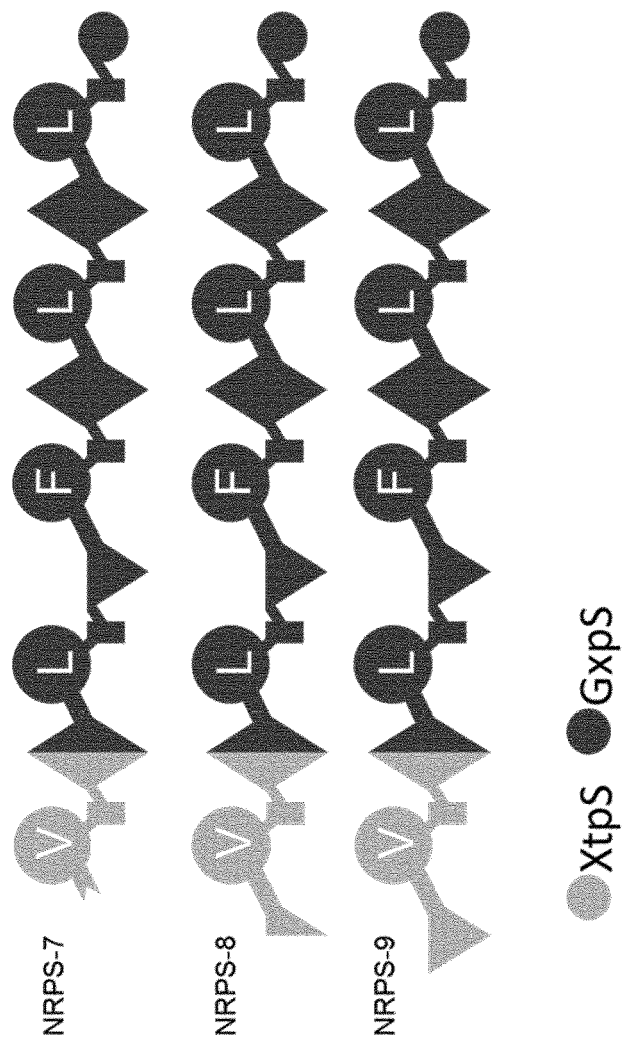

FIG. 3: Exchange of NRPS starter units. Schematic representation of recombinant GxpS (NRPS-7-9) and corresponding peptide yields as obtained from triplicate experiments. For peptide nomenclature the standard one letter AA code with lowercase for D-AA is used. For assignment of domain symbols see FIG. 1. Bottom: Color code of NRPS used as building blocks (for details see FIG. 8).

Figure 4:
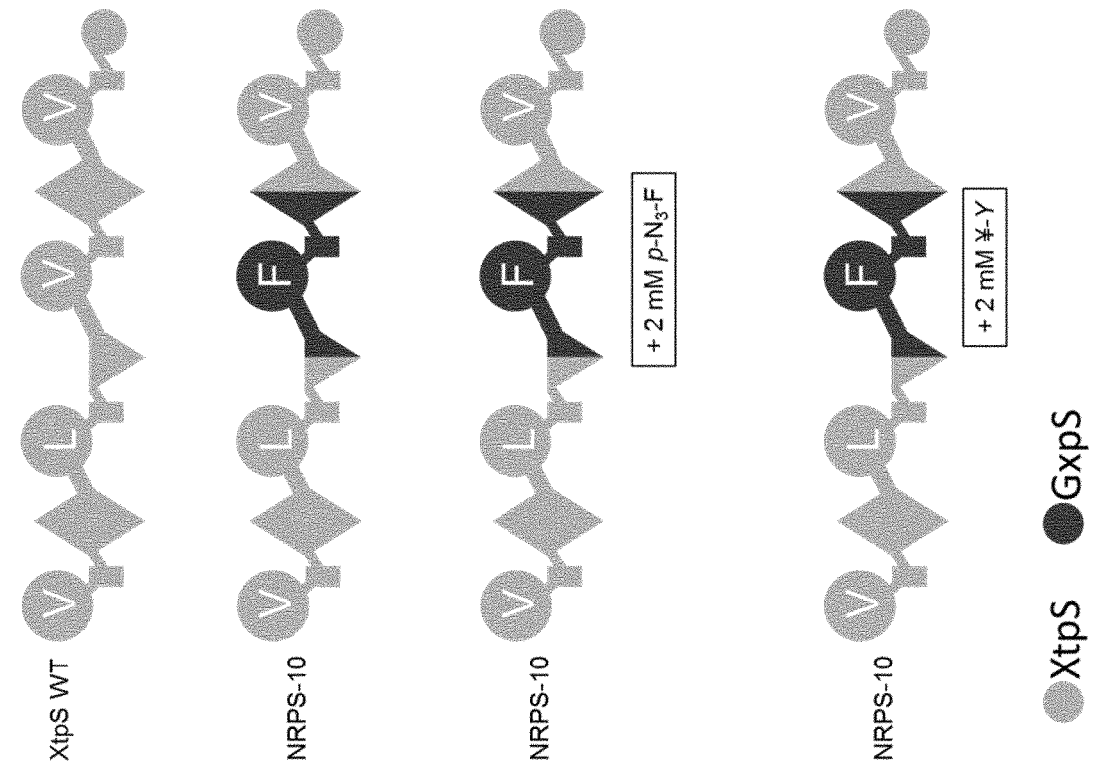

FIG. 4: Creation of functionalized xenotetrapeptide derivatives. Schematic representation of WT XtpS, recombinant NRPS-10 and corresponding peptide yields as obtained from triplicate experiments. For peptide nomenclature the standard one letter AA code with lowercase for D-AA is used. For assignment of domain symbols see FIG. 1. Bottom: Color code of NRPS used as building blocks (for details see FIG. 8).

Figure 5:
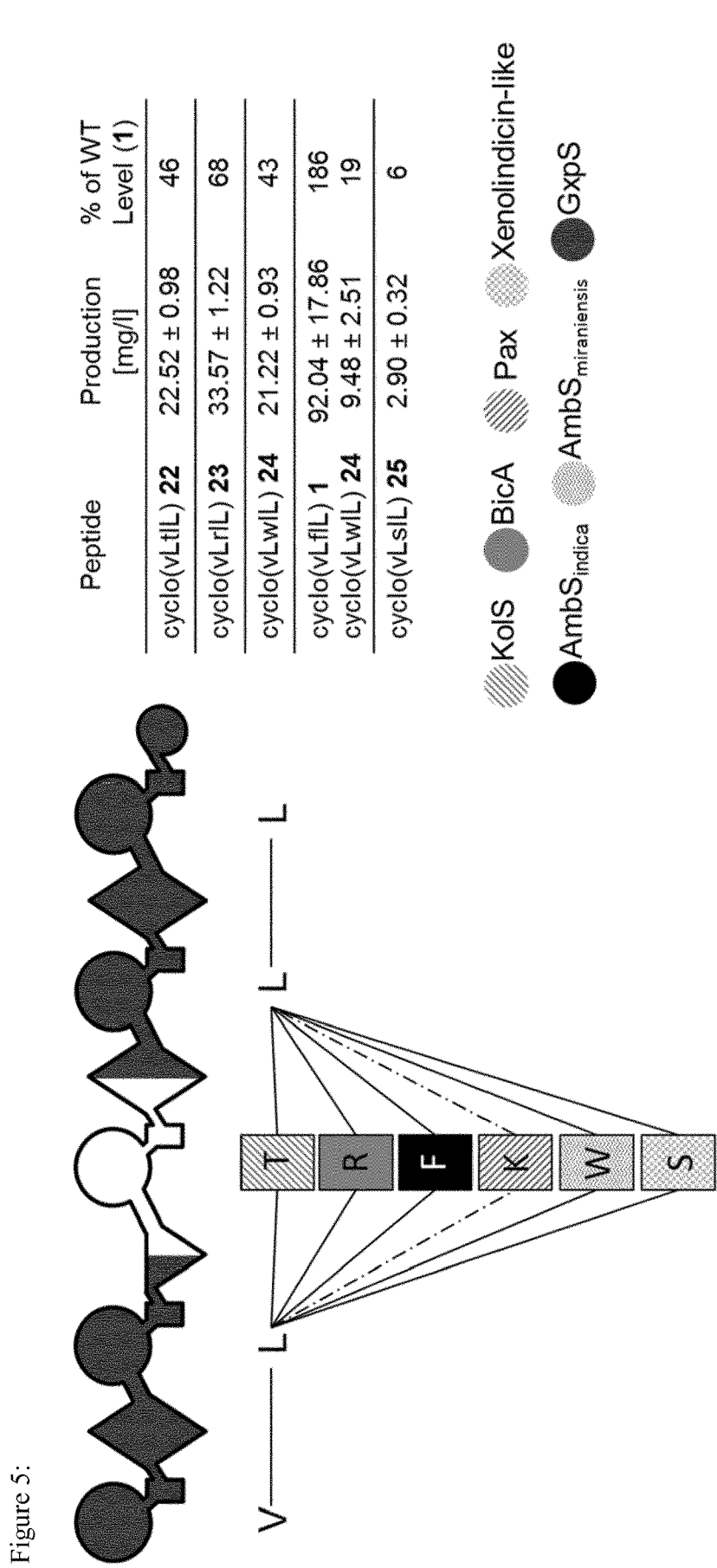

FIG. 5: Targeted randomization of GxpS at position three. Schematic representation of all possible recombinant NRPSs (top left) and corresponding A domain specificity (bottom left). Detected peptides (solid line) and corresponding peptide yields (top right) as obtained from triplicate experiments. Dashed lines indicate not determined GxpS derivatives. For peptide nomenclature the standard one letter AA code with lowercase for D-AA is used. For assignment of domain symbols see FIG. 1. Bottom: Color code of NRPS used as building blocks (for details see FIG. 8).

Figure 6:
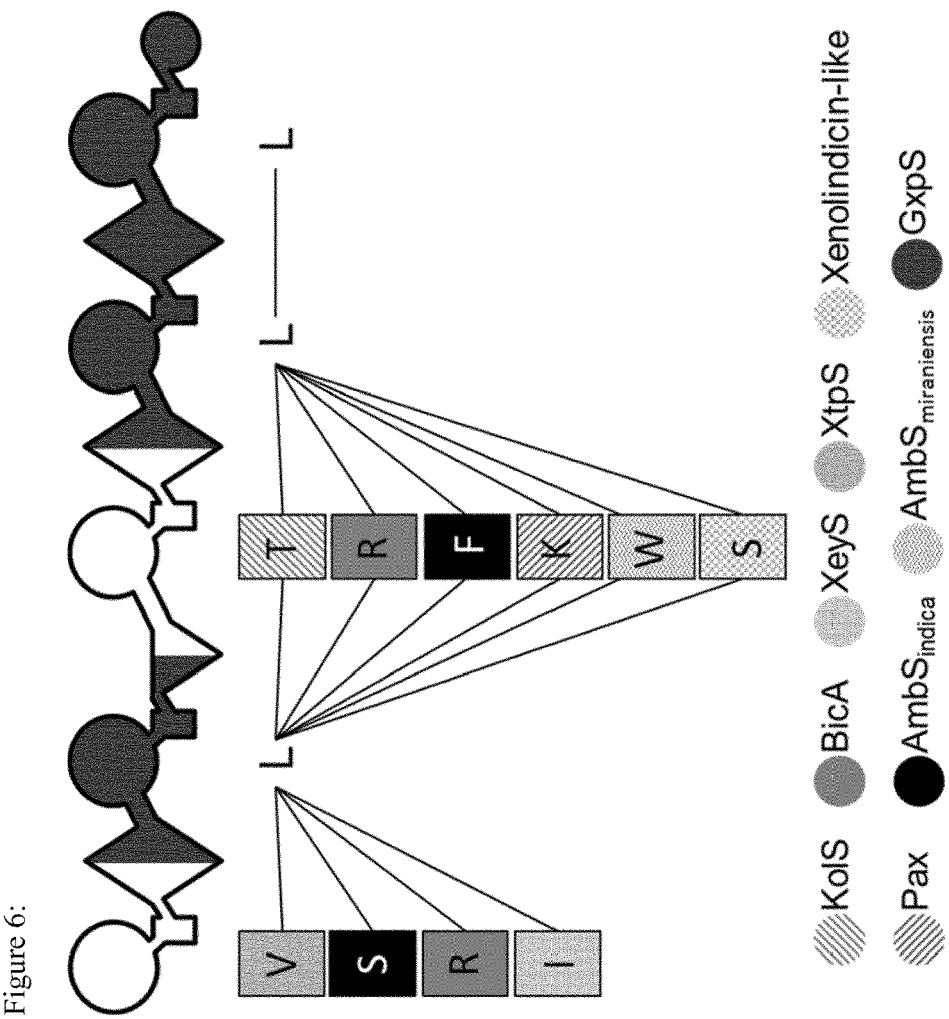

FIG. 6: The creation of a library with randomization of position one and three from GxpS. Schematic representation of all possible recombinant NRPSs (top left) and corresponding A domain specificity (bottom left). Detected peptides and corresponding peptide yields (right) as obtained from triplicate experiments. For peptide nomenclature the standard one letter AA code with lowercase for D-AA is used. For assignment of domain symbols see FIG. 1. Bottom Color code of NRPS used as building blocks (for details see FIG. 8).

Figure 7:
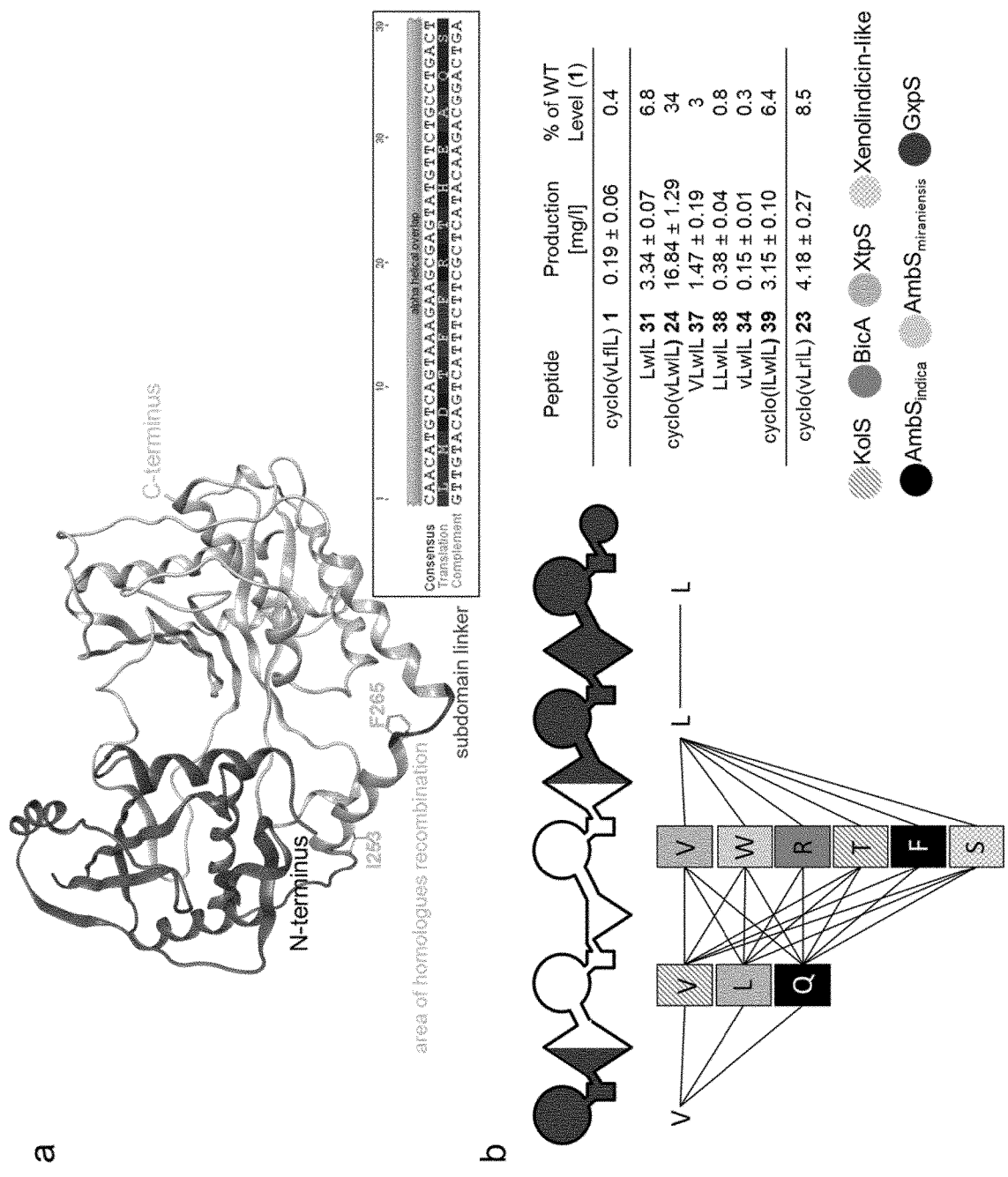

FIG. 7: Randomization of adjacent positions. (a) Crystal structure of TycC6 (PDB-ID: 2JGP), subdivided into N terminal subdomain (grey) and C terminal subdomain (light red). The subdomain linker is highlighted in red and the targeted area (I253-F265) for homologues recombination in yeast is highlighted in green (39 nucleotides). The Consensus sequence used to generate library three is shown bottom right. (b) Schematic representation of all possible recombinant NRPSs (top left) and corresponding A domain specificity (bottom left). Detected peptides and corresponding peptide yields (right) as obtained from triplicate experiments. For peptide nomenclature the standard one letter AA code with lowercase for D-AA is used. For assignment of domain symbols see FIG. 1. Bottom right: Color code of NRPS used as building blocks (for details see FIG. 8).

Figure 8:
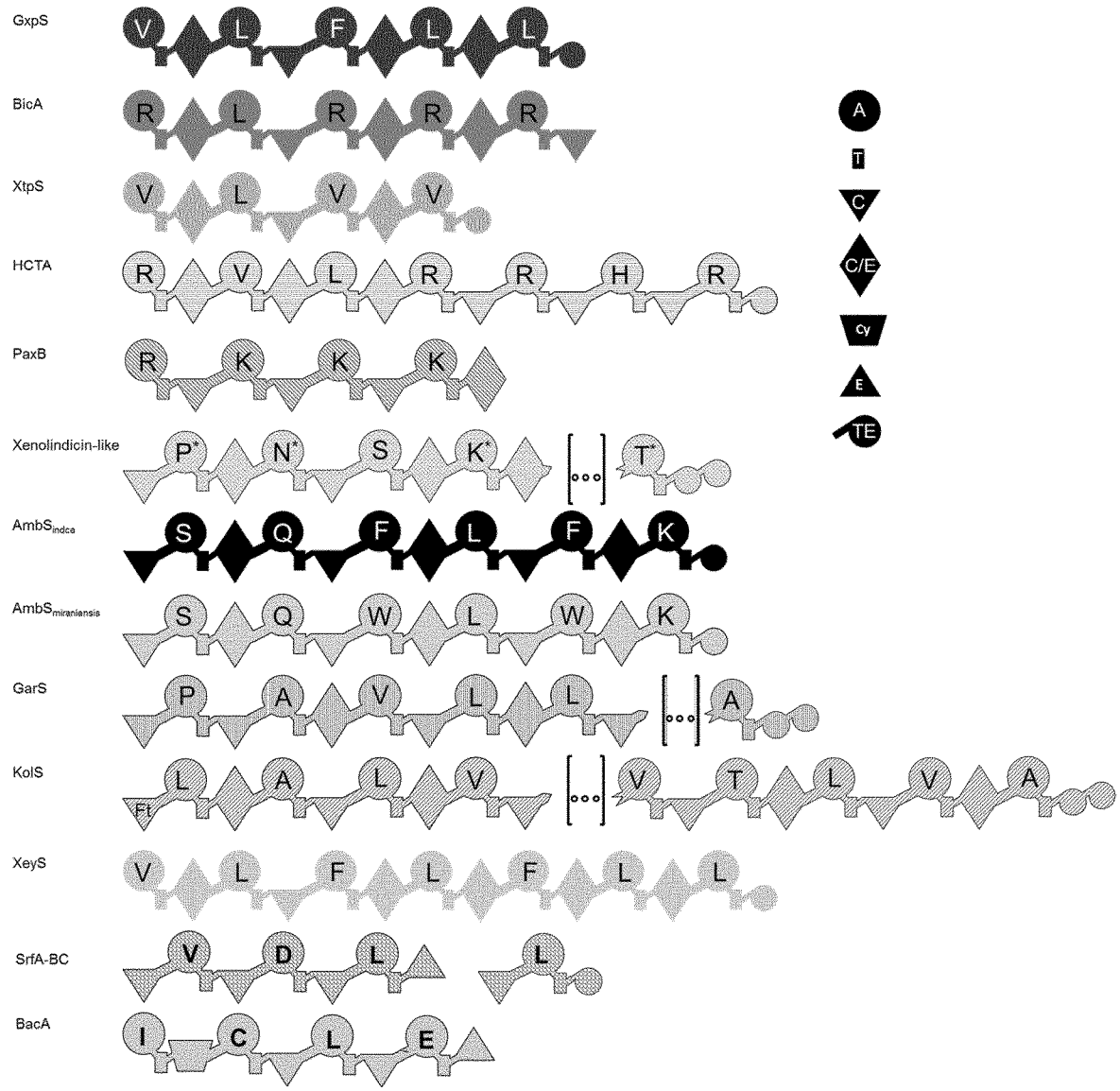

FIG. 8: Schematic overview of all NRPS used in this work. GxpS, BicA, XtpS, HCTA, PaxB, KolS, $AmbS_{mir}$ from *X. miraniensis* and $AmbS_{ind}$ from *X. indica* have been described previously. For GarS producing gargantuanin see Genbank accession number PRJNA224116. For Xenolindicin-like syntethase see Genbank accession number PRJNA328553. For XeyS producing xindeyrin see Genbank accession number PRJNA328572.

EXAMPLES

Example 1: C-Domains Have Acceptor Site Substrate Specificity

To verify the influence of the C-domains acceptor site ($C_{Asub}$) proof reading activity, GameX-Peptide producing NRPS GxpS of *Photorhabdus luminescens* TT01 was chosen as a model system (Bode et al. 2012; Nollmann et al. 2014). A recombinant GxpS was constructed, not complying with the rules of the XU concept (WO 2017/020983). Here, XU2 of GxpS (FIG. 1b, NRPS-1) was exchanged against XU2 of the bicornutin producing NRPS (BicA, FIG. 1c) (Fuchs et al. 2012). Although both XUs are Leu specific, they are differentiated by their $C_{Asub}$ specificities—Phe for XU2 of GxpS and Arg for XU2 of BicA. Therefore, no peptide production was observed as expected. This experiment confirmed previously published scientific results from in vitro experiments (Belshaw et al. 1999, Clugston et al. 2003, Samel et al. 2007, Rausch et al. 2007), and illustrates that C-domains indeed are highly substrate specific at their $C_{Asub}$ (WO 2017/020983).

Example 2: Modulation of C-Domain Substrate Specificity

In developing a new and C-domain specificity independent and/or evading strategy, the inventors strived to determine the structural basis for this purpose by reviewing available structural data of C-domains (Samel et al. 2007, Tanovic et al. 2008). As C-domains have a pseudo-dimer configuration (Keating et al. 2002, Samel et al. 2007, Tanovic et al. 2008, Bloudoff et al. 2013), and the catalytic center, including the HHXXXDG motif, has two binding sites—one for the electrophilic donor substrate and one for the nucleophilic acceptor substrate (Rausch et al. 2007) (FIG. 1a)—the inventors concluded that the four AA long conformationally flexible loop/linker between both subdomains might be the ideal target to reconfigure C-domain specificities, by engineering C-domain hybrids (FIG. 1a). For this purpose the Arg specific $C_{Asub}$ of the GxpS-BicA hybrid NRPS (FIG. 1b, NRPS-1) was re-exchanged to the Leu specific $C_{Asub}$ of GxpS, restoring the functionality of the hybrid NRPS (NRPS-2) and leading to the production of GameXPeptide A-D (1-5) in 217% yield compared to the WT GxpS (FIG. 1b) confirmed by MS/MS analysis and comparison of the retention times.

Example 3: The eXchange Unit 2.0

From above mentioned results in conjunction with bioinformatics analysis, the inventors concluded that C-domains acceptor and donor site ($C_{Dsub}$) mark a self-contained catalytically active unit $C_{Asub}$-A-T-$C_{Dsub}$ ($XU_{2.0}$)—without interfering major domain-domain interfaces/-actions during the NRPS catalytic cycle (Marahiel 2015). In order to validate the proposed $XU_{2.0}$ building block (FIG. 1c) and to compare the production titers with a natural NRPS, the inventors reconstructed GxpS (FIG. 1b) in two variants (FIG. 2, NRPS-3 and -4). Each from five $XU_{2.0}$ building blocks from four different NRPSs (XtpS, AmbS, GxpS, GarS, HCTA) (FIG. 8):

NRPS-3: although leading to a mixed C/$E_{Dsub}$-$C_{Asub}$-domain between $XU_{2.0}$3 and $XU_{2.0}$4 (FIG. 2), $XU_{2.0}$ building blocks from XtpS ($XU_{2.0}$1), AmbS ($XU_{2.0}$4), GxpS ($XU_{2.0}$3 and 5), and GarS ($XU_{2.0}$4) were used, to reveal if C and C/E domains can be combined.

NRPS-4: to prevent any incompatibilities, $XU_{2.0}$3 originated from GarS was replaced by a $XU_{2.0}$3 from HCTA (FIG. 2).

Whereas NRPS-3 (FIG. 2) showed no detectable production of any peptide, NRPS-4 (FIG. 2) resulted in the production of 1 and 3 in 66 and 6% yield compared to the natural GxpS, as confirmed by MS/MS analysis and comparison of the retention times (FIG. 2,). In line with expectations from domain sequences, phylogenetics as well as structural idiosyncrasies of C/E- and C-domains (Rausch et al. 2007), it may be deduced from these results that C/E and C-domains cannot be combined with each other. Although NRPS-4 (FIG. 2) showed moderately reduced production titers, most likely due to the non-natural $C_{Dsub}$-$C_{Asub}$ pseudo-dimer interface, the formal exchange of the non-specific $XU_{2.0}$1 from GxpS (Val/Leu) against the Val-specific $XU_{2.0}$1 from XtpS led to exclusive production of 1 and 3 without production of 2 and 4 (FIG. 2), indicating that the $XU_{2.0}$ can also be used for increasing product specificity and reducing side products (WO 2017/020983).

Additional GameXPeptide derivatives were generated (FIG. 2a, NRPS-5) by combining building blocks according to the definition of XU and $XU_{2.0}$ (WO 2017/020983). Three fragments (1: C1-A1-T1-C/E2 of BicA; 2: A2-T2-C3-A3-T3-C/E4-A4-T4-C/$E_{Dsub}$5 of GxpS; 3: C/$E_{Asub}$5-A5-T5-$C_{term}$ of BicA) from two NRPSs (BicA: Xenorhabdus budapestensis DSM 16342; GxpS: Photorhabdus luminescens TT01) were used as construction material (Bode et al. 2012, Fuchs et al. 2012). The expected two Arg containing cyclic pentapeptides 6 and 7 were produced in yields of 2.25 and 0.17 mg/L and were structurally confirmed by chemical synthesis. Both peptides only differ in Leu or Phe at position three from the relaxed substrate specificity of $XU_{2.0}$3 from GxpS. Despite a drop of production rate in comparison to the WT NRPS, the inventors successfully demonstrated that the recently published XU (WO 2017/020983) as well as the novel $XU_{2.0}$ reliably broaden the possibilities of successfully reprogramming NRPS and to heterologously synthesize tailor-made peptides.

To show the general applicability of the novel $XU_{2.0}$ building block an artificial NRPS was designed de novo from building blocks of Gram-positive origin (NRPS for the production of bacitracin (Konz et al. 1998) from Bacillus licheniformis ATCC 10716 and surfactin (Cosmina et al. 1993) from Bacillus subtilis MR 168), since all aforementioned recombined NRPS are of Gram-negative origin. The expected pentapeptide (8) containing the bacitracin NRPS derived thiazoline ring was produced in yields of 21.09 mg/L (FIG. 2b), showing the universal nature of the $XU_{2.0}$.

Example 4: Amending the Starter Unit

Up to date there is no publication describing the successful exchange of a starter unit against an internal module NRPS-fragment. However, possible identified problems which would need to be solved for example are: (I) as starter-A-domains in general comprise some kind of upstream sequence of variable length with unknown function and structure, it is difficult to define an appropriate artificial leader sequence, and (II) necessary interactions at the C-A interface may be important for adenylation activity and A-domain stability, like indicated by recently published studies (Li et al. 2016, Meyer et al. 2016). Therefore, the first step in order to approach the concrete problem three recombinant GxpS constructs (NRPS-7-9) with internal domains as starting units were created (FIG. 3):

NRPS-7: as all starter A-domains have at least a preceding C-A linker sequence A1-T1-$C_{Dsub}$2 of GxpS was exchanged against C2A3-linker-A3-T3-$C_{Dsub}$4 of XtpS;

NRPS-8: as there are several examples of NRPS carrying parts of a C-domain (e.g. BicA) in front of the starter A-domain A1-T1-$C_{Dsub}$2 of GxpS was exchanged against $C_{Asub}$-A3-T3-$C_{Dsub}$4 of Xtps;

NRPS-9: as there are biosynthetic templates available, exhibiting catalytically inactive starter C-domains (e.g. AmbS), A1-T1-$C_{Dsub}$2 of GxpS was altered to C3-A3-T3-$C_{Dsub}$4 of XtpS.

Whereas NRPS-7 (FIG. 3) did not show production of the desired peptides, NRPS-8 synthesized 1-3 in yields of 0.35 and 0.44 mg/L, and NRPS-9 produced 1 in yields of 0.31 and 0.34 mg/L, as confirmed by MS/MS analysis and comparison of the retention times (FIG. 3). Obtained results revealed that internal A-domains can be used as starter domains, if the upstream $C_{Asub}$ or C-domain is kept in front of the A-domain—indicating the importance of a functional C-A interface for A-domain activity. Yet, from drop in production titers, further questions arise that must be answered by future work. One reason for decreased synthesis rates might be for example the observed codon usage and the lowered GC-content at the beginning of WT NRPS encoding genes, which can have a major impact on transcriptional and/or translational efficiency in conjunction with protein folding issues.

Example 5: The Creation of Functionalized Peptides

Besides simply creating NRP derivatives, one useful application of NRPS reprogramming is the incorporation of AAs that contain alkyne or azide groups into peptides, allowing reactions like Cu(I)-catalyzed or strain-promoted Huisgen cyclization—also known as "click" reactions (Sletten & Bertozzi 2009; Kolb & Sharpless 2003). Yet, although NPRS and A domains have been examined exhaustively for several years, no general method for the simple functionalization of NRPs has emerged.

A broad range of AAs are accepted by the A3 domain of GxpS resulting in a large diversity of GameXPeptides (Bode et al. 2012, Nollmann et al. 2014). Moreover, by using a $\delta$-$^{18}O_4$-ATP pyrophosphate exchange assay for adenylation activity (Phelan et al. 2009, Kronenwerth et al. 2014) and adding substituted AAs to growing E. coli cultures expressing GxpS, the respective A3-domain was identified as being able to activate (in vitro) and incorporate (in vivo 10) several ortho- (o), meta- (m) and para- (p) substituted phenylalanine derivatives, including 4-azido-L-phenylalanine (p-$N_3$-Phe) and O-propargyl-L-tyrosine (Y-Tyr).

In order to create functionalized NRPs the Val specific $XU_{2.0}$3 of the xenotetrapeptide (Kegler et al. 2014) (9) producing NRPS (XtpS) from X. nematophila HGB081 was exchanged against $XU_{2.0}$3 of GxpS, resulting in the production of six new xenotetrapeptide derivatives (10-15) in yields of 0.17-106 mg/L (FIG. 4). After adding p-$N_3$-Phe and Y-Tyr to growing E. coli cultures expressing recombinant XtpS (NRPS-10), six functionalized peptides (16-21) have been identified in yields of 5-228 mg/L. Compounds 17, 8 and 19 were structurally confirmed by chemical synthesis. Due to the relaxed substrate specificity of the introduced A3-domain, compounds 9-21 differ at position three. Moreover, although the A4-domain of XtpS shows an exclusive specificity for Val in the WT NRPS, peptides 11, 13, 16 and 21 produced by NRPS-10 additionally differ in Val or Leu at position four. The observed specificity shift might be due to the hybrid C/E4-domain upstream of A4 from NRPS-10. Leu is the original substrate downstream of the introduced $XU_{2.0}$3 of GxpS (FIG. 1b) in its natural context, indicating that the overall structure of C-domain's along with resulting transformed C-A interface interactions might have some kind of influence to A-domain's substrate specificity. Recently, similar but in vitro observed effects were reported regarding A-domains from sulfazecin (Li et al. 2016) and microcystin (Meyer et al. 2016). This effect could also be used to increase the specificity of A-domains to prevent the formation of side products. Further investigations will shed light on this remarkable and yet unreported effect.

Example 6: The Biotechnological Creation of Natural Product Like Peptide Libraries To address the issue of biologically relevant chemical space the modern drug-discovery approach applies screening libraries based on NPs (Harvey et al. 2015). NP collections exhibit a wide range of pharmacophores, a broad range of stereochemistry and have the property of metabolite-likeness providing a high degree of bioavailability. Yet, the NP discovery process is as expansive as time consuming (Lefevre et al. 2008). Consequently, for bioactivity screenings the random recombination of certain NRPS fragments would be a powerful means to create focused artificial NP-like libraries. The definition of $XU_{2.0}$ building blocks, including the targeted and automated reprograming of C-domain specificities, brought this goal within grasp.

For an initial approach, GxpS was chosen for the generation of a focused peptide library created via a one-shot yeast based TAR cloning approach (Schimming et al. 2014, Gietz et al. 2007). Here, the third position of the peptide (D-Phe) was randomized (FIG. 5) using six unique $XU_{2.0}$ building blocks from six NRPS (KolS (Bode et al. 2015), $AmbS_{mir}$ (Schimming et al. 2014), Pax (Fuchs et al. 2011), $AmbS_{ind}$, XllS; for detail see FIG. 8), resulting in the production of 1 and four new GameXPeptide derivatives (22-25) in yields of 3-92 mg/L that were structurally confirmed by chemical synthesis.

For the generation of a second and structurally more diverse library, positions 1 (D-Val) and 3 (D-Phe) of GxpS were selected in parallel for randomization (FIG. 6). From the experimental setup theoretically 48 different cyclic and linear peptides could have been expected. Screening of 50 E. coli clones resulted in the identification of 18 unique cyclic and linear peptides (1, 4, 11, 13, 24, 26-36) differing in length and AA composition. Since only 7 out of 18 identified peptides belong to the expected set of peptides, homologues recombination in yeast based reprogramming of NRPS also allows the production of unexpected peptides due to unexpected homologues recombination events resulting in an additional layer of peptide diversification, as recorded in previous experiments (WO 2017/020983).

Randomizing adjacent positions via a one shot yeast based TAR cloning approach assumes a standardized nucleotide sequence (40-80 base pairs) for homologues recombination. (Schimming et al. 2014, Gietz et al. 2007). By exploring the T-C didomain crystal structure of TycC5-6 (PDB-ID: 2JGP), the helix $\alpha$5 (I253-F265) next to the C-domain's pseudo-dimer linker was identified as an ideal target for homologues recombination. Following, an artificial $\alpha$5 helix was designed to randomize position 2 (L-Leu) and 3 (D-Phe) of GxpS, being an integral part of all resulting recombinant C3 domains—connecting $XU_{2.0}$2 and 3. The applied as helix was defined as the consensus sequence of all involved $XU_{2.0}$ building blocks (FIG. 7a). Screening of 25 E. coli clones revealed the synthesis of 7 cyclic and linear GameXPeptides (1, 23, 38-42), showing the general applicability of redesigning $\alpha$5 with respect to randomly reprogramming biosynthetic templates (FIG. 7b).

Very recently the concept of XU was published, enabling the guided reprogramming of NRPS for the first time (WO 2017/020983). Nevertheless, the inventors attempted to develop a more user-friendly and straightforward way to achieve the de novo design of NRPS from scratch. The novel $XU_{2.0}$ building block presented here brings crucial advantages compared with all other up to now published strategies (Win et al. 2015, Calcott & Ackerley 2014). In comparison to the state-of-the-art XU concept, the $XU_{2.0}$ enables reprogramming of NRPSs by solely altering one unit since the $XU_{2.0}$ automatically modulates C-domain specificities. Moreover, much less building blocks are required to introduce any changes into the appropriate biosynthetic template. For example, to create any peptide based on the 20 proteinogenic AAs only 80 $XU_{2.0}$ building blocks are necessary—only four of each: $C_{Dsub}$-A-T-$C_{Asub}$, $C_{Dsub}$-A-T-C/$E_{Asub}$, C/$E_{Dsub}$-A-T-C/$E_{Asub}$, and C/$E_{Dsub}$-A-T-$C_{Asub}$. In contrast, 800 XU building blocks would be necessary to generate the same spectrum of peptides. Consequently, the introduction of the $XU_{2.0}$ enormously simplifies and broadens the possibilities of biotechnological applications with regard to optimize bioactive agents via NRPS engineering.

In summary the inventors demonstrated how C-domain specificities can be avoided (FIG. 1) and how this knowledge can be applied to flexibly reprogram NRPSs and to functionalize NRPs by incorporating $XU_{2.0}$ building blocks accepting non-natural AAs like p-$N_3$-Phe and Y-Tyr (FIG. 4,). As azides and alkynes readily undergo bioorthogonal click reactions, p-$N_3$-Phe and Y-Tyr incorporating NRPs can be used for further derivatization (Sletten & Bertozzi 2009, Kolb & Sharpless 2003). Consequently, NRPSs able to incorporate clickable AAs into the produced peptides provide a powerful means of isolating, labelling, and modifying biologically active peptides (Kries et al. 2015).

The true strength of the $XU_{2.0}$'s flexibility, however, lay in the ability to generate random NP-like peptide libraries for subsequent bioactivity screenings. The simple randomization of two building blocks from GxpS and subsequent screening of only 50 E. coli clones led to the identification of 19 novel peptides. The possible automation of screening in line with assays for bioactivity, e.g. via intelligent droplet based microfluidics, opens up entirely new opportunities of identifying novel lead compounds in the future. Especially in the area of anti-infective research underlying results might be an issue very important in practice, namely to fight upcoming antimicrobial resistances.

Materials and Methods

Cultivation of Strains

All E. coli, Photorhabdus and Xenorhabdus strains were grown in liquid or solid LB-medium (pH 7.5, 10 g/L tryptone, 5 g/L yeast extract and 5 g/L NaCl). Solid media contained 1.5% (w/v) agar. S. cerevisiae strain CEN.PK 2-1C and derivatives were grown in liquid and solid YPD-medium (10 g/L yeast extract, 20 g/L peptone and 20 g/L glucose). Agar plates contained 1.5% (w/v) agar. Kanamycin (50 µg/ml) and G418 (200 µg/ml) were used as selection markers. E. coli was cultivated at 37° C. all other strains were cultivated at 30° C.

Expression and Cultivation of His-Tagged Proteins

For overproduction and purification of the ~72 Da His-tagged A domain GxpS_A3 5 ml of an overnight culture in LB medium of E. coli BL21 (DE3) cells harboring the corresponding expression plasmid and the TaKaRa chaperone-plasmid pTf16 (TAKARA BIO INC.) were used to inoculate 500 ml of autoinduction medium (464 ml LB medium, 500 µl 1 M $MgSO_4$, 10 ml 50×5052, 25 ml 20×NPS) containing 20 µg/mL chloramphenicol, 50 µg/mL kanamycin and 0.5 mg/ml L-arabinose (Nishihara et al. 2000). The cells were grown at 37° C. up to an $OD_{600}$ of 0.6. Following the cultures were cultivated for additional 48 h at 18° C. The cells were pelleted (10 min, 4,000 rpm, 4° C.) and stored overnight at −20° C. For protein purification the cells were reuspended in binding buffer (500 mM NaCl, 20 mM imidazol, 50 mM HEPES, 10% (w/v) glycerol, pH 8.0). For cell lysis benzonase (Fermentas, 500 U), protease inhibitor (Complete EDTA-free, Roche), 0.1% Triton-X and lysozym (0.5 mg/ml, ~20,000 U/mg, Roth) were added and the cells were incubated rotating for 30 min. After this the cells were placed on ice and lysed by sonication. Subsequently, the lysed cells were centrifuged (25,000 rpm, 45 min, 4° C.). The yielded supernatant was passed through a 0.2 µm filter and loaded with a flow rate of 0.5 ml/min on a 1 ml HisTrap™ HP column (GE Healthcare) equilibrated with binding buffer. Unbound protein was washed off with 10 ml binding buffer. Impurities were washed off with 5 ml 8% elution buffer (500 mM NaCl, 500 mM imidazol, 50 mM HEPES, 10% (w/v) glycerol, pH 8.0). The purified protein of interest was eluted with 39% elution buffer. Following, the purified protein containing fraction was concentrated (Centriprep® Centrifugal Filters Ultacel® YM—50, Merck Millipore) and the buffer was exchanged to 20 mM Tris-HCl (pH 7.5) using a PD-10 column (Sephadex™ G-25 M, GE Healthcare).

Cloning of GxpS_A3

The adenylation domain GxpS_A3 was cloned from Photorhabdus luminescens TT01 genomic nomic DNA by PCR using the pCOLA_Gib_A3 Insert forward and reverse oligonucleotides shown in Tab. 1. The plasmid backbone of pCOLADUET™-1 (Merck/Millipore) was amplified using the DUET_Gib forward and reverse oligonucleotides shown in Tab 1. The ~1,900 bp PCR product was cloned via Gibson Assembly® Cloning Kit (NEB) according to the manufacturers' instructions into pCOLADUET™-1.

γ-$^{18}O_4$-ATP Pyrophosphat Exchange Assay

The γ-$^{18}O_3$-ATP Pyrophosphat Exchange Assay was performed as published previously (Kronenwerth et al. 2014, Phelan et al. 2009). After an incubation period of 90 min at 24° C. the reactions were stopped by the addition of 6 µl 9-aminoacridine in acetone (10 mg/ml) for MALDI-Orbitrap-MS analysis.

MALDI-Orbitrap-MS

Samples were prepared for MALDI-analysis as a 1:1 dilution in 9-aminoacridine in acetone (10 mg/ml) and spotted onto a polished stainless steel target and air-dried. MALDI-Orbitrap-MS analyses were performed with a MALDI LTQ Orbitrap XL (Thermo Fisher Scientific, Inc., Waltham, MA) equipped with a nitrogen laser at 337 nm. The following instrument parameters were used: laser energy, 27 µJ; automatic gain control, on; auto spectrum filter, off; resolution, 30,000; plate motion, survey CPS. Mass spectra were obtained in negative ion mode over a range of 500 to 540 m/z. The mass spectra for ATP-$PP_i$ exchange analysis were acquired by averaging 50 consecutive laser shots. Spectral analysis was conducted using Qual Browser (version 2.0.7; Thermo Fisher Scientific, Inc., Waltham, MA).

Cloning of Biosynthetic Gene Clusters

Genomic DNA of selected *Xenorhabdus* and *Photorhabdus* strains were isolated using the Qiagen Gentra Puregene Yeast/Bact Kit. Polymerase chain reaction (PCR) was performed with oligonucleotides obtained from Eurofins Genomics (Tab. 1). Fragments with homology arms (40-80 bp) were amplified in a two-step PCR program For PCR Phusion High-Fidelity DNA polymerase (Thermo Scientific), Q5 High-Fidelity DNA polymerase (New England BioLabs) and Velocity DNA polymerase (Bioline) were used. Polymerases were used according to the manufacturers' instructions. DNA purification was performed from 1% TAE agarose gel using Invisorb® Spin DNA Extraction Kit (STRATEC Biomedical AG). Plasmid isolation from *E. coli* was done by alkaline lysis.

Overlap Extension PCR-Yeast Homologous Recombination (ExRec)

Transformation of yeast cells was done according to the protocols from Gietz and Schiestl (Gietz et al. 2007). 100-2,000 ng of each fragment was used for transformation. Constructed plasmids were isolated from yeast transformants and transformed in *E. coli* DH10B::mtaA by electroporation. Successfully transformed plasmids were isolated from *E. coli* transformants and verified by restriction digest.

Heterologous Expression of NRPS Templates and LC-MS Analysis

Constructed plasmids were transformed into *E. coli* DH10B::mtaA. Strains were grown overnight in LB medium containing 50 µg/mL kanamycin. 100 µl of an overnight culture were used for inoculation of 10 ml cultures, containing 0.02 mg/ml L-arabinose and 2% (v/v) XAD-16. 50 µg/mL kanamycin were used as selection markers. After incubation for 72 h at 22° C., respectively, the XAD-16 was harvested. One culture volume methanol was added and incubated for 30 min. The organic phase was filtrated and evaporated to dryness under reduced pressure. The extract was diluted in 1 mL methanol and a 1:10 dilution was used for LC-MS analysis as described previously (Fuchs et al. 2013 & 2014). All measurements were carried out by using an Ultimate 3000 LC system (Dionex) coupled to an AmaZonX (Bruker) electron spray ionization mass spectrometer. High-resolution mass spectra were obtained on a Dionex Ultimate 3000 RSLC Coupled to a Bruker micro-TOF-Q II equipped with an ESI Source set to positive ionization mode. The software DataAnalysis 4.3 (Bruker) was used to evaluate the measurements.

Homology-Modelling

The homology-modelling was performed as described previously {Fuchs:2013cv}. For homology modelling, the 1.85 Å crystal structure of PCP-C bidomain TycC 5-6 from tyrocidine syntethase (TycC) of *Brevibacillus brevis* (PDB-ID: 2JGP) were used {Samel:2007eh}. The sequence identity of GxpS_C3 in comparison to TycC 5-6 is 34.8%, respectively. The final models have a root-mean-square deviation (RMSD) of 1.4 Å respectively, in comparison to the template structures.

10. Peptide Quantification

All peptides were quantified using a calibration curve of synthetic 1 (for quantification of 1-4), 5 (for quantification of 5, 34, 35, 37, 38 and 39), 9 (for quantification of 9, 14 and 15), 10 (for quantification of 10, 11, 12, 13, 26, 27, 28, 29, 30, 31 and 36), 17 (for quantification of 16 and 17), 18, 19 (for quantification of 19, 20 and 21), 22, 23, 24 (for quantification of 24 and 39), 25 (for quantification of 25 and 33), and cyclo[RLfIL] (for quantification of 32 and 40) using HPLC/MS measurements as described above. Triplicates of all experiments were measured.

TABLE 1

Oligonucleotides used in this work.

| Plasmid | Oligonucleotide | Sequence (5'→3') | Template | SEQ ID |
|---|---|---|---|---|
| pCO-LA_gx pS_A3 | pCOLA_Gib_A 3 Insert FW | CATCACCATCATCACCACCCTCAACAACCTGTCACGGC | *P. luminescens* TT01 | 1 |
| | pCOLA_Gib_A 3 Insert RV | CAGCCTAGGTTAATTAAGCTGTTAAGTCAGATCAATCAGCGGCAAC | | 2 |
| | DUET_Gib_FW | CAGCTTAATTAACCTAGGCTG | pCO-LADUET-1 | 3 |
| | DUET_Gib_RV | GTGGTGATGATGGTGATG | | 4 |
| pFF1 NRPS_1 | KB-RT-6 | TCATGAACTCGCCAGAACCAGCAGCGGAGCCAGCGGATCCCAGCG CCTCCGCTTCACAATTC | *P. luminescens* TT01 | 5 |
| | KB-RT-7 | TGGAATGCGACCGAAGAACC | | 6 |

TABLE 1-continued

Oligonucleotides used in this work.

| Plasmid | Oligonucleotide | Sequence (5'→3') | Template | SEQ ID |
|---|---|---|---|---|
| | KB-RT-8 | CACATACCTGAGTAGGATACGGTTCTTCGGTCGCATTCCAAGTTTTCAGCAACAACTGGC | X. budapestensis DSM 16342 | 7 |
| | KB-RT-9 | TGTTTTGCCTGCATCGGAACGCACGTTGTTGCTGGAAACGTGGAATACAACGGAAACTGC | | 8 |
| | KB-RT-10 | CGTTTCCAGCAACAACG | P. luminescens TT01 | 9 |
| | KB-RT-11 | TTCTCCATACCCGTTTTTTTGGGCTAACAGGAGGAATTCCATGAAAGATAGCATGGCTAAAAAGG | | 10 |
| pFF1_NRPS_2 | KB-RT-6 | TCATGAACTCGCCAGAACCAGCAGCGGAGCCAGCGGATCCCAGCGCCTCCGCTTCACAATTC | P. luminescens TT01 | 11 |
| | KB-RT-7 | TGGAATGCGACCGAAGAACC | | 12 |
| | KB-RT-15 | AAGCCATTGACGCTGCCAG | X. budapestensis DSM 16342 | 13 |
| | KB-RT-9 | TGTTTTGCCTGCATCGGAACGCACGTTGTTGCTGGAAACGTGGAATACAACGGAAACTGC | | 14 |
| | KB-RT-10 | CGTTTCCAGCAACAACG | P. luminescens TT01 | 15 |
| | KB-RT-11 | TTCTCCATACCCGTTTTTTTGGGCTAACAGGAGGAATTCCATGAAAGATAGCATGGCTAAAAAGG | | 16 |
| | KB-RT-13 | CACATACCTGAGTAGGATACGGTTCTTCGGTCGCATTCCAATTTTCCAGTAATAACTCCCGCTC | P. luminescens TT01 | 17 |
| | KB-RT-14 | TCAATATCCTGATTATGCGGTCTGGCAGCGTCAATGGCTTTCAGGTGAAGGAGTACAGGC | | 18 |
| pFF1_NRPS_3 | AL-GxpS-2-1 | ACTGTTTCTCCATACCCGTTTTTTTGGGCTAACAGGAGGAATTCCATGAAAGATAGCATGGCTAAAAAGG | X. nematophila ATCC 19061 | 19 |
| | AL-GxpS-2-2 | CCCAATCAACATATCGGTAAAAAAGCGAGTATGTTCCATCTGGCTCACCCCCTGGTGGGCC | | 20 |
| | AL-GxpS-2-3 | CCCGTACCTTTCCGTAATCTGGTCGCTCAGGCCCACCAGGGGGTGAGCCAGATGGAACATACTCG | X. miraniensis DSM 17902 | 21 |

TABLE 1-continued

Oligonucleotides used in this work.

| Plasmid | Oligonucleotide | Sequence (5'→3') | Template | SEQ ID |
|---|---|---|---|---|
| | AL-GxpS-2-4 | CGTCCGACGCCAATAATCACTCTGTGCCTGTACTCCTTCACCTGAAAACCACTGGCGTTGCC | | 22 |
| | AL-GxpS-2-5 | TCAGGTGAAGGAGTACAGGCAC | P. luminescens TT01 | 23 |
| | AL-GxpS-2-6 | GACACCCTGCCGAGCC | | 24 |
| | AL-GxpS-2-7 | CCGGTCCCGTTCCGCCATTTAGTGGCACAGGCTCGGCAGGGTGTCCAAGGCGCTGTTCTCACTG | X. bovienii SS2004 | 25 |
| | AL-GxpS-2-8 | CTCAGCCAACATTTCAGTAAAGAAACGGGTATGTTCAGCCTGACTCACGCTCAGGGTCTGGG | | 26 |
| | AL-GxpS-2-9 | AGTCAGGCTGAACATACCCG | P. luminescens TT01 | 27 |
| | AL-GXpS-2-10 | TTTGCTCATGAACTCGCCAGAACCAGCAGCGGAGCCAGCGGATCCCAGCGCCTCCGCTTCAC | | 28 |
| pFF1_NRPS_4 | AL-GxpS-2-1 | ACTGTTTCTCCATACCCGTTTTTTTGGGCTAACAGGAGGAATTCCATGAAAGATAGCATGGCTAAAAAGG | X. nematophila ATCC 19061 | 29 |
| | AL-GXpS-2-2 | CCCAATCAACATATCGGTAAAAAAGCGAGTATGTTCCATCTGGCTCACCCCCTGGTGGGCC | | 30 |
| | AL-GXpS-2-3 | CCCGTACCTTTCCGTAATCTGGTCGCTCAGGCCCACCAGGGGGTGAGCCAGATGGAACATACTCG | X. miraniensis DSM 17902 | 31 |
| | AL-GXpS-2-4 | CGTCCGACGCCAATAATCACTCTGTGCCTGTACTCCTTCACCTGAAAACCACTGGCGTTGCC | | 32 |
| | AL-GxpS-2-5 | TCAGGTGAAGGAGTACAGGCAC | P. luminescens TT01 | 33 |
| | AL-GxpS-2-6 | GACACCCTGCCGAGCC | | 34 |
| | AL-GxpS-2-11 | GCCGGTCCCGTTCCGCCATTTAGTGGCACAGGCTCGGCAGGGTGTCAGTCAGGAAGCCCACACC | X. miraniensis DSM 17902 | 35 |
| | AL-GXpS-2-12 | CTCAGCCAACATTTCAGTAAAGAAACGGGTATGTTCAGCCTGACTCACCCCCAACCGAACC | | 36 |

TABLE 1-continued

Oligonucleotides used in this work.

| Plasmid | Oligonucleotide | Sequence (5'→3') | Template | SEQ ID |
|---|---|---|---|---|
| | AL-GxpS-2-9 | AGTCAGGCTGAACATACCCG | P. luminescens TT01 | 37 |
| | AL-GXpS-2-10 | TTTGCTCATGAACTCGCCAGAACCAGCAGCGGAGCCAGCGGATCCCAGCGCCTCCGCTTCAC | | 38 |
| pFF1_NRPS_5 | ML020 | AGATTAGCGGATCCTACCTGACGCTTTTTATCGCAACTCTCTACTGTTTCTCCATACCCGTTTTTTTGGGCTAACAGGAGGAATTCCATGAAAGATAACATTGCTACAGTG | pFF1_NRPS_0 | 39 |
| | FF_305 | CCAATAATCACTCTGTGCCTG | | 40 |
| | FF_306 | GAACTGGTTGCACTTTACGC | | 41 |
| | FF_307 | CATCCCTAACCGGGACTG | | 42 |
| | FF_308 | CATACCTTGACGGACAGGGCGGCAACCTGCCAGCGCCGGCACCCTTCCGCAATCTGGTAGCGCAGTCCCGGTTAGGGATGAGTCAGGCAGCCCATACC | X. budaPestensis DSM 16342 | 43 |
| | FF_309 | AACAACACCGGTAAACAGTTCTTCACCTTTGCTCATGAACTCGCCAGAACCAGCAGCGGAGCCAGCGGATCCGGCGCGCCCTATTGCTCTGCTGATATCAGAA | | 44 |
| pFF1_NRPS_6 | ML_P1 | GACCAGACAGAACATCACCG | pFF1_gxpS_WT | 45 |
| | ML_P2 | GGCCCAATCCTATACGCC | | 46 |
| | ML_P3 | CTTACCAAGCGCCACAAGG | | 47 |
| | ML_P4 | AGAATCGGAACAACACCGGTAAACAGTTCTTCACCTTTGCTCATGAACTCGCCAGAACCAGCAGCGGAGCCAGCGGATCCCAGCGCCTCCGCTTCA | | 48 |
| | ML_P5 | TCGGTCAGCCCAAACGGTAATGTCGGTTCATCCACTTCTGCCAACATGTCGGTAAAGAATCGGTGATGTTCTGTCTGGTCGACACCCTGCCGAGCC | X. nematophila HGB081 | 49 |
| | ML_P6.1 | ATCCTACCTGACGCTTTTTATCGCAACTCTCTACTGTTTCTCCATACCCGTTTTTTTGGGCTAACAGGAGGAATTCCATGCGGGCAATGGTGAACC | | 50 |
| pFF1_NRPS_7 | ML_P1 | GACCAGACAGAACATCACCG | pFF1_gxpS_WT | 51 |
| | ML_P2 | GGCCCAATCCTATACGCC | | 52 |
| | ML_P3 | CTTACCAAGCGCCACAAGG | | 53 |
| | ML_P4 | AGAATCGGAACAACACCGGTAAACAGTTCTTCACCTTTGCTCATGAACTCGCCAGAACCAGCAGCGGAGCCAGCGGATCCCAGCGCCTCCGCTTCA | | 54 |
| | ML_P5 | TCGGTCAGCCCAAACGGTAATGTCGGTTCATCCACTTCTGCCAACATGTCGGTAAAGAATCGGTGATGTTCTGTCTGGTCGACACCCTGCCGAGCC | X. nematophila HGB081 | 55 |
| | ML_P6.3 | ATCCTACCTGACGCTTTTTATCGCAACTCTCTACTGTTTCTCCATACCCGTTTTTTTGGGCTAACAGGAGGAATTCCATGTCTGATGAAGGCGTGC | | 56 |

TABLE 1-continued

Oligonucleotides used in this work.

| Plasmid | Oligonucleotide | Sequence (5'→3') | Template | SEQ ID |
|---|---|---|---|---|
| pFF1_NRPS_8 | ML_P1 | GACCAGACAGAACATCACCG | pFF1_gxpS_WT | 57 |
| | ML_P2 | GGCCCAATCCTATACGCC | | 58 |
| | ML_P3 | CTTACCAAGCGCCACAAGG | | 59 |
| | ML_P4 | AGAATCGGAACAACACCGGTAAACAGTTCTTCACCTTTGCTCATGAACTCGCCAGAACCAGCAGCGGAGCCAGCGGATCCCAGCGCCTCCGCTTCA | | 60 |
| | ML_P5 | TCGGTCAGCCCAAACGGTAATGTCGGTTCATCCACTTCTGCCAACATGTCGGTAAAGAATCGGTGATGTTCTGTCTGGTCGACACCCTGCCGAGCC | X. nematophila HGB081 | 61 |
| | ML_P6.2 | ATCCTACCTGACGCTTTTTATCGCAACTCTCTACTGTTTCTCCATACCCGTTTTTTTGGGCTAACAGGAGGAATTCCATGGCATTTACCGAAAAGATCTGCG | | 62 |
| pFF1_NRPS_9 | ML_P7 | CGGATCCTACCTGACGCTTTTTATCGCAACTCTCTACTGTTTCTCCATACCCGTTTTTTTGGGCTAACAGGAGGAATTCCATGAAAGATAGCATGGCTAAAAAGGG | X. nematophila HGB081 | 63 |
| | ML_P8 | CTATCGGCAATTCAAGTAACACCGGTGCATCTGCCAACGTCCGACGCCAATAATCACTCTGTGCCTGTACTCCTTCACCTGAAAATACCTGCCGCTGCC | | 64 |
| | ML_P9 | GCTTGTCTGAATCAACAACCTGATCCGCTGCCGCCATTGACCATTCAATATCCTGATTATGCTGCCTGGCAGCGGCAGGTATTTTCAGGTGAAGGAGTACAGGC | | 65 |
| | ML_P10 | GCACTTCCGACAATCCAAATGACAACGTTGGCTCATCTACCTCAGCCAACATATCGGTAAAGAAACGGGTATGTTCTGCCTGACTGACACCCTGCCGAGCC | | 66 |
| | ML_P11 | GGCTTGCCTCTTGGGGCAAATGGATAGCCTGCCTGCGCCGGTCCCGTTCCGCCATTTAGTGGCACAGGCTCGGCAGGGTGTCAGTCAGGCAGAACATACCCG | X. nematophila HGB081 | 67 |
| | ML_P12 | CCAGAATCGGAACAACACCGGTAAACAGTTCTTCACCTTTGCTCATGAACTCGCCAGAACCAGCAGCGGAGCCAGCGGATCCCAGCGCCTCCACTTCG | | 68 |
| pFF1_library_1 | KB-AmbF-1 | ACCATTCAATATCCTGATTATGCGGCTTGGCAGCGGCAGGTATTTTCGGTTGAACGCTTACAATCC | X. miraniensis DSM 17902 | 69 |
| | KB-AmbF-2 | CTCAGCCAACATGTCAGTAAAGAAGCGAGTATGTTCTGCCTGACTGATACCCAGCCGGGCTTG | | 70 |
| | KB-AmbW-1 | ACCATTCAATATCCTGATTATGCGGCTTGGCAGCGGCAGGTATTTTCATCGGAACGGGTACAAATTC | X. indica DSM 17382 | 71 |
| | KB-AmbW-2 | CTCAGCCAACATGTCAGTAAAGAAGCGAGTATGTTCTGCCTGACTTACCCCCATCCGTGCCTG | | 72 |
| | KB-Thr1 | ACCATTCAATATCCTGATTATGCGGCTTGGCAGCGGCAGGTATTTTCGGCAGCACAGATACAGTCTC | P. luminescens TT01 | 73 |

TABLE 1-continued

Oligonucleotides used in this work.

| Plasmid | Oligonucleotide | Sequence (5'→3') | Template | SEQ ID |
|---|---|---|---|---|
| | KB-Thr2 | CTCAGCCAACATGTCAGTAAAGAAGCGAGTATGTTCTGCCTGACTCACGCCCAACCGGACC | | 74 |
| | KB-Arg1 | ACCATTCAATATCCTGATTATGCGGCTTGGCAGCGGCAGGTATTTTCTGCTGATCGTATTCAGGTGCAG | *X. budapestensis* DSM 16342 | 75 |
| | KB-Arg2 | CTCAGCCAACATGTCAGTAAAGAAGCGAGTATGTTCTGCCTGACTCACGCCCAACCGGACC | | 76 |
| | KB-Ser1 | GTCTAAATCAACAGCCAGATCCGTTGTTGCCATTGACCATTCAATATCCTGATTATGCGGCTTGGCAGCGGCAGGTATTTCAGGGTGACCGCCTGAC | *X. szentirmaii* DSM 16338 | 77 |
| | KB-Ser2 | TCCGCCAACCCAAATAGCAGCGTCGGTTCATCCACCTCAGCCAACATGTCAGTAAAGAAGCGAGTATGTTCTGCCTGACTCACACTCAGGATTTGAGCGATAAAG | | 78 |
| | KB-Lys1 | ACCATTCAATATCCTGATTATGCGGCTTGGCAGCGGCAGGTATTTCAGGGTGAGGTACTGGAAAAGC | *X. nematophila* HGB081 | 79 |
| | KB-Lys2 | CTCAGCCAACATGTCAGTAAAGAAGCGAGTATGTTCTGCCTGACTTACACTGCGGGTTTGGGC | | 80 |
| | AL-GxpS-1 | ACTGTTTCTCCATACCCGTTTTTTTGGGCTAACAGGAGGAATTCCATGAAAGATAGCATGGCTAAAAAGG | pFF1_gxpS_WT | 81 |
| | AL-GxpS-2 | AAATACCTGCCGCTGCC | | 82 |
| | AL-GxpS-3 | AGTCAGGCAGAACATACTCGCTTCTTTAC | | 83 |
| | AL-GxpS-4 | TTTGCTCATGAACTCGCCAGAACCAGCAGCGGAGCCAGCGGATCCCAGCGCCTCCGCTTCAC | | 84 |
| pFF1_library 2 | KB-xeyS-C | TTCTGCCAACATGTCGGTAAAGAATCGGTGATGTTCTGTCTGGTCTTCCCCCAACCAGGACTG | *X. indica* DSM 17382 | 85 |
| | KB-xeyS-N | ACTGTTTCTCCATACCCGTTTTTTTGGGCTAACAGGAGGAATTCCATGAAAGATAACATGGCTACAACG | | 86 |
| | KB-BicA-C | TTCTGCCAACATGTCGGTAAAGAATCGGTGATGTTCTGTCTGGTCCATCCCCAACCAGGACTG | *X. budapestensis* DSM 16342 | 87 |
| | KB-BicA-N | ACTGTTTCTCCATACCCGTTTTTTTGGGCTAACAGGAGGAATTCCATGAAAGATAACATTGCTACAGTGG | | 88 |
| | KB-17902-C | TTCTGCCAACATGTCGGTAAAGAATCGGTGATGTTCTGTCTGGTCAACGCCCAGCCGGGCTTGAGC | *X. miraniensis* DSM 17902 | 89 |
| | KB-17902-N | ACTGTTTCTCCATACCCGTTTTTTTGGGCTAACAGGAGGAATTCCATGAAAAATGATAAGGTGATGACTCTGC | | 90 |

TABLE 1-continued

Oligonucleotides used in this work.

| Plasmid | Oligonucleotide | Sequence (5'→3') | Template | SEQ ID |
|---|---|---|---|---|
| | KB-2022-C | TTCTGCCAACATGTCGGTAAAGAATCGGTGATGTTCTGTCTGGTCCACCCCCTGGTGGGCC | X. nematophila HGB081 | 91 |
| | KB-2022-N | ACTGTTTCTCCATACCCGTTTTTTTGGGCTAACAGGAGGAATTCCATGAAAGATAGCATGGCTAAAAAGG | | 92 |
| | KB-XLSer1 | ACCATTCAATATCCTGATTATGCGGCTTGGCAGCGGCAGGTATTTCAGGGTGACCGCCTGAC | X. szentirmaii DSM 16338 | 93 |
| | KB-XLSer2 | CTCAGCCAACATGTCAGTAAAGAAGCGAGTATGTTCTGCCTGACTCACACTCAGGATTTGAGCGATAAAG | | 94 |
| | KB-AmbF-1 | ACCATTCAATATCCTGATTATGCGGCTTGGCAGCGGCAGGTATTTTCGGTTGAACGCTTACAATCC | X. miraniensis DSM 17902 | 95 |
| | KB-AmbF-2 | CTCAGCCAACATGTCAGTAAAGAAGCGAGTATGTTCTGCCTGACTGATACCCAGCCGGGCTTG | | 96 |
| | KB-AmbW-1 | ACCATTCAATATCCTGATTATGCGGCTTGGCAGCGGCAGGTATTTTCATCGGAACGGGTACAAATTC | X. indica DSM 17382 | 97 |
| | KB-AmbW-2 | CTCAGCCAACATGTCAGTAAAGAAGCGAGTATGTTCTGCCTGACTTACCCCCATCCGTGCCTG | | 98 |
| | KB-Thr1 | ACCATTCAATATCCTGATTATGCGGCTTGGCAGCGGCAGGTATTTTCGGCAGCACAGATACAGTCTC | P. luminescens TT01 | 99 |
| | KB-Th 2 | CTCAGCCAACATGTCAGTAAAGAAGCGAGTATGTTCTGCCTGACTCACGCCCAACCGGACC | | 100 |
| | KB-Arg1 | ACCATTCAATATCCTGATTATGCGGCTTGGCAGCGGCAGGTATTTTCTGCTGATCGTATTCAGGTGCAG | X. budapestensis DSM 16342 | 101 |
| | KB-Arg2 | CTCAGCCAACATGTCAGTAAAGAAGCGAGTATGTTCTGCCTGACTCACGCCCAACCGGACC | | 102 |
| | KB-Lys1 | ACCATTCAATATCCTGATTATGCGGCTTGGCAGCGGCAGGTATTTCAGGGTGAGGTACTGGAAAAGC | X. nematophila HGB081 | 103 |
| | KB-Lys2 | CTCAGCCAACATGTCAGTAAAGAAGCGAGTATGTTCTGCCTGACTTACACTGCGGGTTTGGGC | | 104 |
| | AL-GxpS P3 | AGTCAGGCAGAACATACTCGCTTCTTTAC | pFF1_gxpS_WT | 105 |
| | AL-GxpS-P4 | TTTGCTCATGAACTCGCCAGAACCAGCAGCGGAGCCAGCGGATCCCAGCGCCTCCGCTTCAC | | 106 |

TABLE 1-continued

Oligonucleotides used in this work.

| Plasmid | Oligo-nucleotide | Sequence (5'→3') | Template | SEQ ID |
|---|---|---|---|---|
| | KB-Lib3-1 | GACCAGACAGAACATCACCG | | 107 |
| | KB-Lib3-2 | AAATACCTGCCGCTGCC | | 108 |
| pFF1_library 3 | KB-XL-X3 RV | CCAACATGTCAGTAAAGAAGCGAGTATGTTCTGCCTGACTCACACTCAGGATTTGAGCG | *X. szentirmaii* DSM 16338 | 109 |
| | KB-XL-X3 FW | ATTCAATATCCTGATTATGCGGCTTGGCAGCGGCAGGTATTTCAGGGTGACCGCCTGACC | | 110 |
| | KB-XI-amb X3 RV | CCAACATGTCAGTAAAGAAGCGAGTATGTTCTGCCTGACTCATACCTAGACGTGCCTGTGC | *X. indica* DSM 17382 | 111 |
| | KB-XI-amb X3 FW | ATTCAATATCCTGATTATGCGGCTTGGCAGCGGCAGGTATTTTCGGCAGAACGGATACAAATTC | | 112 |
| | KB-Kol X3 - RV | CCAACATGTCAGTAAAGAAGCGAGTATGTTCTGCCTGACTCACGCCCAACCGGACC | *P. luminescens* TT01 | 113 |
| | KB-Kol X3 - FW | ATTCAATATCCTGATTATGCGGCTTGGCAGCGGCAGGTATTTTCGGCAGCACAGATACAGTC | | 114 |
| | KB-Kol X2 RV | AAATACCTGCCGCTGCCAAGCCGCATAATCAGGATATTGAATCGTCAACGGTAGCAACGG | *P. luminescens* TT01 | 115 |
| | KB-Kol X2 FW | ACCTTTCCGCAATCTGGTGGCTCAGGCTCGGCAGGGGGTTAGTCAGGCTGAGCATACCCG | | 116 |
| | KB-BicA X3 RV | CCAACATGTCAGTAAAGAAGCGAGTATGTTCTGCCTGACTCACGCCCAACCGGACC | *X. budapestensis* DSM 16342 | 117 |
| | KB-BicA X3 FW | ATTCAATATCCTGATTATGCGGCTTGGCAGCGGCAGGTATTTTCTGCTGATCGTATTCAGGTGC | | 118 |
| | KB-Bb 2 RV | TCATGAACTCGCCAGAACCAGCAGCGGAGCCAGCGGATCCCAGCGCCTCCGCTTCACAATTC | pFF1_gxpS_WT | 119 |
| | KB-Bb 2 FW | AGTCAGGCAGAACATACTCGC | | 120 |
| | KB-Bb 1 RV | AACCCCCTGCCGAGCC | pFF1_gxpS_WT | 121 |
| | KB-Bb 1 FW | AACCCCCTGCCGAGCC | | 122 |
| | KB-amb X2 RV | AAATACCTGCCGCTGCCAAGCCGCATAATCAGGATATTGAATTGCCAATGGTGGCAAGGG | *X. indica* DSM 17382 | 123 |

TABLE 1-continued

Oligonucleotides used in this work.

| Plasmid | Oligonucleotide | Sequence (5'→3') | Template | SEQ ID |
|---|---|---|---|---|
| | KB-amb X2 FW | ACCTTTCCGCAATCTGGTGGCTCAGGCTCGGCAGGGGGTTAGCCAGACAGAGCACACCCG | | 124 |
| | KB-17902 X3 RV | CCAACATGTCAGTAAAGAAGCGAGTATGTTCTGCCTGACTGATACCCAGCCGGGCTTGTGC | X. miraniensis DSM 17902 | 125 |
| | KB-17902 X3 FW | ATTCAATATCCTGATTATGCGGCTTGGCAGCGGCAGGTATTTTCGGTTGAACGCTTACAATCC | | 126 |
| | KB-2022 X3 RV | CCAACATGTCAGTAAAGAAGCGAGTATGTTCTGCCTGACTGACACCCTGCCGAGCC | X. nematophila HGB0 81 | 127 |
| | KB-2022 X3 FW | ATTCAATATCCTGATTATGCGGCTTGGCAGCGGCAGGTATTTTCTGATGAAGGCGTGCAGG | | 128 |
| | KB-2022 X2 RV | AAATACCTGCCGCTGCCAAGCCGCATAATCAGGATATTGAATGGTCAATGGCGGCAGCGG | X. nematophila HGB0 81 | 129 |
| | KB-2022 X2 FW | ACCTTTCCGCAATCTGGTGGCTCAGGCTCGGCAGGGGGTTAGTCAGGAAGCGTACACGCG | | 130 |

LITERATURE

Altschul S F, Gish W, Miller W, Myers E W, Lipman D J, *J. Mol. Biol.* 1990, 215, 403-410

Belshaw P J, Walsh C T, Stachelhaus T, *Science* 1999, 284, 486-9-489

Bloudoff, K, Rodionov, D & Schmeing, T M. *J. Mol. Biol.* 2013, 425, 3137-3150.

Bode H B, Reimer D, Fuchs S W, Kirchner F, Dauth C, Kegler C, Lorenzen W, Brachmann A O, Grün P. *Chemistry—A European Journal* 2012, 18, 2342.

Bode H B, Brachmann A O, Jadhav K B, Seyfarth L, Dauth C, Fuchs S W, Kaiser M, Waterfield N R, Sack H, Heinemann S H, Arndt H D. *Angew Chem Int Ed Engl* 2015, 54, 10352.

Bozhueyuek K A J, Fleischhacker F, Linck A, Tietze A, Niesert C P, Bode H B. *Nat Chem.* 2017, doi:10.1038/nchem.2890

Bruner S D, Weber T, Kohli R M, Schwarzer D, Marahiel M A, Walsh C T, Stubbs M T. *Structure* 2002, 10, 301-310.

Cai X, Nowak S, Wesche F, Bischoff I, Kaiser M, Fürst R, Bode H B. *Nat Chem.* 2017, 9, 379-386.

Calcott, M J & Ackerley D F. *Biotechnol Lett* 2014, 36, 2407-16.

Cane D E, Walsh C T, Khosla C, *Science* 1989, 282, 63-68.

Clugston S L, Sieber S A, Marahiel M A, Walsh C T. *Biochemistry* 2003, 42, 12095-104.

Conti E, Stachelhaus T, Marahiel M A, Brick P. *EMBO J.* 997, 16, 4174-83.

Cosmina, P., Rodriguez, F., Ferra, F., Grandi, G., Perego, M., Venema, G., & Sinderen, D. *Mol Microbiol* 1993, 8, 821-831.

De Crécy-Lagard V, Marlière P, Saurin W. *C R Acad Sci III.* 1995, 318, 927-36.

Du L & Lou L. *Nat. Prod. Rep.* 2009, 27, 255-78.

Emmel E A, Verweij C L, Durand D B, Higgins K M, *Science* 1989, 246, 1617-1620.

Fuchs S W, Proschak A, Jaskolla T W., Karas M & Bode H B. *Org Biomol Chem* 2011, 9, 3130-3132.

Fuchs S W, Sachs C C, Kegler C, Nollmann F I, Karas M, Bode H B. *Analytical Chemistry* 2012, 84, 6948.

Fuchs S W, Bozhüyük K A, Kresovic D, Grundmann F, Dill V, Brachmann A O, Waterfield N R, Bode H B. *Angewandte Chemie* (International ed. in English) 2013, 52, 4108-4112.

Gao, X. Haynes S W, Ames B D, Wang P, Vien L P, Walsh C T, Tang Y. *Nat. Chem. Biol.* 2012, 8, 823-830 (2012).

Gaudelli N M & Townsend C A. *Nat. Chem. Biol.* 2014, 10, 251-258.

Gietz R D & Schiestl R H. *Nat Protoc* 2007, 2, 1-4.

Harvey A L, Edrada-Ebel R & Quinn R J. *Nat Rev Drug Discov* 2015, 14, 111-29.

Haynes S W Ames B D, Gao X, Tang Y, Walsh C T. *Biochemistry* 2011, 50, 5668-5679.

Horsman M E, Hari T P A. & Boddy C N. *Nat. Prod. Rep.* 2015. doi:10.1039/c4np00148f Ishizuka M, Takayama H, Takeuchi T, *J. Antibiot.* 1967, 20, 15-24.

Keating T A, Marshall C G, Walsh C T, Keating A E, *Nat Struct Biol.* 2002, 9, 522-6.

Kegler C, Nollmann F I, Ahrendt T, Fleischhacker F, Bode E, Bode H B. *ChemBioChem* 2014, 15, 826.

Kohli R M, Trauger J W, Schwarzer D, Marahiel M A, Walsh C T. *Biochemistry,* 2001, 40, 7099-7108.

Kolb H C, Sharpless K B. *Drug Discov Today.* 2003, 8, 1128-37.

Konz, D., Klens, A., Schörgendorfer, K. & Marahiel, M. A. *Chem Biol* 1998, 4, 927-937.

Kopp F & Marahiel M A. *Nat. Prod. Rrep.* 2007, 24, 735-49.

Korman T P, Crawford J M, Labonte J W, Newman A G, Wong J, Townsend C A, Tsai S C. *Proc. Natl. Acad. Sci. USA* 2010, 107, 6246-6251.

Kries H, Wachtel R, Pabst A, Wanner B, Niquille D, Hilvert D, *Angew. Chem. Int. Ed.* 2014, 53, 10105-10108.

Kronenwerth M, Bozhüyük K A, Kahnt A S, Steinhilber D, Gaudriault S, Kaiser M, Bode H B. *Chemistry—A European Journal* 2014, 20, 17478-87.

Lefevre F, Robe P, Jarrin C, Ginolhac A, Zago C, Auriol D, Vogel T M, Simonet P, Nalin R. *Res Microbiol* 2008, 159, 153-61.

Ling L L, Schneider T, Peoples A J, Spoering A L. *Nature* 2015, 517, 445-459.

Loeffler W, Tschen J, Vanittanakom N. *J. Phytopathol.* 1986, 115, 204-213.

Marahiel M A, *Chem. Biol.* 997, 4, 561-567.

Marahiel M A. *Nat Prod Rep* 2015. doi:10.1039/c5np00082c

Meyer S, Kehr J C, Mainz A, Dehm D, Petras D, Süssmuth R D, Dittmann E. *Cell Chem Biol* 2016, 23, 462-471.

Mitchell C A, Shi C, Aldrich C C, Gulick A M. *Biochemistry* 2012, 51, 3252-3263.

Nishihara K, Kanemori M, Yanagi H & Yura, T. *Applied and environmental microbiology* 2000, 66, 884-889.

Nollmann F I, Dauth C, Mulley G, Kegler C, Kaiser M, Waterfield N R, Bode H B. *ChemBioChem* 2014, 16, 205-8.

Li R, Oliver R A. & Townsend C A. *Cell Chem Biol* 2016, 24, 24-34.

Phelan V V, Du Y, McLean J A, Bachmann B O. Chem Biol. 2009, 29, 16, 473-8.

Rausch C, Weber T, Kohlbacher O, Wohlleben W, Huson D H. *Nuc. Acids. Res.* 2005, 33, 5799-5808.

Rausch C, Hoof I, Weber T, Wohlleben W, Huson D H. BMC Evol Biol. 2007, 7:78.

Reimer D, Cowles K N, Proschak A, Nollmann F I, Dowling A J, Kaiser M, ffrench-Constant R, Goodrich-Blair H, Bode H B. *ChemBioChem* 2013, 14, 1991-997.

Samel S A, Schoenafinger G, Knappe T A, Marahiel M A & Essen L O. *Structure* 2007, 15, 781-792.

Schimming O, Fleischhacker F, Nollmann F I & Bode H B. *ChemBioChem* 2014, 15, 1290.

Sieber S A, Marahiel M A. *Chem. Rev.* 2005, 105, 715-738.

Sletten E M, Bertozzi C R. Angew Chem Int Ed Engl. 2009, 48, 6974-98.

Smith S, Tsai S. *Nat. Prod. Rep.* 2007, 24, 1041-1072.

Stachelhaus T, Schneider A, Marahiel M A. Science 1995, 269, 69-72.

Stachelhaus T, Mootz H D, Bergendahl V, Marahiel M A. J Biol Chem. 1998, 273, 22773-81.

Stachelhaus T, Mootz H D, Marahiel M A. *Chem. Biol.* 1999, 6, 493-505.

Strieker M & Marahiel M A. *Curr. Opin. Struct. Biol.* 2010, 10, 234-240.

Sundlov J A & Gulick A M. *Acta Crystallogr. D. Biol. Crystallogr* 2013, 69, 1482-1492.

Süssmuth R D, Mainz A. *Angew Chem Int Ed Engl.* 2017, 56, 3770-3821.

Tan X F, Dai Y N, Zhou K, Jiang Y L, Ren Y M, Chen Y, Zhou C Z. *Acta Cryst* 2015, D71, 873-881.

Tanovic A, Samel S A, Essen L O, Marahiel M A. *Science* 2008, 321, 659-663

Trauger J W, Kohli R M, Walsh C T. *Nature* 2000, 407, 215-218.

Tseng C C, Bruner S D, Kohli R M, Marahiel M A, Walsh C T, Sieber S A. *Biochemistry* 2002, 41, 13350-13359.

Winn, M, Fyans, J K, Zhuo Y & Micklefield J. *Nat Prod Rep* 2015, 33, 317-347.

The invention claimed is:

1. A library of non-ribosomal peptide synthetase (NRPS) eXchange Units ($XU_{2.0}$) for assembling an NRPS, wherein the library comprises an $XU_{2.0}$, and wherein the $XU_{2.0}$ is selected from the group consisting of:

$C_{Dsub}$-A-T-$C_{Asub}$, $C_{Dsub}$-A-T-$C/E_{Asub}$, $C/E_{Dsub}$-A-T-$C/E_{Asub}$, and $C/E_{Dsub}$-A-T-$C_{Asub}$, wherein A is an adenylation domain, T is a thiolation domain, $C_{Asub}$ is an incomplete condensation-domain comprising only an acceptor site subdomain, $C/E_{Asub}$ is an incomplete condensation/epimerization-domain comprising only an acceptor site subdomain, $C_{Dsub}$ is an incomplete condensation-domain comprising only a donor site subdomain, and $C/E_{Dsub}$ is an incomplete condensation/epimerization-domain comprising only a donor site subdomain wherein the $XU_{2.0}$ does not comprise a full-length C- or C/E-domain comprising both acceptor site subdomain and donor site subdomain.

2. The library according to claim 1, comprising at least two $XU_{2.0}$ of which each has a different amino acid specificity.

3. The library according to claim 1, the library further comprising a $XU_{2.0}$ termination and/or initiation unit, wherein the $XU_{2.0}$ initiation unit comprises only a C or C/E domain donor subdomain, a domain structure C-$A^X$-T-$C_{Dsub}^X$ or C-$A^X$-T-$C/E_{Dsub}^X$, specific for the incorporation of acyl units as starting units, and wherein the termination unit comprises any one of a terminal condensation domain (Cterm), an internal condensation (C) domain, an internal condensation and epimerization (C/E)-didomain, a cyclization (Cy) domain, an epimerization (E) domain, a reduction (R) domain, an oxidation (Ox) domain, or a thioesterase (TE) domain.

4. The library according to claim 1, the library further comprising a $XU_{2.0}$ initiation unit.

5. The library according to claim 1, wherein the library comprises at least two $XU_{2.0}$ and the at least two $XU_{2.0}$ when put into sequence provide the NRPS.

6. The library according to claim 1, further comprising at least one $XU_{2.0}$ having a modification domain.

7. A method for producing a non-ribosomal peptide synthetase (NRPS), the method comprising a step of assembling at least two NRPS eXchange Units ($XU_{2.0}$), wherein each $XU_{2.0}$ is selected from the group consisting of:

$C_{Dsub}$-A-T-$C_{Asub}$, $C_{Dsub}$-A-T-$C/E_{Asub}$, $C/E_{Dsub}$-A-T-$C/E_{Asub}$, and $C/E_{Dsub}$-A-T-$C_{Asub}$, wherein A is an adenylation domain, T is a thiolation domain, $C_{Asub}$ is an incomplete condensation-domain comprising only an acceptor site subdomain, $C/E_{Asub}$ is an incomplete condensation/epimerization-domain comprising only an acceptor site subdomain, $C_{Dsub}$ is an incomplete condensation-domain comprising only a donor site subdomain and $C/E_{Dsub}$ is an incomplete condensation/epimerization-domain comprising only a donor site subdomain;

wherein the XU2.0 does not comprise a full-length C- or C/E-domain comprising both acceptor site subdomain and donor site subdomain.

8. A method for the production of non-ribosomal peptides having a specific sequence, the method comprising assembling a NRPS according to the method accordingly to claim 7, wherein the NRPS is composed of a sequence of at least three $XU_{2.0}$ having specificity according to the non-ribosomal peptide to be produced.

9. The library according to claim 2, wherein each different amino acid specificity is selected from a specificity to any one or two, three, four or more natural or non-natural amino acid.

10. The library according to claim 3, wherein the acyl units comprise fatty acids or derivatives thereof.

11. The library according to claim 4, wherein the $XU_{2.0}$ initiation unit is $C_{Asub}$-$A^X$-T-$C_{Dsub}^X$, $C/E_{Asub}$-$A^X$-T-$C_{Dsub}^X$, $C_{Asub}$-$A^X$-T-$C/E_{Dsub}^X$, or $C/E_{Asub}$-$A^X$-T-$C/E_{Dsub}^X$.

12. The library according to claim 5, wherein the library comprises three, four, or more $XU_{2.0}$ put into sequence.

13. The library according to claim 6, wherein the modification domain is an E, MT, or Ox modification domain.

14. The library accordingly to claim 1, comprising a first $XU_{2.0}$ and a second $XU_{2.0}$ each selected from the group consisting of:

$C_{Dsub}$-A-T-$C_{Asub}$, $C_{Dsub}$-A-T-$C/E_{Asub}$, $C/E_{Dsub}$-A-T-$C/E_{Asub}$, and $C/E_{Dsub}$-A-T-$C_{Asub}$, wherein the first $XU_{2.0}$ and the second $XU_{2.0}$, when connected to each other, form a functional assembled C or C/E domain composed of one partial C or C/E domain of the first $XU_{2.0}$ and one partial C or C/E domain of the second $XU_{2.0}$.

15. The library accordingly to claim 1, wherein the library comprises at least two $XU_{2.0}$ each specific for a different or identical amino acid X.

16. The library accordingly to claim 1, wherein the $C_{Asub}$, $C/E_{Asub}$, $C_{Dsub}$, and $C/E_{Dsub}$ are specific for a given amino acid X.

* * * * *

SEQUENCE LISTING

```
<160> NUMBER OF SEQ ID NOS: 136

<210> SEQ ID NO 1
<211> LENGTH: 38
<212> TYPE: DNA
<213> ORGANISM: Artificial Sequence
<220> FEATURE:
<223> OTHER INFORMATION: Primer According to Table 1

<400> SEQUENCE: 1
catcaccatc atcaccaccc tcaacaacct gtcacggc                              38

<210> SEQ ID NO 2
<211> LENGTH: 46
<212> TYPE: DNA
<213> ORGANISM: Artificial Sequence
<220> FEATURE:
<223> OTHER INFORMATION: Primer Sequence According to Table 1

<400> SEQUENCE: 2
cagcctaggt taattaagct gttaagtcag atcaatcagc ggcaac                     46

<210> SEQ ID NO 3
<211> LENGTH: 21
<212> TYPE: DNA
<213> ORGANISM: Artificial Sequence
<220> FEATURE:
<223> OTHER INFORMATION: Primer Sequence According to Table 1
```

```
<400> SEQUENCE: 3
cagcttaatt aacctaggct g                                            21

<210> SEQ ID NO 4
<211> LENGTH: 18
<212> TYPE: DNA
<213> ORGANISM: Artificial Sequence
<220> FEATURE:
<223> OTHER INFORMATION: Primer Sequence According to Table 1

<400> SEQUENCE: 4
gtggtgatga tggtgatg                                                18

<210> SEQ ID NO 5
<211> LENGTH: 62
<212> TYPE: DNA
<213> ORGANISM: Artificial Sequence
<220> FEATURE:
<223> OTHER INFORMATION: Primer Sequence According to Table 1

<400> SEQUENCE: 5
tcatgaactc gccagaacca gcagcggagc cagcggatcc cagcgcctcc gcttcacaat   60
tc                                                                 62

<210> SEQ ID NO 6
<211> LENGTH: 20
<212> TYPE: DNA
<213> ORGANISM: Artificial Sequence
<220> FEATURE:
<223> OTHER INFORMATION: Primer Sequence According to Table 1

<400> SEQUENCE: 6
tggaatgcga ccgaagaacc                                              20

<210> SEQ ID NO 7
<211> LENGTH: 60
<212> TYPE: DNA
<213> ORGANISM: Artificial Sequence
<220> FEATURE:
<223> OTHER INFORMATION: Primer Sequence According to Table 1

<400> SEQUENCE: 7
cacatacctg agtaggatac ggttcttcgg tcgcattcca agttttcagc aacaactggc   60

<210> SEQ ID NO 8
<211> LENGTH: 60
<212> TYPE: DNA
<213> ORGANISM: Artificial Sequence
<220> FEATURE:
<223> OTHER INFORMATION: Primer Sequence According to Table 1

<400> SEQUENCE: 8
tgttttgcct gcatcggaac gcacgttgtt gctggaaacg tggaatacaa cggaaactgc   60

<210> SEQ ID NO 9
<211> LENGTH: 17
<212> TYPE: DNA
<213> ORGANISM: Artificial Sequence
<220> FEATURE:
<223> OTHER INFORMATION: Primer Sequence According to Table 1

<400> SEQUENCE: 9
cgtttccagc aacaacg                                                 17
```

```
<210> SEQ ID NO 10
<211> LENGTH: 65
<212> TYPE: DNA
<213> ORGANISM: Artificial Sequence
<220> FEATURE:
<223> OTHER INFORMATION: Primer Sequence According to Table 1

<400> SEQUENCE: 10
ttctccatac ccgttttttt gggctaacag gaggaattcc atgaaagata gcatggctaa    60
aaagg                                                                65

<210> SEQ ID NO 11
<211> LENGTH: 62
<212> TYPE: DNA
<213> ORGANISM: Artificial Sequence
<220> FEATURE:
<223> OTHER INFORMATION: Primer Sequence According to Table 1

<400> SEQUENCE: 11
tcatgaactc gccagaacca gcagcggagc cagcggatcc cagcgcctcc gcttcacaat    60
tc                                                                   62

<210> SEQ ID NO 12
<211> LENGTH: 20
<212> TYPE: DNA
<213> ORGANISM: Artificial Sequence
<220> FEATURE:
<223> OTHER INFORMATION: Primer Sequence According to Table 1

<400> SEQUENCE: 12
tggaatgcga ccgaagaacc                                                20

<210> SEQ ID NO 13
<211> LENGTH: 19
<212> TYPE: DNA
<213> ORGANISM: Artificial Sequence
<220> FEATURE:
<223> OTHER INFORMATION: Primer Sequence According to Table 1

<400> SEQUENCE: 13
aagccattga cgctgccag                                                 19

<210> SEQ ID NO 14
<211> LENGTH: 60
<212> TYPE: DNA
<213> ORGANISM: Artificial Sequence
<220> FEATURE:
<223> OTHER INFORMATION: Primer Sequence According to Table 1

<400> SEQUENCE: 14
tgttttgcct gcatcggaac gcacgttgtt gctggaaacg tggaatacaa cggaaactgc    60

<210> SEQ ID NO 15
<211> LENGTH: 17
<212> TYPE: DNA
<213> ORGANISM: Artificial Sequence
<220> FEATURE:
<223> OTHER INFORMATION: Primer Sequence According to Table 1

<400> SEQUENCE: 15
cgtttccagc aacaacg                                                   17

<210> SEQ ID NO 16
<211> LENGTH: 65
```

```
<212> TYPE: DNA
<213> ORGANISM: Artificial Sequence
<220> FEATURE:
<223> OTHER INFORMATION: Primer Sequence According to Table 1

<400> SEQUENCE: 16
ttctccatac ccgttttttt gggctaacag gaggaattcc atgaaagata gcatggctaa     60
aaagg                                                                 65

<210> SEQ ID NO 17
<211> LENGTH: 64
<212> TYPE: DNA
<213> ORGANISM: Artificial Sequence
<220> FEATURE:
<223> OTHER INFORMATION: Primer Sequence According to Table 1

<400> SEQUENCE: 17
cacatacctg agtaggatac ggttcttcgg tcgcattcca attttccagt aataactccc     60
gctc                                                                  64

<210> SEQ ID NO 18
<211> LENGTH: 60
<212> TYPE: DNA
<213> ORGANISM: Artificial Sequence
<220> FEATURE:
<223> OTHER INFORMATION: Primer Sequence According to Table 1

<400> SEQUENCE: 18
tcaatatcct gattatgcgg tctggcagcg tcaatggctt tcaggtgaag gagtacaggc     60

<210> SEQ ID NO 19
<211> LENGTH: 70
<212> TYPE: DNA
<213> ORGANISM: Artificial Sequence
<220> FEATURE:
<223> OTHER INFORMATION: Primer Sequence According to Table 1

<400> SEQUENCE: 19
actgtttctc catcccgtt tttttgggct aacaggagga attccatgaa agatagcatg      60
gctaaaaagg                                                            70

<210> SEQ ID NO 20
<211> LENGTH: 61
<212> TYPE: DNA
<213> ORGANISM: Artificial Sequence
<220> FEATURE:
<223> OTHER INFORMATION: Primer Sequence According to Table 1

<400> SEQUENCE: 20
cccaatcaac atatcggtaa aaaagcgagt atgttccatc tggctcaccc cctggtgggc     60
c                                                                     61

<210> SEQ ID NO 21
<211> LENGTH: 65
<212> TYPE: DNA
<213> ORGANISM: Artificial Sequence
<220> FEATURE:
<223> OTHER INFORMATION: Primer Sequence According to Table 1

<400> SEQUENCE: 21
cccgtacctt tccgtaatct ggtcgctcag gcccaccagg gggtgagcca gatggaacat     60
actcg                                                                 65
```

```
<210> SEQ ID NO 22
<211> LENGTH: 62
<212> TYPE: DNA
<213> ORGANISM: Artificial Sequence
<220> FEATURE:
<223> OTHER INFORMATION: Primer Sequence According to Table 1

<400> SEQUENCE: 22
cgtccgacgc caataatcac tctgtgcctg tactccttca cctgaaaacc actggcgttg      60
cc                                                                    62

<210> SEQ ID NO 23
<211> LENGTH: 22
<212> TYPE: DNA
<213> ORGANISM: Artificial Sequence
<220> FEATURE:
<223> OTHER INFORMATION: Primer Sequence According to Table 1

<400> SEQUENCE: 23
tcaggtgaag gagtacaggc ac                                              22

<210> SEQ ID NO 24
<211> LENGTH: 16
<212> TYPE: DNA
<213> ORGANISM: Artificial Sequence
<220> FEATURE:
<223> OTHER INFORMATION: Primer Sequence According to Table 1

<400> SEQUENCE: 24
gacaccctgc cgagcc                                                     16

<210> SEQ ID NO 25
<211> LENGTH: 64
<212> TYPE: DNA
<213> ORGANISM: Artificial Sequence
<220> FEATURE:
<223> OTHER INFORMATION: Primer Sequence According to Table 1

<400> SEQUENCE: 25
ccggtcccgt tccgccattt agtggcacag gctcggcagg gtgtccaagg cgctgttctc      60
actg                                                                  64

<210> SEQ ID NO 26
<211> LENGTH: 62
<212> TYPE: DNA
<213> ORGANISM: Artificial Sequence
<220> FEATURE:
<223> OTHER INFORMATION: Primer Sequence According to Table 1

<400> SEQUENCE: 26
ctcagccaac atttcagtaa agaaacgggt atgttcagcc tgactcacgc tcagggtctg      60
gg                                                                    62

<210> SEQ ID NO 27
<211> LENGTH: 20
<212> TYPE: DNA
<213> ORGANISM: Artificial Sequence
<220> FEATURE:
<223> OTHER INFORMATION: Primer Sequence According to Table 1

<400> SEQUENCE: 27
agtcaggctg aacatacccg                                                 20
```

```
<210> SEQ ID NO 28
<211> LENGTH: 62
<212> TYPE: DNA
<213> ORGANISM: Artificial Sequence
<220> FEATURE:
<223> OTHER INFORMATION: Primer Sequence According to Table 1

<400> SEQUENCE: 28
tttgctcatg aactcgccag aaccagcagc ggagccagcg gatcccagcg cctccgcttc    60
ac                                                                   62

<210> SEQ ID NO 29
<211> LENGTH: 70
<212> TYPE: DNA
<213> ORGANISM: Artificial Sequence
<220> FEATURE:
<223> OTHER INFORMATION: Primer Sequence According to Table 1

<400> SEQUENCE: 29
actgtttctc catacccgtt tttttgggct aacaggagga attccatgaa agatagcatg    60
gctaaaaagg                                                           70

<210> SEQ ID NO 30
<211> LENGTH: 61
<212> TYPE: DNA
<213> ORGANISM: Artificial Sequence
<220> FEATURE:
<223> OTHER INFORMATION: Primer Sequence According to Table 1

<400> SEQUENCE: 30
cccaatcaac atatcggtaa aaaagcgagt atgttccatc tggctcaccc cctggtgggc    60
c                                                                    61

<210> SEQ ID NO 31
<211> LENGTH: 65
<212> TYPE: DNA
<213> ORGANISM: Artificial Sequence
<220> FEATURE:
<223> OTHER INFORMATION: Primer Sequence According to Table 1

<400> SEQUENCE: 31
cccgtacctt tccgtaatct ggtcgctcag gcccaccagg gggtgagcca gatggaacat    60
actcg                                                                65

<210> SEQ ID NO 32
<211> LENGTH: 62
<212> TYPE: DNA
<213> ORGANISM: Artificial Sequence
<220> FEATURE:
<223> OTHER INFORMATION: Primer Sequence According to Table 1

<400> SEQUENCE: 32
cgtccgacgc caataatcac tctgtgcctg tactccttca cctgaaaacc actggcgttg    60
cc                                                                   62

<210> SEQ ID NO 33
<211> LENGTH: 22
<212> TYPE: DNA
<213> ORGANISM: Artificial Sequence
<220> FEATURE:
<223> OTHER INFORMATION: Primer Sequence According to Table 1

<400> SEQUENCE: 33
```

```
tcaggtgaag gagtacaggc ac                                              22

<210> SEQ ID NO 34
<211> LENGTH: 16
<212> TYPE: DNA
<213> ORGANISM: Artificial Sequence
<220> FEATURE:
<223> OTHER INFORMATION: Primer Sequence According to Table 1

<400> SEQUENCE: 34
gacaccctgc cgagcc                                                     16

<210> SEQ ID NO 35
<211> LENGTH: 64
<212> TYPE: DNA
<213> ORGANISM: Artificial Sequence
<220> FEATURE:
<223> OTHER INFORMATION: Primer Sequence According to Table 1

<400> SEQUENCE: 35
gccggtcccg ttccgccatt tagtggcaca ggctcggcag ggtgtcagtc aggaagccca     60
cacc                                                                  64

<210> SEQ ID NO 36
<211> LENGTH: 61
<212> TYPE: DNA
<213> ORGANISM: Artificial Sequence
<220> FEATURE:
<223> OTHER INFORMATION: Primer Sequence According to Table 1

<400> SEQUENCE: 36
ctcagccaac atttcagtaa agaaacgggt atgttcagcc tgactcaccc ccaaccgaac     60
c                                                                     61

<210> SEQ ID NO 37
<211> LENGTH: 20
<212> TYPE: DNA
<213> ORGANISM: Artificial Sequence
<220> FEATURE:
<223> OTHER INFORMATION: Primer Sequence According to Table 1

<400> SEQUENCE: 37
agtcaggctg aacatacccg                                                 20

<210> SEQ ID NO 38
<211> LENGTH: 62
<212> TYPE: DNA
<213> ORGANISM: Artificial Sequence
<220> FEATURE:
<223> OTHER INFORMATION: Primer Sequence According to Table 1

<400> SEQUENCE: 38
tttgctcatg aactcgccag aaccagcagc ggagccagcg gatcccagcg cctccgcttc     60
ac                                                                    62

<210> SEQ ID NO 39
<211> LENGTH: 111
<212> TYPE: DNA
<213> ORGANISM: Artificial Sequence
<220> FEATURE:
<223> OTHER INFORMATION: Primer Sequence According to Table 1

<400> SEQUENCE: 39
agattagcgg atcctacctg acgctttta tcgcaactct ctactgtttc tccatacccg      60
```

```
tttttttggg ctaacaggag gaattccatg aaagataaca ttgctacagt g        111
```

<210> SEQ ID NO 40
<211> LENGTH: 21
<212> TYPE: DNA
<213> ORGANISM: Artificial Sequence
<220> FEATURE:
<223> OTHER INFORMATION: Primer Sequence According to Table 1

<400> SEQUENCE: 40

```
ccaataatca ctctgtgcct g                                          21
```

<210> SEQ ID NO 41
<211> LENGTH: 20
<212> TYPE: DNA
<213> ORGANISM: Artificial Sequence
<220> FEATURE:
<223> OTHER INFORMATION: Primer Sequence According to Table 1

<400> SEQUENCE: 41

```
gaactggttg cactttacgc                                            20
```

<210> SEQ ID NO 42
<211> LENGTH: 18
<212> TYPE: DNA
<213> ORGANISM: Artificial Sequence
<220> FEATURE:
<223> OTHER INFORMATION: Primer Sequence According to Table 1

<400> SEQUENCE: 42

```
catccctaac cgggactg                                              18
```

<210> SEQ ID NO 43
<211> LENGTH: 98
<212> TYPE: DNA
<213> ORGANISM: Artificial Sequence
<220> FEATURE:
<223> OTHER INFORMATION: Primer Sequence According to Table 1

<400> SEQUENCE: 43

```
catccttga cggacagggc ggcaacctgc cagcgccggc acccttccgc aatctggtag  60
cgcagtcccg gttagggatg agtcaggcag cccatacc                        98
```

<210> SEQ ID NO 44
<211> LENGTH: 103
<212> TYPE: DNA
<213> ORGANISM: Artificial Sequence
<220> FEATURE:
<223> OTHER INFORMATION: Primer Sequence According to Table 1

<400> SEQUENCE: 44

```
aacaacaccg gtaaacagtt cttcaccttt gctcatgaac tcgccagaac cagcagcgga  60
gccagcggat ccggcgcgcc ctattgctct gctgatatca gaa                  103
```

<210> SEQ ID NO 45
<211> LENGTH: 20
<212> TYPE: DNA
<213> ORGANISM: Artificial Sequence
<220> FEATURE:
<223> OTHER INFORMATION: Primer Sequence According to Table 1

<400> SEQUENCE: 45

```
gaccagacag aacatcaccg                                            20
```

<210> SEQ ID NO 46
<211> LENGTH: 18
<212> TYPE: DNA
<213> ORGANISM: Artificial Sequence
<220> FEATURE:
<223> OTHER INFORMATION: Primer Sequence According to Table 1

<400> SEQUENCE: 46
ggcccaatcc tatacgcc                                                      18

<210> SEQ ID NO 47
<211> LENGTH: 19
<212> TYPE: DNA
<213> ORGANISM: Artificial Sequence
<220> FEATURE:
<223> OTHER INFORMATION: Primer Sequence According to Table 1

<400> SEQUENCE: 47
cttaccaagc gccacaagg                                                     19

<210> SEQ ID NO 48
<211> LENGTH: 96
<212> TYPE: DNA
<213> ORGANISM: Artificial Sequence
<220> FEATURE:
<223> OTHER INFORMATION: Primer Sequence According to Table 1

<400> SEQUENCE: 48
agaatcggaa caacaccggt aaacagttct tcacctttgc tcatgaactc gccagaacca        60
gcagcggagc cagcggatcc cagcgcctcc gcttca                                  96

<210> SEQ ID NO 49
<211> LENGTH: 96
<212> TYPE: DNA
<213> ORGANISM: Artificial Sequence
<220> FEATURE:
<223> OTHER INFORMATION: Primer Sequence According to Table 1

<400> SEQUENCE: 49
tcggtcagcc caaacggtaa tgtcggttca tccacttctg ccaacatgtc ggtaaagaat        60
cggtgatgtt ctgtctggtc gacaccctgc cgagcc                                  96

<210> SEQ ID NO 50
<211> LENGTH: 96
<212> TYPE: DNA
<213> ORGANISM: Artificial Sequence
<220> FEATURE:
<223> OTHER INFORMATION: Primer Sequence According to Table 1

<400> SEQUENCE: 50
atcctacctg acgcttttta tcgcaactct ctactgtttc tccatacccg ttttttgggg        60
ctaacaggag gaattccatg cgggcaatgg tgaacc                                  96

<210> SEQ ID NO 51
<211> LENGTH: 20
<212> TYPE: DNA
<213> ORGANISM: Artificial Sequence
<220> FEATURE:
<223> OTHER INFORMATION: Primer Sequence According to Table 1

<400> SEQUENCE: 51
gaccagacag aacatcaccg                                                    20

```
<210> SEQ ID NO 52
<211> LENGTH: 18
<212> TYPE: DNA
<213> ORGANISM: Artificial Sequence
<220> FEATURE:
<223> OTHER INFORMATION: Primer Sequence According to Table 1

<400> SEQUENCE: 52
ggcccaatcc tatacgcc                                                    18

<210> SEQ ID NO 53
<211> LENGTH: 19
<212> TYPE: DNA
<213> ORGANISM: Artificial Sequence
<220> FEATURE:
<223> OTHER INFORMATION: Primer Sequence According to Table 1

<400> SEQUENCE: 53
cttaccaagc gccacaagg                                                   19

<210> SEQ ID NO 54
<211> LENGTH: 96
<212> TYPE: DNA
<213> ORGANISM: Artificial Sequence
<220> FEATURE:
<223> OTHER INFORMATION: Primer Sequence According to Table 1

<400> SEQUENCE: 54
agaatcggaa caacaccggt aaacagttct tcacctttgc tcatgaactc gccagaacca      60
gcagcggagc cagcggatcc cagcgcctcc gcttca                                96

<210> SEQ ID NO 55
<211> LENGTH: 96
<212> TYPE: DNA
<213> ORGANISM: Artificial Sequence
<220> FEATURE:
<223> OTHER INFORMATION: Primer Sequence According to Table 1

<400> SEQUENCE: 55
tcggtcagcc caaacggtaa tgtcggttca tccacttctg ccaacatgtc ggtaaagaat      60
cggtgatgtt ctgtctggtc gacaccctgc cgagcc                                96

<210> SEQ ID NO 56
<211> LENGTH: 96
<212> TYPE: DNA
<213> ORGANISM: Artificial Sequence
<220> FEATURE:
<223> OTHER INFORMATION: Primer Sequence According to Table 1

<400> SEQUENCE: 56
atcctacctg acgcttttta tcgcaactct ctactgtttc tccatacccg ttttttgggg     60
ctaacaggag gaattccatg tctgatgaag gcgtgc                                96

<210> SEQ ID NO 57
<211> LENGTH: 20
<212> TYPE: DNA
<213> ORGANISM: Artificial Sequence
<220> FEATURE:
<223> OTHER INFORMATION: Primer Sequence According to Table 1

<400> SEQUENCE: 57
gaccagacag aacatcaccg                                                  20

<210> SEQ ID NO 58
```

```
<211> LENGTH: 18
<212> TYPE: DNA
<213> ORGANISM: Artificial Sequence
<220> FEATURE:
<223> OTHER INFORMATION: Primer Sequence According to Table 1

<400> SEQUENCE: 58
ggcccaatcc tatacgcc                                                        18

<210> SEQ ID NO 59
<211> LENGTH: 19
<212> TYPE: DNA
<213> ORGANISM: Artificial Sequence
<220> FEATURE:
<223> OTHER INFORMATION: Primer Sequence According to Table 1

<400> SEQUENCE: 59
cttaccaagc gccacaagg                                                       19

<210> SEQ ID NO 60
<211> LENGTH: 96
<212> TYPE: DNA
<213> ORGANISM: Artificial Sequence
<220> FEATURE:
<223> OTHER INFORMATION: Primer Sequence According to Table 1

<400> SEQUENCE: 60
agaatcggaa caacaccggt aaacagttct tcacctttgc tcatgaactc gccagaacca          60
gcagcggagc cagcggatcc cagcgcctcc gcttca                                    96

<210> SEQ ID NO 61
<211> LENGTH: 96
<212> TYPE: DNA
<213> ORGANISM: Artificial Sequence
<220> FEATURE:
<223> OTHER INFORMATION: Primer Sequence According to Table 1

<400> SEQUENCE: 61
tcggtcagcc caaacggtaa tgtcggttca tccacttctg ccaacatgtc ggtaaagaat          60
cggtgatgtt ctgtctggtc gacaccctgc cgagcc                                    96

<210> SEQ ID NO 62
<211> LENGTH: 102
<212> TYPE: DNA
<213> ORGANISM: Artificial Sequence
<220> FEATURE:
<223> OTHER INFORMATION: Primer Sequence According to Table 1

<400> SEQUENCE: 62
atcctacctg acgcttttta tcgcaactct ctactgtttc tccatacccg ttttttrggg          60
ctaacaggag gaattccatg gcatttaccg aaaagatctg cg                            102

<210> SEQ ID NO 63
<211> LENGTH: 106
<212> TYPE: DNA
<213> ORGANISM: Artificial Sequence
<220> FEATURE:
<223> OTHER INFORMATION: Primer Sequence According to Table 1

<400> SEQUENCE: 63
cggatcctac ctgacgcttt ttatcgcaac tctctactgt ttctccatac ccgttttttt         60
gggctaacag gaggaattcc atgaaagata gcatggctaa aaaggg                        106
```

<210> SEQ ID NO 64
<211> LENGTH: 99
<212> TYPE: DNA
<213> ORGANISM: Artificial Sequence
<220> FEATURE:
<223> OTHER INFORMATION: Primer Sequence According to Table 1

<400> SEQUENCE: 64
ctatcggcaa ttcaagtaac accggtgcat ctgccaacgt ccgacgccaa taatcactct    60
gtgcctgtac tccttcacct gaaaatacct gccgctgcc                          99

<210> SEQ ID NO 65
<211> LENGTH: 104
<212> TYPE: DNA
<213> ORGANISM: Artificial Sequence
<220> FEATURE:
<223> OTHER INFORMATION: Primer Sequence According to Table 1

<400> SEQUENCE: 65
gcttgtctga atcaacaacc tgatccgctg ccgccattga ccattcaata tcctgattat    60
gctgcctggc agcggcaggt attttcaggt gaaggagtac aggc                    104

<210> SEQ ID NO 66
<211> LENGTH: 101
<212> TYPE: DNA
<213> ORGANISM: Artificial Sequence
<220> FEATURE:
<223> OTHER INFORMATION: Primer Sequence According to Table 1

<400> SEQUENCE: 66
gcacttccga caatccaaat gacaacgttg gctcatctac ctcagccaac atatcggtaa    60
agaaacgggt atgttctgcc tgactgacac cctgccgagc c                       101

<210> SEQ ID NO 67
<211> LENGTH: 102
<212> TYPE: DNA
<213> ORGANISM: Artificial Sequence
<220> FEATURE:
<223> OTHER INFORMATION: Primer Sequence According to Table 1

<400> SEQUENCE: 67
ggcttgcctc ttggggcaaa tggatagcct gcctgcgccg gtcccgttcc gccatttagt    60
ggcacaggct cggcagggtg tcagtcaggc agaacatacc cg                      102

<210> SEQ ID NO 68
<211> LENGTH: 98
<212> TYPE: DNA
<213> ORGANISM: Artificial Sequence
<220> FEATURE:
<223> OTHER INFORMATION: Primer Sequence According to Table 1

<400> SEQUENCE: 68
ccagaatcgg aacaacaccg gtaaacagtt cttcaccttt gctcatgaac tcgccagaac    60
cagcagcgga gccagcggat cccagcgcct ccacttcg                           98

<210> SEQ ID NO 69
<211> LENGTH: 66
<212> TYPE: DNA
<213> ORGANISM: Artificial Sequence
<220> FEATURE:
<223> OTHER INFORMATION: Primer Sequence According to Table 1

<400> SEQUENCE: 69
accattcaat atcctgatta tgcggcttgg cagcggcagg tatttttcggt tgaacgctta    60 caatcc                                                                66

<210> SEQ ID NO 70
<211> LENGTH: 63
<212> TYPE: DNA
<213> ORGANISM: Artificial Sequence
<220> FEATURE:
<223> OTHER INFORMATION: Primer Sequence According to Table 1

<400> SEQUENCE: 70
ctcagccaac atgtcagtaa agaagcgagt atgttctgcc tgactgatac ccagccgggc    60
ttg                                                                  63

<210> SEQ ID NO 71
<211> LENGTH: 67
<212> TYPE: DNA
<213> ORGANISM: Artificial Sequence
<220> FEATURE:
<223> OTHER INFORMATION: Primer Sequence According to Table 1

<400> SEQUENCE: 71
accattcaat atcctgatta tgcggcttgg cagcggcagg tattttcatc ggaacgggta    60
caaattc                                                              67

<210> SEQ ID NO 72
<211> LENGTH: 63
<212> TYPE: DNA
<213> ORGANISM: Artificial Sequence
<220> FEATURE:
<223> OTHER INFORMATION: Primer Sequence According to Table 1

<400> SEQUENCE: 72
ctcagccaac atgtcagtaa agaagcgagt atgttctgcc tgacttaccc ccatccgtgc    60
ctg                                                                  63

<210> SEQ ID NO 73
<211> LENGTH: 67
<212> TYPE: DNA
<213> ORGANISM: Artificial Sequence
<220> FEATURE:
<223> OTHER INFORMATION: Primer Sequence According to Table 1

<400> SEQUENCE: 73
accattcaat atcctgatta tgcggcttgg cagcggcagg tattttcggc agcacagata    60
cagtctc                                                              67

<210> SEQ ID NO 74
<211> LENGTH: 61
<212> TYPE: DNA
<213> ORGANISM: Artificial Sequence
<220> FEATURE:
<223> OTHER INFORMATION: Primer Sequence According to Table 1

<400> SEQUENCE: 74
ctcagccaac atgtcagtaa agaagcgagt atgttctgcc tgactcacgc ccaaccggac    60
c                                                                    61

<210> SEQ ID NO 75
<211> LENGTH: 69
<212> TYPE: DNA
<213> ORGANISM: Artificial Sequence

```
<220> FEATURE:
<223> OTHER INFORMATION: Primer Sequence According to Table 1

<400> SEQUENCE: 75
accattcaat atcctgatta tgcggcttgg cagcggcagg tattttctgc tgatcgtatt    60
caggtgcag                                                            69

<210> SEQ ID NO 76
<211> LENGTH: 61
<212> TYPE: DNA
<213> ORGANISM: Artificial Sequence
<220> FEATURE:
<223> OTHER INFORMATION: Primer Sequence According to Table 1

<400> SEQUENCE: 76
ctcagccaac atgtcagtaa agaagcgagt atgttctgcc tgactcacgc ccaaccggac    60
c                                                                    61

<210> SEQ ID NO 77
<211> LENGTH: 97
<212> TYPE: DNA
<213> ORGANISM: Artificial Sequence
<220> FEATURE:
<223> OTHER INFORMATION: Primer Sequence According to Table 1

<400> SEQUENCE: 77
gtctaaatca acagccagat ccgttgttgc cattgaccat tcaatatcct gattatgcgg    60
cttggcagcg gcaggtattt cagggtgacc gcctgac                             97

<210> SEQ ID NO 78
<211> LENGTH: 105
<212> TYPE: DNA
<213> ORGANISM: Artificial Sequence
<220> FEATURE:
<223> OTHER INFORMATION: Primer Sequence According to Table 1

<400> SEQUENCE: 78
tccgccaacc caaatagcag cgtcggttca tccacctcag ccaacatgtc agtaaagaag    60
cgagtatgtt ctgcctgact cacactcagg atttgagcga taaag                    105

<210> SEQ ID NO 79
<211> LENGTH: 67
<212> TYPE: DNA
<213> ORGANISM: Artificial Sequence
<220> FEATURE:
<223> OTHER INFORMATION: Primer Sequence According to Table 1

<400> SEQUENCE: 79
accattcaat atcctgatta tgcggcttgg cagcggcagg tatttcaggg tgaggtactg    60
gaaaagc                                                              67

<210> SEQ ID NO 80
<211> LENGTH: 63
<212> TYPE: DNA
<213> ORGANISM: Artificial Sequence
<220> FEATURE:
<223> OTHER INFORMATION: Primer Sequence According to Table 1

<400> SEQUENCE: 80
ctcagccaac atgtcagtaa agaagcgagt atgttctgcc tgacttacac tgcgggtttg    60
ggc                                                                  63
```

```
<210> SEQ ID NO 81
<211> LENGTH: 70
<212> TYPE: DNA
<213> ORGANISM: Artificial Sequence
<220> FEATURE:
<223> OTHER INFORMATION: Primer Sequence According to Table 1

<400> SEQUENCE: 81
actgtttctc catacccgtt tttttgggct aacaggagga attccatgaa agatagcatg    60
gctaaaaagg                                                          70

<210> SEQ ID NO 82
<211> LENGTH: 17
<212> TYPE: DNA
<213> ORGANISM: Artificial Sequence
<220> FEATURE:
<223> OTHER INFORMATION: Primer Sequence According to Table 1

<400> SEQUENCE: 82
aaatacctgc cgctgcc                                                  17

<210> SEQ ID NO 83
<211> LENGTH: 29
<212> TYPE: DNA
<213> ORGANISM: Artificial Sequence
<220> FEATURE:
<223> OTHER INFORMATION: Primer Sequence According to Table 1

<400> SEQUENCE: 83
agtcaggcag aacatactcg cttctttac                                     29

<210> SEQ ID NO 84
<211> LENGTH: 62
<212> TYPE: DNA
<213> ORGANISM: Artificial Sequence
<220> FEATURE:
<223> OTHER INFORMATION: Primer Sequence According to Table 1

<400> SEQUENCE: 84
tttgctcatg aactcgccag aaccagcagc ggagccagcg gatcccagcg cctccgcttc    60
ac                                                                  62

<210> SEQ ID NO 85
<211> LENGTH: 63
<212> TYPE: DNA
<213> ORGANISM: Artificial Sequence
<220> FEATURE:
<223> OTHER INFORMATION: Primer Sequence According to Table 1

<400> SEQUENCE: 85
ttctgccaac atgtcggtaa agaatcggtg atgttctgtc tggtcttccc ccaaccagga    60
ctg                                                                 63

<210> SEQ ID NO 86
<211> LENGTH: 69
<212> TYPE: DNA
<213> ORGANISM: Artificial Sequence
<220> FEATURE:
<223> OTHER INFORMATION: Primer Sequence According to Table 1

<400> SEQUENCE: 86
actgtttctc catacccgtt tttttgggct aacaggagga attccatgaa agataacatg    60
gctacaacg                                                           69
```

<210> SEQ ID NO 87
<211> LENGTH: 63
<212> TYPE: DNA
<213> ORGANISM: Artificial Sequence
<220> FEATURE:
<223> OTHER INFORMATION: Primer Sequence According to Table 1

<400> SEQUENCE: 87
ttctgccaac atgtcggtaa agaatcggtg atgttctgtc tggtccatcc ccaaccagga    60
ctg                                                                 63

<210> SEQ ID NO 88
<211> LENGTH: 70
<212> TYPE: DNA
<213> ORGANISM: Artificial Sequence
<220> FEATURE:
<223> OTHER INFORMATION: Primer Sequence According to Table 1

<400> SEQUENCE: 88
actgtttctc catacccgtt ttttgggct aacaggagga attccatgaa agataacatt    60
gctacagtgg                                                          70

<210> SEQ ID NO 89
<211> LENGTH: 66
<212> TYPE: DNA
<213> ORGANISM: Artificial Sequence
<220> FEATURE:
<223> OTHER INFORMATION: Primer Sequence According to Table 1

<400> SEQUENCE: 89
ttctgccaac atgtcggtaa agaatcggtg atgttctgtc tggtcaacgc ccagccgggc    60
ttgagc                                                              66

<210> SEQ ID NO 90
<211> LENGTH: 73
<212> TYPE: DNA
<213> ORGANISM: Artificial Sequence
<220> FEATURE:
<223> OTHER INFORMATION: Primer Sequence According to Table 1

<400> SEQUENCE: 90
actgtttctc catacccgtt ttttgggct aacaggagga attccatgaa aaatgataag    60
gtgatgactc tgc                                                      73

<210> SEQ ID NO 91
<211> LENGTH: 61
<212> TYPE: DNA
<213> ORGANISM: Artificial Sequence
<220> FEATURE:
<223> OTHER INFORMATION: Primer Sequence According to Table 1

<400> SEQUENCE: 91
ttctgccaac atgtcggtaa agaatcggtg atgttctgtc tggtccaccc cctggtgggc    60
c                                                                   61

<210> SEQ ID NO 92
<211> LENGTH: 70
<212> TYPE: DNA
<213> ORGANISM: Artificial Sequence
<220> FEATURE:
<223> OTHER INFORMATION: Primer Sequence According to Table 1

<400> SEQUENCE: 92
actgtttctc catacccgtt tttttgggct aacaggagga attccatgaa agatagcatg    60
gctaaaaagg    70

<210> SEQ ID NO 93
<211> LENGTH: 62
<212> TYPE: DNA
<213> ORGANISM: Artificial Sequence
<220> FEATURE:
<223> OTHER INFORMATION: Primer Sequence According to Table 1

<400> SEQUENCE: 93
accattcaat atcctgatta tgcggcttgg cagcggcagg tatttcaggg tgaccgcctg    60
ac    62

<210> SEQ ID NO 94
<211> LENGTH: 70
<212> TYPE: DNA
<213> ORGANISM: Artificial Sequence
<220> FEATURE:
<223> OTHER INFORMATION: Primer Sequence According to Table 1

<400> SEQUENCE: 94
ctcagccaac atgtcagtaa agaagcgagt atgttctgcc tgactcacac tcaggatttg    60
agcgataaag    70

<210> SEQ ID NO 95
<211> LENGTH: 66
<212> TYPE: DNA
<213> ORGANISM: Artificial Sequence
<220> FEATURE:
<223> OTHER INFORMATION: Primer Sequence According to Table 1

<400> SEQUENCE: 95
accattcaat atcctgatta tgcggcttgg cagcggcagg tattttcggt tgaacgctta    60
caatcc    66

<210> SEQ ID NO 96
<211> LENGTH: 63
<212> TYPE: DNA
<213> ORGANISM: Artificial Sequence
<220> FEATURE:
<223> OTHER INFORMATION: Primer Sequence According to Table 1

<400> SEQUENCE: 96
ctcagccaac atgtcagtaa agaagcgagt atgttctgcc tgactgatac ccagccgggc    60
ttg    63

<210> SEQ ID NO 97
<211> LENGTH: 67
<212> TYPE: DNA
<213> ORGANISM: Artificial Sequence
<220> FEATURE:
<223> OTHER INFORMATION: Primer Sequence According to Table 1

<400> SEQUENCE: 97
accattcaat atcctgatta tgcggcttgg cagcggcagg tattttcatc ggaacgggta    60
caaattc    67

<210> SEQ ID NO 98
<211> LENGTH: 63

-continued

```
<212> TYPE: DNA
<213> ORGANISM: Artificial Sequence
<220> FEATURE:
<223> OTHER INFORMATION: Primer Sequence According to Table 1

<400> SEQUENCE: 98
ctcagccaac atgtcagtaa agaagcgagt atgttctgcc tgacttaccc ccatccgtgc    60
ctg                                                                  63

<210> SEQ ID NO 99
<211> LENGTH: 67
<212> TYPE: DNA
<213> ORGANISM: Artificial Sequence
<220> FEATURE:
<223> OTHER INFORMATION: Primer Sequence According to Table 1

<400> SEQUENCE: 99
accattcaat atcctgatta tgcggcttgg cagcggcagg tattttcggc agcacagata    60
cagtctc                                                              67

<210> SEQ ID NO 100
<211> LENGTH: 61
<212> TYPE: DNA
<213> ORGANISM: Artificial Sequence
<220> FEATURE:
<223> OTHER INFORMATION: Primer Sequence According to Table 1

<400> SEQUENCE: 100
ctcagccaac atgtcagtaa agaagcgagt atgttctgcc tgactcacgc ccaaccggac    60
c                                                                    61

<210> SEQ ID NO 101
<211> LENGTH: 69
<212> TYPE: DNA
<213> ORGANISM: Artificial Sequence
<220> FEATURE:
<223> OTHER INFORMATION: Primer Sequence According to Table 1

<400> SEQUENCE: 101
accattcaat atcctgatta tgcggcttgg cagcggcagg tattttctgc tgatcgtatt    60
caggtgcag                                                            69

<210> SEQ ID NO 102
<211> LENGTH: 61
<212> TYPE: DNA
<213> ORGANISM: Artificial Sequence
<220> FEATURE:
<223> OTHER INFORMATION: Primer Sequence According to Table 1

<400> SEQUENCE: 102
ctcagccaac atgtcagtaa agaagcgagt atgttctgcc tgactcacgc ccaaccggac    60
c                                                                    61

<210> SEQ ID NO 103
<211> LENGTH: 67
<212> TYPE: DNA
<213> ORGANISM: Artificial Sequence
<220> FEATURE:
<223> OTHER INFORMATION: Primer Sequence According to Table 1

<400> SEQUENCE: 103
accattcaat atcctgatta tgcggcttgg cagcggcagg tatttcaggg tgaggtactg    60
``` gaaaagc                                                              67

<210> SEQ ID NO 104
<211> LENGTH: 63
<212> TYPE: DNA
<213> ORGANISM: Artificial Sequence
<220> FEATURE:
<223> OTHER INFORMATION: Primer Sequence According to Table 1

<400> SEQUENCE: 104
ctcagccaac atgtcagtaa agaagcgagt atgttctgcc tgacttacac tgcgggtttg    60
ggc                                                                  63

<210> SEQ ID NO 105
<211> LENGTH: 29
<212> TYPE: DNA
<213> ORGANISM: Artificial Sequence
<220> FEATURE:
<223> OTHER INFORMATION: Primer Sequence According to Table 1

<400> SEQUENCE: 105
agtcaggcag aacatactcg cttctttac                                      29

<210> SEQ ID NO 106
<211> LENGTH: 62
<212> TYPE: DNA
<213> ORGANISM: Artificial Sequence
<220> FEATURE:
<223> OTHER INFORMATION: Primer Sequence According to Table 1

<400> SEQUENCE: 106
tttgctcatg aactcgccag aaccagcagc ggagccagcg gatcccagcg cctccgcttc    60
ac                                                                   62

<210> SEQ ID NO 107
<211> LENGTH: 20
<212> TYPE: DNA
<213> ORGANISM: Artificial Sequence
<220> FEATURE:
<223> OTHER INFORMATION: Primer Sequence According to Table 1

<400> SEQUENCE: 107
gaccagacag aacatcaccg                                                20

<210> SEQ ID NO 108
<211> LENGTH: 17
<212> TYPE: DNA
<213> ORGANISM: Artificial Sequence
<220> FEATURE:
<223> OTHER INFORMATION: Primer Sequence According to Table 1

<400> SEQUENCE: 108
aaatacctgc cgctgcc                                                   17

<210> SEQ ID NO 109
<211> LENGTH: 59
<212> TYPE: DNA
<213> ORGANISM: Artificial Sequence
<220> FEATURE:
<223> OTHER INFORMATION: Primer Sequence According to Table 1

<400> SEQUENCE: 109
ccaacatgtc agtaaagaag cgagtatgtt ctgcctgact cacactcagg atttgagcg     59

```
<210> SEQ ID NO 110
<211> LENGTH: 60
<212> TYPE: DNA
<213> ORGANISM: Artificial Sequence
<220> FEATURE:
<223> OTHER INFORMATION: Primer Sequence According to Table 1

<400> SEQUENCE: 110
attcaatatc ctgattatgc ggcttggcag cggcaggtat ttcagggtga ccgcctgacc      60

<210> SEQ ID NO 111
<211> LENGTH: 61
<212> TYPE: DNA
<213> ORGANISM: Artificial Sequence
<220> FEATURE:
<223> OTHER INFORMATION: Primer Sequence According to Table 1

<400> SEQUENCE: 111
ccaacatgtc agtaaagaag cgagtatgtt ctgcctgact catacctaga cgtgcctgtg      60
c                                                                     61

<210> SEQ ID NO 112
<211> LENGTH: 64
<212> TYPE: DNA
<213> ORGANISM: Artificial Sequence
<220> FEATURE:
<223> OTHER INFORMATION: Primer Sequence According to Table 1

<400> SEQUENCE: 112
attcaatatc ctgattatgc ggcttggcag cggcaggtat tttcggcaga acggatacaa      60
attc                                                                  64

<210> SEQ ID NO 113
<211> LENGTH: 56
<212> TYPE: DNA
<213> ORGANISM: Artificial Sequence
<220> FEATURE:
<223> OTHER INFORMATION: Primer Sequence According to Table 1

<400> SEQUENCE: 113
ccaacatgtc agtaaagaag cgagtatgtt ctgcctgact cacgcccaac cggacc         56

<210> SEQ ID NO 114
<211> LENGTH: 62
<212> TYPE: DNA
<213> ORGANISM: Artificial Sequence
<220> FEATURE:
<223> OTHER INFORMATION: Primer Sequence According to Table 1

<400> SEQUENCE: 114
attcaatatc ctgattatgc ggcttggcag cggcaggtat tttcggcagc acagatacag      60
tc                                                                    62

<210> SEQ ID NO 115
<211> LENGTH: 60
<212> TYPE: DNA
<213> ORGANISM: Artificial Sequence
<220> FEATURE:
<223> OTHER INFORMATION: Primer Sequence According to Table 1

<400> SEQUENCE: 115
aaatacctgc cgctgccaag ccgcataatc aggatattga atcgtcaacg gtagcaacgg      60

<210> SEQ ID NO 116
```

```
<211> LENGTH: 60
<212> TYPE: DNA
<213> ORGANISM: Artificial Sequence
<220> FEATURE:
<223> OTHER INFORMATION: Primer Sequence According to Table 1

<400> SEQUENCE: 116
acctttccgc aatctggtgg ctcaggctcg gcaggggtt agtcaggctg agcatacccg    60

<210> SEQ ID NO 117
<211> LENGTH: 56
<212> TYPE: DNA
<213> ORGANISM: Artificial Sequence
<220> FEATURE:
<223> OTHER INFORMATION: Primer Sequence According to Table 1

<400> SEQUENCE: 117
ccaacatgtc agtaaagaag cgagtatgtt ctgcctgact cacgcccaac cggacc       56

<210> SEQ ID NO 118
<211> LENGTH: 64
<212> TYPE: DNA
<213> ORGANISM: Artificial Sequence
<220> FEATURE:
<223> OTHER INFORMATION: Primer Sequence According to Table 1

<400> SEQUENCE: 118
attcaatatc ctgattatgc ggcttggcag cggcaggtat tttctgctga tcgtattcag   60
gtgc                                                                64

<210> SEQ ID NO 119
<211> LENGTH: 62
<212> TYPE: DNA
<213> ORGANISM: Artificial Sequence
<220> FEATURE:
<223> OTHER INFORMATION: Primer Sequence According to Table 1

<400> SEQUENCE: 119
tcatgaactc gccagaacca gcagcggagc cagcggatcc cagcgcctcc gcttcacaat   60
tc                                                                  62

<210> SEQ ID NO 120
<211> LENGTH: 21
<212> TYPE: DNA
<213> ORGANISM: Artificial Sequence
<220> FEATURE:
<223> OTHER INFORMATION: Primer Sequence According to Table 1

<400> SEQUENCE: 120
agtcaggcag aacatactcg c                                             21

<210> SEQ ID NO 121
<211> LENGTH: 16
<212> TYPE: DNA
<213> ORGANISM: Artificial Sequence
<220> FEATURE:
<223> OTHER INFORMATION: Primer Sequence According to Table 1

<400> SEQUENCE: 121
aaccccctgc cgagcc                                                   16

<210> SEQ ID NO 122
<211> LENGTH: 16
<212> TYPE: DNA
<213> ORGANISM: Artificial Sequence
```

```
<220> FEATURE:
<223> OTHER INFORMATION: Primer Sequence According to Table 1

<400> SEQUENCE: 122
aaccccctgc cgagcc                                                   16

<210> SEQ ID NO 123
<211> LENGTH: 60
<212> TYPE: DNA
<213> ORGANISM: Artificial Sequence
<220> FEATURE:
<223> OTHER INFORMATION: Primer Sequence According to Table 1

<400> SEQUENCE: 123
aaatacctgc cgctgccaag ccgcataatc aggatattga attgccaatg gtggcaaggg    60

<210> SEQ ID NO 124
<211> LENGTH: 60
<212> TYPE: DNA
<213> ORGANISM: Artificial Sequence
<220> FEATURE:
<223> OTHER INFORMATION: Primer Sequence According to Table 1

<400> SEQUENCE: 124
acctttccgc aatctggtgg ctcaggctcg gcaggggtt agccagacag agcacacccg     60

<210> SEQ ID NO 125
<211> LENGTH: 61
<212> TYPE: DNA
<213> ORGANISM: Artificial Sequence
<220> FEATURE:
<223> OTHER INFORMATION: Primer Sequence According to Table 1

<400> SEQUENCE: 125
ccaacatgtc agtaaagaag cgagtatgtt ctgcctgact gatacccagc cgggcttgtg    60
c                                                                    61

<210> SEQ ID NO 126
<211> LENGTH: 63
<212> TYPE: DNA
<213> ORGANISM: Artificial Sequence
<220> FEATURE:
<223> OTHER INFORMATION: Primer Sequence According to Table 1

<400> SEQUENCE: 126
attcaatatc ctgattatgc ggcttggcag cggcaggtat tttcggttga acgcttacaa    60
tcc                                                                  63

<210> SEQ ID NO 127
<211> LENGTH: 56
<212> TYPE: DNA
<213> ORGANISM: Artificial Sequence
<220> FEATURE:
<223> OTHER INFORMATION: Primer Sequence According to Table 1

<400> SEQUENCE: 127
ccaacatgtc agtaaagaag cgagtatgtt ctgcctgact gacaccctgc cgagcc        56

<210> SEQ ID NO 128
<211> LENGTH: 61
<212> TYPE: DNA
<213> ORGANISM: Artificial Sequence
<220> FEATURE:
<223> OTHER INFORMATION: Primer Sequence According to Table 1
```

<400> SEQUENCE: 128
attcaatatc ctgattatgc ggcttggcag cggcaggtat tttctgatga aggcgtgcag 60
g 61

<210> SEQ ID NO 129
<211> LENGTH: 60
<212> TYPE: DNA
<213> ORGANISM: Artificial Sequence
<220> FEATURE:
<223> OTHER INFORMATION: Primer Sequence According to Table 1

<400> SEQUENCE: 129
aaatacctgc cgctgccaag ccgcataatc aggatattga atggtcaatg gcggcagcgg 60

<210> SEQ ID NO 130
<211> LENGTH: 60
<212> TYPE: DNA
<213> ORGANISM: Artificial Sequence
<220> FEATURE:
<223> OTHER INFORMATION: Primer Sequence According to Table 1

<400> SEQUENCE: 130
acctttccgc aatctggtgg ctcaggctcg gcaggggggtt agtcaggaag cgtacacgcg 60

<210> SEQ ID NO 131
<211> LENGTH: 7
<212> TYPE: PRT
<213> ORGANISM: Unknown
<220> FEATURE:
<223> OTHER INFORMATION: Sequence motif in C domains in multiple
      organisms
<220> FEATURE:
<221> NAME/KEY: misc_feature
<222> LOCATION: (3)..(5)
<223> OTHER INFORMATION: Xaa can be any naturally occurring amino acid

<400> SEQUENCE: 131

His His Xaa Xaa Xaa Asp Gly
1               5

<210> SEQ ID NO 132
<211> LENGTH: 5
<212> TYPE: PRT
<213> ORGANISM: Unknown
<220> FEATURE:
<223> OTHER INFORMATION: Conserved sequence in the C-A linker

<400> SEQUENCE: 132

Trp Asn Ala Thr Glu
1               5

<210> SEQ ID NO 133
<211> LENGTH: 32
<212> TYPE: PRT
<213> ORGANISM: Artificial Sequence
<220> FEATURE:
<223> OTHER INFORMATION: Consensus sequence according to Figure 1

<400> SEQUENCE: 133

Ile Gln Tyr Ala Asp Tyr Ala Val Trp Gln Arg Gln Trp Leu Gln Gly
1               5                   10                  15

Glu Arg Leu Thr Glu Gln Arg Asp Phe Trp Arg Thr Gln Leu Ala Gly
            20                  25                  30

<210> SEQ ID NO 134

-continued

```
<211> LENGTH: 39
<212> TYPE: DNA
<213> ORGANISM: Artificial Sequence
<220> FEATURE:
<223> OTHER INFORMATION: Consensus sequence according to Figure 7

<400> SEQUENCE: 134
caacatgtca gtaaagaagc gagtatgttc tgcctgact                              39

<210> SEQ ID NO 135
<211> LENGTH: 13
<212> TYPE: PRT
<213> ORGANISM: Artificial Sequence
<220> FEATURE:
<223> OTHER INFORMATION: Translation of consensus sequences according to
      Figure 7

<400> SEQUENCE: 135

Leu Met Asp Thr Phe Phe Arg Thr His Glu Ala Gln Ser
1               5                   10

<210> SEQ ID NO 136
<211> LENGTH: 39
<212> TYPE: DNA
<213> ORGANISM: Artificial Sequence
<220> FEATURE:
<223> OTHER INFORMATION: Complement sequence according to Figure 7

<400> SEQUENCE: 136
gttgtacagt catttcttcg ctcatacaag acggactga                              39
```